(12) United States Patent
Shalev et al.

(10) Patent No.: US 9,334,498 B2
(45) Date of Patent: May 10, 2016

(54) METHODS AND COMPOSITIONS FOR MODULATING MIR-204 ACTIVITY

(71) Applicant: UAB Research Foundation, Birmingham, AL (US)

(72) Inventors: Anath Shalev, Mountain View, AL (US); Guanlan Xu, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 14/400,292

(22) PCT Filed: May 10, 2013

(86) PCT No.: PCT/US2013/040549
§ 371 (c)(1),
(2) Date: Nov. 10, 2014

(87) PCT Pub. No.: WO2013/170146
PCT Pub. Date: Nov. 14, 2013

(65) Prior Publication Data
US 2015/0119449 A1   Apr. 30, 2015

Related U.S. Application Data

(60) Provisional application No. 61/645,523, filed on May 10, 2012.

(51) Int. Cl.
*C12N 15/113* (2010.01)
*A61K 31/70* (2006.01)

(52) U.S. Cl.
CPC .............. *C12N 15/113* (2013.01); *A61K 31/70* (2013.01); *C12N 2310/113* (2013.01); *C12N 2310/141* (2013.01); *C12N 2501/00* (2013.01)

(58) Field of Classification Search
None
See application file for complete search history.

(56) References Cited

U.S. PATENT DOCUMENTS

| | | | |
|---|---|---|---|
| 7,670,840 B2 | 3/2010 | Croce et al. | |
| 7,683,036 B2 | 3/2010 | Esau et al. | |
| 7,687,616 B1 | 3/2010 | Bentwich et al. | |
| 7,888,010 B2 | 2/2011 | Brown et al. | |
| 7,888,497 B2 | 2/2011 | Bentwich et al. | |
| 7,897,356 B2 | 3/2011 | Klass et al. | |
| 7,919,245 B2 | 4/2011 | Brown et al. | |
| 7,960,359 B2 | 6/2011 | Brown et al. | |
| 7,964,355 B2 | 6/2011 | Wang et al. | |
| 7,985,584 B2 | 7/2011 | Croce et al. | |
| 8,003,320 B2 | 8/2011 | Brown et al. | |
| 8,058,250 B2 | 11/2011 | Brown et al. | |
| 8,106,025 B2 | 1/2012 | Bennett et al. | |
| 8,110,558 B2 | 2/2012 | Bennett et al. | |
| 8,114,985 B2 | 2/2012 | Tuschl et al. | |
| 8,133,876 B2 | 3/2012 | Bennett et al. | |
| 8,158,601 B2 | 4/2012 | Chen et al. | |
| 2005/0256072 A1 | 11/2005 | Aronin et al. | |
| 2005/0261218 A1 | 11/2005 | Esau et al. | |
| 2006/0185027 A1 | 8/2006 | Bartel et al. | |
| 2007/0042380 A1 | 2/2007 | Bentwich et al. | |
| 2007/0099196 A1 | 5/2007 | Kauppinen et al. | |
| 2007/0161004 A1 | 7/2007 | Brown et al. | |
| 2008/0026951 A1 | 1/2008 | Brown et al. | |
| 2008/0171667 A1 | 7/2008 | Brown et al. | |
| 2008/0171715 A1 | 7/2008 | Brown et al. | |
| 2008/0176766 A1 | 7/2008 | Brown et al. | |
| 2008/0182245 A1 | 7/2008 | Brown et al. | |
| 2008/0261908 A1 | 10/2008 | Croce et al. | |
| 2008/0306018 A1 | 12/2008 | Croce et al. | |
| 2009/0176723 A1 | 7/2009 | Brown et al. | |
| 2009/0181390 A1 | 7/2009 | Li et al. | |
| 2009/0186348 A1 | 7/2009 | Huibregtse et al. | |
| 2009/0203893 A1* | 8/2009 | Esau ..................... | C12N 5/111 536/24.5 |
| 2009/0209450 A1 | 8/2009 | Croce et al. | |
| 2009/0221428 A1 | 9/2009 | Young et al. | |
| 2009/0286753 A1 | 11/2009 | Kauppinen et al. | |
| 2009/0286969 A1 | 11/2009 | Esau et al. | |
| 2009/0291906 A1 | 11/2009 | Esau et al. | |
| 2009/0291907 A1 | 11/2009 | Esau et al. | |
| 2009/0298174 A1 | 12/2009 | Esau et al. | |
| 2009/0298910 A1 | 12/2009 | Griffey et al. | |
| 2009/0317907 A1 | 12/2009 | Esau et al. | |
| 2010/0029003 A1 | 2/2010 | Bartel et al. | |
| 2010/0173288 A1 | 7/2010 | Zhang et al. | |
| 2010/0184046 A1 | 7/2010 | Klass et al. | |
| 2010/0197774 A1 | 8/2010 | Croce et al. | |
| 2010/0203529 A1 | 8/2010 | Kuslich et al. | |
| 2010/0256222 A1 | 10/2010 | Kelley et al. | |
| 2010/0267813 A1 | 10/2010 | Esau et al. | |
| 2010/0286044 A1 | 11/2010 | Litman et al. | |
| 2010/0286232 A1 | 11/2010 | Schmittgen et al. | |
| 2010/0292310 A1 | 11/2010 | Kelley et al. | |
| 2010/0305188 A1 | 12/2010 | Nakano et al. | |
| 2011/0003704 A1 | 1/2011 | Skog et al. | |
| 2011/0105583 A1 | 5/2011 | Cleary et al. | |
| 2011/0112173 A1 | 5/2011 | Brown et al. | |
| 2011/0142913 A1 | 6/2011 | Juo et al. | |
| 2011/0143948 A1 | 6/2011 | Perera | |
| 2011/0151460 A1 | 6/2011 | Klass et al. | |

(Continued)

FOREIGN PATENT DOCUMENTS

WO   WO 2005/078096 A2   8/2005
WO   WO 2005/118806 A2   12/2005

(Continued)

OTHER PUBLICATIONS

Conte, et al. (2009) PNAS, v.107(35):15491-6.*

(Continued)

*Primary Examiner* — Jennifer Pitrak McDonald
(74) *Attorney, Agent, or Firm* — Myers Bigel & Sibley, P.A.

(57) ABSTRACT

The present invention provides compositions and methods for regulating insulin production.

20 Claims, 21 Drawing Sheets

(56) References Cited

U.S. PATENT DOCUMENTS

| | | | |
|---|---|---|---|
| 2011/0171646 | A1 | 7/2011 | Schmittgen et al. |
| 2011/0190372 | A1 | 8/2011 | Tomic-Canic et al. |
| 2011/0224277 | A1 | 9/2011 | Esau et al. |
| 2011/0237450 | A1 | 9/2011 | Klass et al. |
| 2011/0287970 | A1 | 11/2011 | Croce et al. |
| 2011/0313025 | A1 | 12/2011 | Brown et al. |
| 2012/0015351 | A1 | 1/2012 | Lee et al. |
| 2012/0035248 | A9 | 2/2012 | Bennett et al. |
| 2012/0040353 | A1 | 2/2012 | Kerin et al. |
| 2012/0065248 | A1 | 3/2012 | Brown et al. |
| 2012/0101001 | A1 | 4/2012 | Suthanthiran |

FOREIGN PATENT DOCUMENTS

| | | |
|---|---|---|
| WO | WO 2006/047454 A2 | 5/2006 |
| WO | WO 2006/069584 A2 | 7/2006 |
| WO | WO 2006/137941 A2 | 12/2006 |
| WO | WO 2007/030678 A2 | 3/2007 |
| WO | WO 2007/073737 A1 | 7/2007 |
| WO | WO 2007/081680 A2 | 7/2007 |
| WO | WO 2007/103808 A2 | 9/2007 |
| WO | WO 2007/109236 A2 | 9/2007 |
| WO | WO 2007/112754 A2 | 10/2007 |
| WO | WO 2008/147837 A1 | 12/2008 |
| WO | WO 2008/147839 A1 | 12/2008 |
| WO | WO 2009/036332 A1 | 3/2009 |
| WO | WO 2009/043353 A2 | 4/2009 |
| WO | WO 2009/099905 A2 | 8/2009 |
| WO | WO 2009/151600 A2 | 12/2009 |
| WO | WO 2010/027838 A1 | 3/2010 |
| WO | WO 2010/056337 A2 | 5/2010 |
| WO | WO 2010/056737 A2 | 5/2010 |
| WO | WO 2010/105275 A2 | 9/2010 |
| WO | WO 2010/108126 A2 | 9/2010 |
| WO | WO 2010/118979 A1 | 10/2010 |
| WO | WO 2010/138263 A2 | 12/2010 |
| WO | WO 2011/028550 A1 | 3/2011 |
| WO | WO 2011/029903 A1 | 3/2011 |
| WO | WO 2011/088226 A2 | 7/2011 |
| WO | WO 2011/094335 A2 | 8/2011 |
| WO | WO 2011/109440 A1 | 9/2011 |
| WO | WO 2011/127219 A1 | 10/2011 |
| WO | WO 2011/137288 A2 | 11/2011 |
| WO | WO 2011/143499 A1 | 11/2011 |
| WO | WO 2011/154008 A1 | 12/2011 |
| WO | WO 2012/012051 A2 | 1/2012 |
| WO | WO 2012/013821 A1 | 2/2012 |
| WO | WO 2012/020307 A2 | 2/2012 |
| WO | WO 2012/020308 A2 | 2/2012 |
| WO | WO 2012/024543 A1 | 2/2012 |
| WO | WO 2012/027206 A1 | 3/2012 |
| WO | WO 2012/038956 A1 | 3/2012 |
| WO | WO 2012/048236 A1 | 4/2012 |

OTHER PUBLICATIONS

Bak, et al. (2008) RNA, v.14:432-44.*
Fernandez-Valverde et al. "MicroRNAs in β-Cell Biology, Insulin Resistance, Diabetes and Its Complications" *Diabetes* 60:1825-1831 (2011).
International Preliminary Report on Patentability corresponding to International Application No. PCT/US2013/040549; mailed Nov. 20, 2014.
International Search Report and the Written Opinion of the International Searching Authority corresponding to International Application No. PCT/US2013/040549; mailed Aug. 6, 2013.
Melkman-Zehavi et al. "miRNAs control insulin content in pancreatic β-cells via downregulation of transcriptional repressors" *The EMBO Journal* 30:835-845 (2011).
Stenvang et al. "Inhibition of microRNA function by antimiR oligonucleotides" *Silence* 3(1):1-17 (2012).
Aramata et al. "Synergistic activation of the insulin gene promoter by the β-cell enriched transcription factors MafA, Beta2, and Pdx1" *Biochimica et Biophysica Acta* 1730:41-46 (2005).
Artner et al. "MafA and MafB Regulate Genes Critical to β-Cells in a Unique Temporal Manner" *Diabetes* 59:2530-2539 (2010).
Bang-Berthelsen et al. "Independent component and pathway-based analysis of miRNA-regulated gene expression in a model of type 1 diabetes" *BMC Genomics* 12(97):211 (2011).
Barik, Sailen "An intronic microRNA silences genes that are functionally antagonistic to its host gene" *Nucleic Acids Research* 36(16):5232-5241 (2008).
Bolmeson et al. "Differences in islet-enriched miRNAs in healthy and glucose intolerant human subjects" *Biochemical and Biophysical Research Communications* 404:16-22 (2011).
Care et al. "*MicroRNA*-133 controls cardiac hypertrophy" *Nature Medicine* 13(5):613-618 (2007).
Cha-Molstad et al. "Glucose-stimulated Expression of Txnip is Mediated by Carbohydrate Response Element-binding Protein, p300, and Histone H4 Acetylation in Pancreatic Beta Cells" *The Journal of Biological Chemistry* 284(25):16898-16905 (2009).
Chen et al. "Thioredoxin-Interacting Protein: A Critical Link Between Glucose Toxicity and β-Cell Apoptosis" *Diabetes* 57:938-944 (2008).
Chen et al. "Thioredoxin-interacting protein deficiency induces Akt/Bcl-xL signaling and pancreatic beta-cell mass and protects against diabetes" *The FASEB Journal* 22:3581-3594 (2008).
Chen et al. "Lack of TXNIP Protects Against Mitochondria-Mediated Apoptosis but Not Against Fatty Acid-Induced ER Stress-Mediated β-Cell Death" *Diabetes* 59:440-447 (2010).
Chutkow et al. "Thioredoxin-interacting Protein (Txnip) is a Critical Regulator of Hepatic Glucose Production" *The Journal of Biological Chemistry* 283(4):2397-2406 (2008).
Clee et al. "Genetic and Genomic Studies of the BTBR *ob/ob* Mouse Model of Type 2 Diabetes" *American Journal of Therapeutics* 12:491-498 (2005).
Courboulin et al. "Role for miR-204 in human pulmonary arterial hypertension" *The Journal of Experimental Medicine* 208(3):535-548 (2011).
El Ouaamari et al. "miR-375 Targets 3'-Phosphoinositide-Dependent Protein Kinase-1 and Regulates Glucose-Induced Biological Responses in Pancreatic β-Cells" *Diabetes* 57:2708-2717 (2008).
Fred et al. "High Glucose Suppresses Human Islet Insulin Biosynthesis by Inducing miR-133a Leading to Decreased Polypyrimidine Tract Binding Protein-Expression" *PLoS One* 5(5):e10843 (2010).
Guay et al. "Diabetes mellitus, a microRNA-related disease?" *Translational Research* 157:253-264 (2011).
Hennessy et al. "Identification of microRNAs with a role in glucose stimulated insulin secretion by expression profiling of MIN6 cells" *Biochemical and Biophysical Research Communications* 396(2):457-462 (2010).
Huang et al. "MicroRNA-204 Regulates Runx2 Protein Expression and Mesenchymal Progenitor Cell Differentiation" *Stem Cells* 28(2):357-364 (2010).
Jegga et al. "Systems biology of the autophagy-lysosomal pathway" *Autophagy* 7(5):477-489 (2011).
Junn et al. "Vitamin $D_3$ Up-Regulated Protein 1 Mediates Oxidative Stress Via Suppressing the Thioredoxin Function[1]" *The Journal of Immunology* 164:6287-6295 (2000).
Kalis et al. "Beta-Cell Specific Deletion of *Dicer1* Leads to Defective Insulin Secretion and Diabetes Mellitus" *PLoS One* 6(12):e29166 (2011).
Kantharidis et al. "Diabetes Complications: The MicroRNA Perspective" *Diabetes* 60:1832-1837 (2011).
Khoo et al. "MAP Kinases and their Roles in Pancreatic β-Cells" *Cell Biochemistry and Biophysics* 40:191-200 (2004).
Kostromina et al. "Glucose Intolerance and Impaired Insulin Secretion in Pancreas-Specific Signal Transducer and Activator of Transcription-3 Knockout Mice are Associated with Microvascular Alterations in the Pancreas" *Endocrinology* 151:2050-2059 (2010).
Krol et al. "Characterizing Light-Regulated Retinal MicroRNAs Reveals Rapid Turnover as a Common Property of Neuronal MicroRNAs" *Cell* 141:618-631 (2010).
Krützfeldt et al. "Silencing of microRNAs in vivo with 'antagomirs'" *Nature* 438:685-689 (2005).

(56) References Cited

OTHER PUBLICATIONS

Landgraf et al. "A Mammalian microRNA Expression Atlas Based on Small RNA Library Sequencing" *Cell* 129(7):1401-1414 (2007).
Lawrence et al. "ERK1/2-dependent Activation of Transcription Factors Required for Acute and Chronic Effects of Glucose on the Insulin Gene Promoter" *The Journal of Biological Chemistry* 280(29):26751-26759 (2005).
Le Lay et al. "Involvement of PDX-1 in activation of human insulin gene transcription" *Journal of Endocrinology* 188:287-294 (2006).
Lee et al. "Exosomes Mediate the Cytoprotective Action of Mesenchymal Stromal Cells on Hypoxia-Induced Pulmonary Hypertension" *Circulation* 126:2601-2611 (2012).
Lynn et al. "MicroRNA Expression is Required for Pancreatic Islet Cell Genesis in the Mouse" *Diabetes* 56:2938-2945 (2007).
Matsuoka et al. "Regulation of MafA Expression in Pancreatic β-Cells in db/db Mice with Diabetes" *Diabetes* 59:1709-1720 (2010).
Minn et al. "Gene expression profiling in INS-1 cells overexpressing thioredoxin-interacting protein" *Biochemical and Biophysical Research Communications* 336:770-778 (2005).
Minn et al. "Thioredoxin-Interacting Protein is Stimulated by Glucose through a Carbohydrate Response Element and Induces β-Cell Apoptosis" *Endocrinology* 146(5):2397-2405 (2005).
Minn et al. "Metabolism-Independent Sugar Effects on Gene Transcription: The Role of 3-O-Methylglucose" *Biochemistry* 45(37):11047-11051 (2006).
Moitra et al. "Life without white fat: a transgenic mouse" *Genes & Development* 12:3168-3181 (1998).
Nishiyama et al. "Identification of Thioredoxin-binding Protein-2/Vitamin $D_3$ Up-regulated Protein 1 as a Negative Regulator of Thioredoxin Function and Expression" *The Journal of Biological Chemistry* 274(31):21645-21650 (1999).
Nishiyama et al. "Redox Regulation by Thioredoxin and Thioredoxin-Binding Proteins" *Life* 52:29-33 (2001).
Pandey et al. "Systems biology approach to identify transcriptome reprogramming and candidate microRNA targets during the progression of polycystic kidney disease" *BMC Systems Biology* 5(56):1-23 (2011).
Parikh et al. "TXNIP Regulates Peripheral Glucose Metabolism in Humans" *PLoS Medicine* 4(5):e158 (2007).
Patwari et al. "The Interaction of Thioredoxin with Txnip" *The Journal of Biological Chemistry* 281(31):21884-21891 (2006).
Paulin et al. "Dehydroepiandrosterone inhibits the Src/STAT3 constitutive activation in pulmonary arterial hypertension" *The American Journal of Physiology—Heart and Circulatory Physiology* 310:H1798-H1809 (2011).
Paulin et al. "From oncoproteins/tumor suppressors to microRNAs, the newest therapeutic targets for pulmonary arterial hypertension" *Journal of Molecular Medicine* 89:1089-1101 (2011).
Poitout et al. "Minireview: Secondary β-Cell Failure in Type 2 Diabetes—A Convergence of Glucotoxicity and Lipotoxicity" *Endocrinology* 143(2):339-342 (2002).
Poy et al. "A pancreatic islet-specific microRNA regulates insulin secretion" *Nature* 432:226-230 (2004).
Poy et al. "miR-375 maintains normal pancreatic α- and β-cell mass" *Proceedings of the National Academy of Sciences* 106(14):5813-5818 (2009).
Rani et al. "Decreasing Txnip mRNA and Protein Levels in Pancreatic MIN6 Cells Reduces Reactive Oxygen Species and Restores Glucose Regulated Insulin Secretion" *Cellular Physiology and Biochemistry* 25:667-674 (2010).
Roggli et al. "Involvement of MicroRNAs in the Cytotoxic Effects Exerted by Proinflammatory Cytokines on Pancreatic β-Cells" *Diabetes* 59:978-986 (2010).
Roldo et al. "MicroRNA Expression Abnormalities in Pancreatic Endocrine and Acinar Tumors are Associated with Distinctive Pathologic Features and Clinical Behavior" *Journal of Clinical Oncology* 24(29):4677-4684 (2006).
Ruan et al. "The microRNA-21—PDCD4 axis prevents type 1 diabetes by blocking pancreatic β cell death" *Proceedings of the National Academy of Sciences* 108(29):12030-12035 (2011).
Saxena et al. "Intracellular Shuttling and Mitochondrial Function of Thioredoxin-interacting Protein" *The Journal of Biological Chemistry* 285(6):3997-4005 (2010).
Shalev et al. "Oligonucleotide Microarray Analysis of Intact Human Pancreatic Islets: Identification of Glucose-Responsive Genes and a Highly Regulated TGFα Signaling Pathway" *Endocrinology* 143(9):3695-3698 (2002).
Sharma et al. "The NeuroD1/BETA2 Sequences Essential for Insulin Gene Transcription Colocalize with those Necessary for Neurogenesis and p300/CREB Binding Protein Binding" *Molecular and Cellular Biology* 19(1):704-713 (1999).
Sun et al. "Development of a micro-array to detect human and mouse microRNAs and characterization of expression in human organs" *Nucleic Acids Research* 32(22):e188 (2004).
Tang et al. "Identification of glucose-regulated miRNAs from pancreatic β cells reveals a role for miR-30d in insulin transcription" *RNA* 15:287-293 (2009).
Tattikota et al. "Re-dicing the pancreatic β-cell: do microRNAs define cellular identity?" *The EMBO Journal* 30:797-799 (2011).
Vanderford et al. "Glucose Induces MafA Expression in Pancreatic Beta Cell Lines via the Hexosamine Biosynthetic Pathway" *The Journal of Biological Chemistry* 282(3):1577-1584 (2007).
Vanhoose et al. "MafA and MafB Regulate Pdx1 Transcription through the Area II Control Region in Pancreatic β Cells" *The Journal of Biological Chemistry* 283(33):22612-22619 (2008).
Winter et al. "Many roads to maturity: microRNA biogenesis pathways and their regulation" *Nature Cell Biology* 11(3):228-234 (2009).
Wu et al. "Altered MicroRNA Expression Profiles in Retinas with Diabetic Retinopathy" *Ophthalmic Research* 47:195-201 (2012).
Xu et al. "Preventing β-Cell Loss and Diabetes with Calcium Channel Blockers" *Diabetes* 61:848-856 (2012).
Yamanaka et al. "A Possible Interaction of Thioredoxin with VDUP1 in HeLa Cells Detected in a Yeast Two-Hybrid System" *Biochemical and Biophysical Research Communications* 271:796-800 (2000).
Zhang et al. "MafA is a Key Regulator of Glucose-Stimulated Insulin Secretion" *Molecular and Cellular Biology* 25(12):4969-4976 (2005).
Zhao et al. "Up-Regulated Pancreatic Tissue MicroRNA-375 Associates with Human Type 2 Diabetes Through β-Cell Deficit and Islet Amyloid Deposition" *Pancreas* 39:843-846 (2010).
Zhao et al. "MicroRNA-30d Induces Insulin Transcription Factor MafA and Insulin Production by Targeting Mitogen-activated Protein 4 Kinase 4 (MAP4K4) in Pancreatic β-Cells" *The Journal of Biological Chemistry* 287(37):31155-31164 (2012).

\* cited by examiner

SEQUENCE LISTING

```
<160> NUMBER OF SEQ ID NOS: 37

<210> SEQ ID NO 1
<211> LENGTH: 22
<212> TYPE: DNA
<213> ORGANISM: Artificial
<220> FEATURE:
<223> OTHER INFORMATION: microRNA antagonist sequence

<400> SEQUENCE: 1
aggcauagga ugacaaaggg aa                                            22

<210> SEQ ID NO 2
<211> LENGTH: 22
<212> TYPE: DNA
<213> ORGANISM: Artificial
<220> FEATURE:
<223> OTHER INFORMATION: miR-204 sequence

<400> SEQUENCE: 2
uucccuuugu cauccuaugc cu                                            22

<210> SEQ ID NO 3
<211> LENGTH: 32
<212> TYPE: DNA
<213> ORGANISM: Artificial
<220> FEATURE:
<223> OTHER INFORMATION: Cloning primer

<400> SEQUENCE: 3
agaacgcgtc cccgccctgc agcctccagc tc                                 32

<210> SEQ ID NO 4
<211> LENGTH: 31
<212> TYPE: DNA
<213> ORGANISM: Artificial
<220> FEATURE:
<223> OTHER INFORMATION: Cloning primer
```

```
<400> SEQUENCE: 4
agaaagcttt tctgatgcag cctgtcctgg a                                31

<210> SEQ ID NO 5
<211> LENGTH: 27
<212> TYPE: DNA
<213> ORGANISM: Artificial
<220> FEATURE:
<223> OTHER INFORMATION: Cloning primer

<400> SEQUENCE: 5
ataactagtg cgcgggaccc tgggcct                                     27

<210> SEQ ID NO 6
<211> LENGTH: 34
<212> TYPE: DNA
<213> ORGANISM: Artificial
<220> FEATURE:
<223> OTHER INFORMATION: Cloning primer

<400> SEQUENCE: 6 agtgttaaa cttcttcctt tcctcagttt tgta                              34

<210> SEQ ID NO 7
<211> LENGTH: 28
<212> TYPE: DNA
<213> ORGANISM: Artificial
<220> FEATURE:
<223> OTHER INFORMATION: Cloning primer

<400> SEQUENCE: 7
tactgcctat cggcccgagc cagatctg                                    28

<210> SEQ ID NO 8
<211> LENGTH: 28
<212> TYPE: DNA
<213> ORGANISM: Artificial
<220> FEATURE:
<223> OTHER INFORMATION: Cloning primer

<400> SEQUENCE: 8
gggccgatag gcagtattca ccgttctc                                    28

<210> SEQ ID NO 9
<211> LENGTH: 20
<212> TYPE: DNA
<213> ORGANISM: Artificial
<220> FEATURE:
<223> OTHER INFORMATION: qPCR primer

<400> SEQUENCE: 9
cgagtcaaag ccgtcaggat                                             20

<210> SEQ ID NO 10
<211> LENGTH: 24
<212> TYPE: DNA
<213> ORGANISM: Artificial
<220> FEATURE:
<223> OTHER INFORMATION: qPCR primer

<400> SEQUENCE: 10
ttcatagcgc aagtagtcca aagt                                        24

<210> SEQ ID NO 11
<211> LENGTH: 17
```

```
<212> TYPE: DNA
<213> ORGANISM: Artificial
<220> FEATURE:
<223> OTHER INFORMATION: qPCR primer

<400> SEQUENCE: 11
aggttgcccg gcagaag                                                    17

<210> SEQ ID NO 12
<211> LENGTH: 23
<212> TYPE: DNA
<213> ORGANISM: Artificial
<220> FEATURE:
<223> OTHER INFORMATION: qPCR primer

<400> SEQUENCE: 12
gttggtagaa gggagcagat gct                                             23

<210> SEQ ID NO 13
<211> LENGTH: 18
<212> TYPE: DNA
<213> ORGANISM: Artificial
<220> FEATURE:
<223> OTHER INFORMATION: qPCR primer

<400> SEQUENCE: 13
acacctgtgc ggctcaca                                                   18

<210> SEQ ID NO 14
<211> LENGTH: 20
<212> TYPE: DNA
<213> ORGANISM: Artificial
<220> FEATURE:
<223> OTHER INFORMATION: qPCR primer

<400> SEQUENCE: 14
cgttccccgc acactaggta                                                 20

<210> SEQ ID NO 15
<211> LENGTH: 22
<212> TYPE: DNA
<213> ORGANISM: Artificial
<220> FEATURE:
<223> OTHER INFORMATION: qPCR primer

<400> SEQUENCE: 15
aggaggtcat ccgactgaaa ca                                              22

<210> SEQ ID NO 16
<211> LENGTH: 17
<212> TYPE: DNA
<213> ORGANISM: Artificial
<220> FEATURE:
<223> OTHER INFORMATION: qPCR primer

<400> SEQUENCE: 16
gcgtagccgc ggttctt                                                    17

<210> SEQ ID NO 17
<211> LENGTH: 22
<212> TYPE: DNA
<213> ORGANISM: Artificial
<220> FEATURE:
<223> OTHER INFORMATION: qPCR primer

<400> SEQUENCE: 17
```
cctacaaggt caagtgcgag aa                                             22

<210> SEQ ID NO 18
<211> LENGTH: 16
<212> TYPE: DNA
<213> ORGANISM: Artificial
<220> FEATURE:
<223> OTHER INFORMATION: qPCR primer

<400> SEQUENCE: 18
agcccgcctc cctgaa                                                    16

<210> SEQ ID NO 19
<211> LENGTH: 18
<212> TYPE: DNA
<213> ORGANISM: Artificial
<220> FEATURE:
<223> OTHER INFORMATION: qPCR primer

<400> SEQUENCE: 19
caaagctcac gcgtggaa                                                  18

<210> SEQ ID NO 20
<211> LENGTH: 19
<212> TYPE: DNA
<213> ORGANISM: Artificial
<220> FEATURE:
<223> OTHER INFORMATION: qPCR primer

<400> SEQUENCE: 20
tccggttctg ctgcgtatg                                                 19

<210> SEQ ID NO 21
<211> LENGTH: 18
<212> TYPE: DNA
<213> ORGANISM: Artificial
<220> FEATURE:
<223> OTHER INFORMATION: qPCR primer

<400> SEQUENCE: 21
tttggtggct ggctgctt                                                  18

<210> SEQ ID NO 22
<211> LENGTH: 23
<212> TYPE: DNA
<213> ORGANISM: Artificial
<220> FEATURE:
<223> OTHER INFORMATION: qPCR primer

<400> SEQUENCE: 22
gattctgctc aggcaagaaa gtc                                            23

<210> SEQ ID NO 23
<211> LENGTH: 20
<212> TYPE: DNA
<213> ORGANISM: Artificial
<220> FEATURE:
<223> OTHER INFORMATION: qPCR primer

<400> SEQUENCE: 23
agtcctgccc tttgtacaca                                                20

<210> SEQ ID NO 24
<211> LENGTH: 21
<212> TYPE: DNA
<213> ORGANISM: Artificial

<220> FEATURE:
<223> OTHER INFORMATION: qPCR primer

<400> SEQUENCE: 24
gatccgaggg cctcactaaa c                                          21

<210> SEQ ID NO 25
<211> LENGTH: 20
<212> TYPE: DNA
<213> ORGANISM: Artificial
<220> FEATURE:
<223> OTHER INFORMATION: ChIP primer

<400> SEQUENCE: 25
acgtccaatg agcgctttct                                            20

<210> SEQ ID NO 26
<211> LENGTH: 24
<212> TYPE: DNA
<213> ORGANISM: Artificial
<220> FEATURE:
<223> OTHER INFORMATION: ChIP primer

<400> SEQUENCE: 26
gctgaagctg taatttccaa acac                                       24

<210> SEQ ID NO 27
<211> LENGTH: 23
<212> TYPE: DNA
<213> ORGANISM: Artificial
<220> FEATURE:
<223> OTHER INFORMATION: ChIP control primer

<400> SEQUENCE: 27
accatgcttc actgacattc tga                                        23

<210> SEQ ID NO 28
<211> LENGTH: 20
<212> TYPE: DNA
<213> ORGANISM: Artificial
<220> FEATURE:
<223> OTHER INFORMATION: ChIP control primer

<400> SEQUENCE: 28
ggtctgcctc cctgctaacc                                            20

<210> SEQ ID NO 29
<211> LENGTH: 22
<212> TYPE: DNA
<213> ORGANISM: Artificial
<220> FEATURE:
<223> OTHER INFORMATION: qPCR primer

<400> SEQUENCE: 29
cttcgagaca cccctcctgt ac                                         22

<210> SEQ ID NO 30
<211> LENGTH: 19
<212> TYPE: DNA
<213> ORGANISM: Artificial
<220> FEATURE:
<223> OTHER INFORMATION: qPCR primer

<400> SEQUENCE: 30
tgcccaaatg ccagaatgt                                             19

```
<210> SEQ ID NO 31
<211> LENGTH: 21
<212> TYPE: DNA
<213> ORGANISM: Artificial
<220> FEATURE:
<223> OTHER INFORMATION: qPCR primer

<400> SEQUENCE: 31
gagcaagctc accgttctca a                                                   21

<210> SEQ ID NO 32
<211> LENGTH: 22
<212> TYPE: DNA
<213> ORGANISM: Artificial
<220> FEATURE:
<223> OTHER INFORMATION: microRNA antagonist sequence
<220> FEATURE:
<221> NAME/KEY: misc_feature
<222> LOCATION: (1)..(22)
<223> OTHER INFORMATION: 2'-O-methyl modification
<220> FEATURE:
<221> NAME/KEY: misc_feature
<222> LOCATION: (1)..(2)
<223> OTHER INFORMATION: Phosphorothioate backbone modification
<220> FEATURE:
<221> NAME/KEY: misc_feature
<222> LOCATION: (18)..(22)
<223> OTHER INFORMATION: Phosphorothioate backbone modification

<400> SEQUENCE: 32
aggcauagga ugacaaaggg aa                                                  22

<210> SEQ ID NO 33
<211> LENGTH: 22
<212> TYPE: DNA
<213> ORGANISM: Artificial
<220> FEATURE:
<223> OTHER INFORMATION: microRNA target sequence

<400> SEQUENCE: 33
uccguauccg acguuuccc uu                                                   22

<210> SEQ ID NO 34
<211> LENGTH: 21
<212> TYPE: DNA
<213> ORGANISM: Rattus norvegicus

<400> SEQUENCE: 34
aacggugaau acuuaaggga a                                                   21

<210> SEQ ID NO 35
<211> LENGTH: 21
<212> TYPE: DNA
<213> ORGANISM: Artificial
<220> FEATURE:
<223> OTHER INFORMATION: Mutated rat MafA UTR sequence

<400> SEQUENCE: 35
aacggugaau acugccuauc g                                                   21

<210> SEQ ID NO 36
<211> LENGTH: 22
<212> TYPE: DNA
<213> ORGANISM: Artificial
<220> FEATURE:
<223> OTHER INFORMATION: microRNA antagonist sequence
<220> FEATURE:
<221> NAME/KEY: misc_feature
```

```
<222> LOCATION: (1)..(22)
<223> OTHER INFORMATION: 2'-O-methyl modification
<220> FEATURE:
<221> NAME/KEY: misc_feature
<222> LOCATION: (1)..(2)
<223> OTHER INFORMATION: Phosphorothioate backbone modification
<220> FEATURE:
<221> NAME/KEY: misc_feature
<222> LOCATION: (18)..(22)
<223> OTHER INFORMATION: Phosphorothioate backbone modification

<400> SEQUENCE: 36
aggcauagga ugacaaaggg aa                                            22

<210> SEQ ID NO 37
<211> LENGTH: 22
<212> TYPE: DNA
<213> ORGANISM: Artificial
<220> FEATURE:
<223> OTHER INFORMATION: microRNA antagonist sequence
<220> FEATURE:
<221> NAME/KEY: misc_feature
<222> LOCATION: (1)..(22)
<223> OTHER INFORMATION: 2'-O-methyl modification
<220> FEATURE:
<221> NAME/KEY: misc_feature
<222> LOCATION: (1)..(2)
<223> OTHER INFORMATION: Phosphorothioate backbone modification
<220> FEATURE:
<221> NAME/KEY: misc_feature
<222> LOCATION: (19)..(22)
<223> OTHER INFORMATION: Phosphorothioate backbone modification
<220> FEATURE:
<221> NAME/KEY: misc_feature
<222> LOCATION: (22)..(22)
<223> OTHER INFORMATION: 3'-cholesterol modification

<400> SEQUENCE: 37
aggcauagga ugacaaaggg aa                                            22
```

US 9,334,498 B2

METHODS AND COMPOSITIONS FOR MODULATING MIR-204 ACTIVITY

STATEMENT OF PRIORITY

This application is a 35 USC §371 national phase application of International Application Ser. No. PCT/US2013/040549, filed May 10, 2013, which claims the benefit under 35 U.S.C. §119(e), of U.S. Provisional Application Ser. No. 61/645,523, filed on May 10, 2012, the disclosures of each of which are incorporated by reference herein in their entireties.

STATEMENT REGARDING ELECTRONIC FILING OF A SEQUENCE LISTING

A Sequence Listing is ASCII text format, submitted under 37 C.F.R. §1.821, entitled 5656-43TSX_ST25.txt, 7,836 bytes in size, generated on Dec. 14, 2015 and filed via EFS-Web, is provided in lieu of a paper copy. This Sequence Listing is hereby incorporated by reference into the specification for its disclosures.

FIELD OF INVENTION

The present invention relates to compositions and methods for modulating miR-204 activity, e.g., to treat disorders associated with abnormal or altered insulin production, such as diabetes.

BACKGROUND OF THE INVENTION

Type 2 diabetes (T2DM) has become a major public health issue (~26 million Americans have diabetes and ~79 million more have pre-diabetes) and the epidemic continues to grow such that diabetes may affect 1 in 3 Americans by 2050. While a number of therapies are available, they can significantly impact life quality, i.e., multiple daily insulin injections and often are not able to prevent devastating complications. T2DM is characterized by peripheral insulin resistance and loss of functional beta cell mass. When pancreatic beta cells can no longer keep up with the increased insulin requirements they decompensate leading to progressive beta cell dysfunction, impaired insulin gene transcription (1,2), irreversible beta cell loss by apoptosis (3,4) and hyperglycemia resulting in a vicious cycle with worsening of the diabetes. Promoting functional beta cell mass would therefore be an attractive therapeutic approach, be it by enhancing beta cell survival or beta cell function, i.e., insulin production. This approach would enhance the patient's own natural insulin production and reduce or eliminate the need for daily insulin injections and improve outcome.

microRNAs (small, 20-24 nucleotide, non-coding RNAs) recognize and bind to target mRNAs through imperfect base pairing leading to destabilization or translational inhibition of the target mRNA and thereby downregulate target gene expression (20,21). However, their overall role in beta cell biology is still not clear (24).

The present invention overcomes previous shortcomings in the art by providing methods and compositions for modulating the activity of miR-204, e.g., to treat disorders associated with abnormal or altered insulin production.

SUMMARY OF THE INVENTION

In one aspect, the present invention provides a method for treating diabetes in a subject in need thereof, comprising administering to the subject a microRNA-204 (miR-204) antagonist in an amount effective to reduce one or more symptoms of diabetes in the subject, thereby treating diabetes in the subject.

In a further aspect, the present invention provides a method of increasing insulin production in a cell that produces insulin, comprising contacting the cell with a microRNA-204 (miR-204) antagonist, thereby increasing insulin production in the cell.

Further provided herein is an isolated oligonucleotide consisting of about 15 to about 30 nucleotides, wherein the oligonucleotide comprises, at any location within the about 15 to about 30 nucleotides of the oligonucleotide, a region (e.g., of 4, 5, 6 or 7 contiguous nucleotides) of contiguous nucleotides that are complementary to the seed sequence of miR-204 (CCUUUCC) or complementary to a sequence having at least 70% (e.g., 70%, 85%, 90%, 95%, 100%) identity with the seed sequence of miR-204, wherein each nucleotide of said region of contiguous nucleotides is, in any combination, unmodified or comprises a modified nucleoside linkage (e.g., phosphorothioate, methyl phosphonate, phosphoramidate, and any combination thereof), and/or a modified sugar moiety (e.g., 2'-O-methyl sugar moiety, 2'-F sugar moiety, 2'-O-methoxyethyl sugar moiety, bicyclic sugar moiety, 2'N$_3$ sugar moiety, 4'thio sugar moiety, NH$_2$ sugar moiety, and any combination thereof), and each of the remaining nucleotides of the about 15 to about 30 nucleotide long oligonucleotide is nucleotide X, wherein X can be A, U, C or G in any combination in the nucleotide sequence of the oligonucleotide and wherein, in any combination among the Xs of the oligonucleotide, X is not modified or X comprises a modified nucleoside linkage (e.g., phosphorothioate, methyl phosphonate, phosphoramidate, and any combination thereof), and/or a modified sugar moiety (e.g., 2'-O-methyl sugar moiety, 2'-F sugar moiety, 2'-O-methoxyethyl sugar moiety, bicyclic sugar moiety, 2'N$_3$ sugar moiety, 4'thio sugar moiety, NH$_2$ sugar moiety, and any combination thereof).

Also provided herein is an isolated oligonucleotide consisting of about 15 to about 30 nucleotides, wherein the oligonucleotide comprises at least about 15 of the nucleotides of the nucleotide sequence of SEQ ID NO:1: 5' AGGCAUAG-GAUGACAAAGGGAA 3', or a nucleotide sequence having at least 90% identity with the nucleotide sequence of SEQ ID NO:1, wherein each nucleotide of the nucleotide sequence of SEQ ID NO:1 independently is not modified, or independently comprises a modified nucleoside linkage (e.g., phosphorothioate, methyl phosphonate, phosphoramidate, and any combination thereof), and/or a modified sugar moiety (e.g., 2'-O-methyl sugar moiety, 2'-F sugar moiety, 2'-O-methoxyethyl sugar moiety, bicyclic sugar moiety, 2'N$_3$ sugar moiety, 4'thio sugar moiety, NH$_2$ sugar moiety and any combination thereof).

In additional aspects of this invention, provided herein is a method of decreasing insulin production in a cell that produces insulin, comprising contacting the cell with a microRNA-204 (miR-204) mimic, thereby decreasing insulin production in the cell.

(p-STAT3) and total STAT3 in INS-TXNIP and control INS-LacZ cells. (E) To determine the role of STAT3 in miR-204 expression, INS-1 cells were incubated with the STAT3 inhibitor STATTIC (2 μM for 48 hr) or vehicle (DMSO) and the expression of miR-204 was detected by qRT-PCR. (F) To assess the effect of diabetes on miR-204 expression, primary islets of 10-week old, male, diabetic ob/ob or lean control mice were analyzed by qRT-PCR. Bars represent means±SEM; n=3-5 independent experiments.

Figure 19:
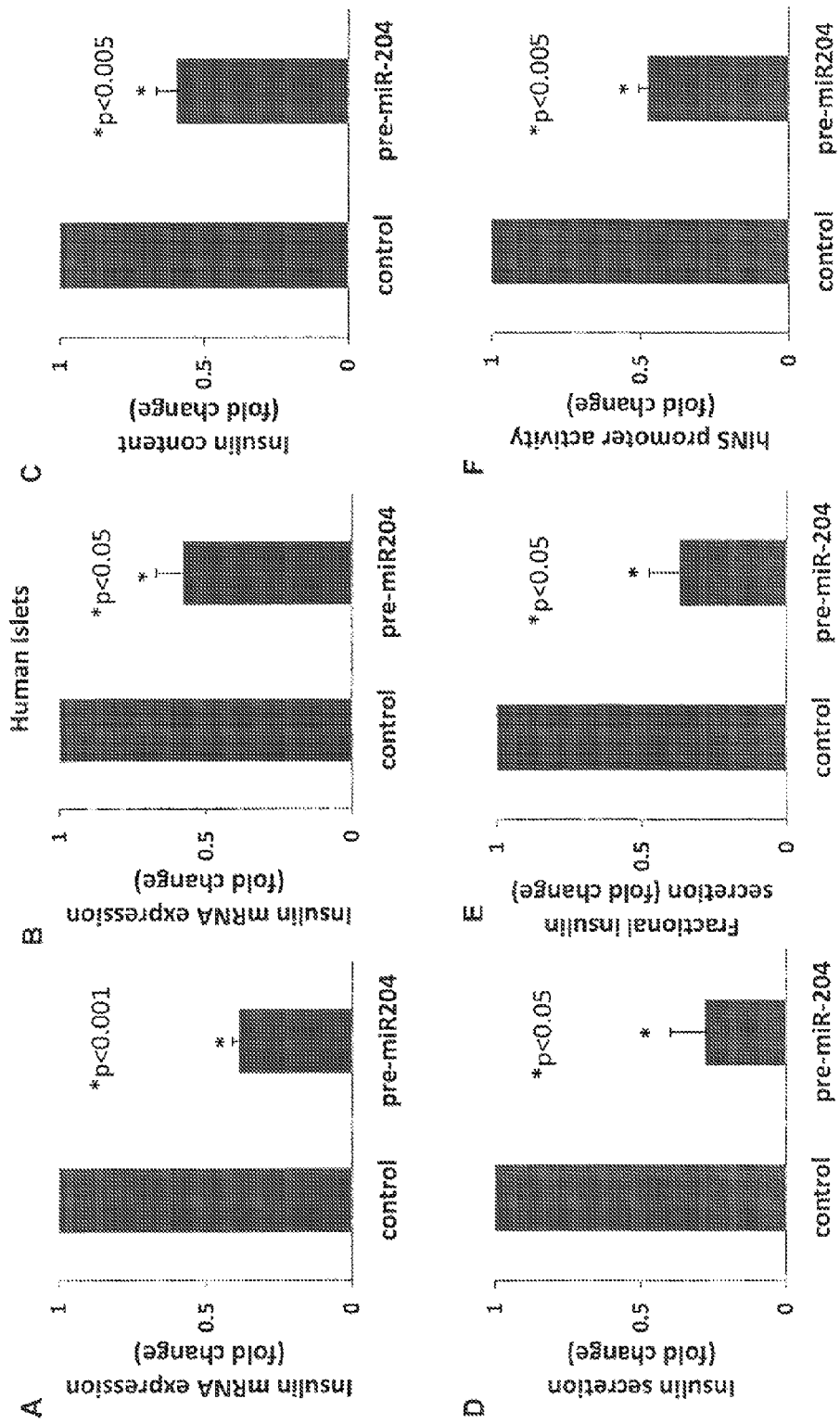

FIG. 19. miR-204 effects on insulin production. (A) INS-1 cells and (B) human islets were transfected with miR-204 precursor (pre-miR204) or scrambled control. 72 h after transfection RNA was extracted and analysed for insulin mRNA by qRT-PCR. (C) Cellular insulin protein content and (D) insulin secretion in INS-1 cells overexpressing miR-204 or scrambled control was assessed by ELISA and normalized for cellular DNA content, (Control insulin content: 7.5 and secretion 1.7 ng/ml/μgDNA) (E) Fractional insulin secretion as calculated by normalizing insulin secretion for insulin content. (F) INS-1 cells were cotransfected with the human insulin promoter reporter construct Ins-Luc, and pre-miR204 or control plasmid. Cells were harvested 72 h after transfection, and insulin promoter activity was assessed by firefly luciferase (and corrected for transfection efficiency with pRL-TK renilla luciferase). Bars represent means±SEM of 3 independent experiments.

Figure 20:
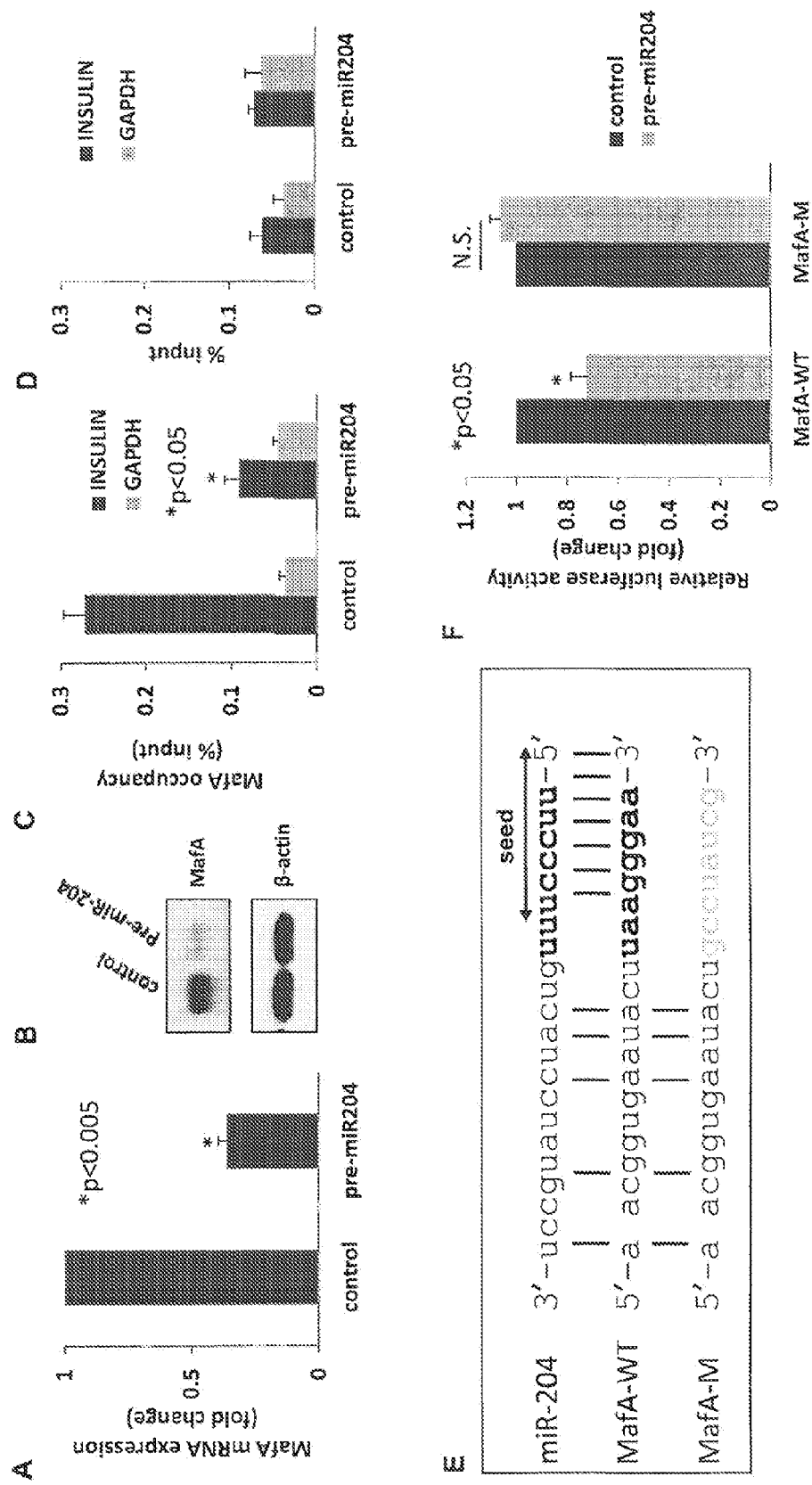

FIG. 20. MafA as a target of miR-204. Effects of miR-204 on MafA mRNA (A) or protein expression (B) as assessed by qRT-PCR and immunoblotting, (C) Changes in MafA occupancy of the insulin promoter in response to miR-204 as measured by ChIP; (D) IgG control. (E) Alignment of miR-204 (SEQ ID NO:33) seed sequence (arrow) and rat MafA 3'UTR (SEQ ID NO:34) target sequence (bold) as well as mutated (SEQ ID NO:35) target sequence (grey). (F) INS-1 cells were cotransfected with the wild-type MafA-WT-3'Luc or mutant MafA-M-3'Luc 3'UTR reporter plasmids and with miR-204 or scrambled control. 24 h after transfection, miR-204-directed repression of the luciferase reporter gene bearing the wild-type or mutant MafA 3'UTR segments was assessed. Bars represent means±SEM of 3 independent experiments and one representative immunoblot is shown.

Figure 21:
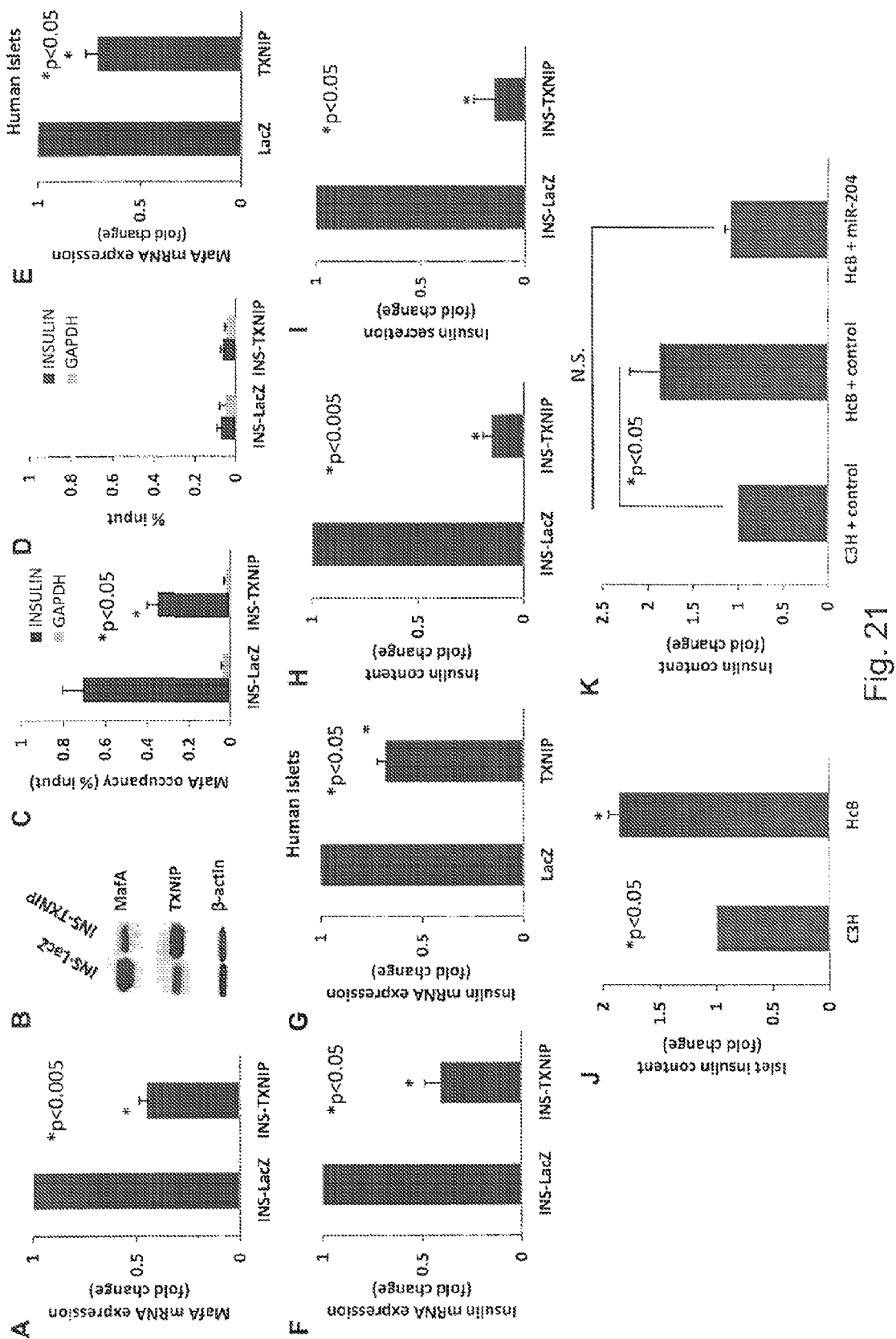

FIG. 21. TXNIP effects on MafA and insulin production. TXNIP overexpressing INS-TXNIP cells were analyzed for (A) MafA mRNA by qRT-PCR; (B) MafA protein by immunoblotting; and (C) MafA occupancy of the insulin promoter by ChIP, as compared to INS-LacZ control cells. (D) IgG control. (E) Human islets were transfected with CMV-hTXNIP or LacZ and the effects on MafA mRNA expression were assessed by qRT-PCR. Insulin mRNA as assessed by qRT-PCR in (F) INS-TXNIP cells and (G) human islets transfected with TXNIP. (H) Insulin content and (I) insulin secretion were assessed by ELISA in INS-TXNIP and INS-LacZ control cells, (Control LacZ insulin content: 8.1 and secretion: 1.7 ng/ml/μgDNA) (J) Islet insulin content was measured by ELISA in primary islets of TXNIP-deficient HcB-19 and control C3H mice. (K) Control C3H and TXNIP-deficient HcB-19 mouse islets were transfected with scrambled control or precursor miR-204 and 2 days later insulin content was measured by ELISA and normalized for DNA content. Bars represent means±SEM of 3 independent experiments.

DETAILED DESCRIPTION OF THE INVENTION

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration (e.g., the percentage of collagen in the biomatrix scaffold) and the like, is meant to encompass variations of 20%, 10%, 5%, 1%, 0.5%, or even 0.1% of the specified amount.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The present invention is described in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure that do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

The present invention is based on the unexpected discovery that the microRNA, miR-204 inhibits insulin production and that an antagonist of miR-204 can be used to increase insulin production. Thus, in one aspect, the present invention provides a method for treating diabetes in a subject in need thereof, comprising administering to the subject a microRNA-204 (miR-204) antagonist in an amount effective to reduce one or more symptoms of diabetes in the subject, thereby treating diabetes in the subject.

In a further embodiment, the present invention provides a method of increasing insulin production in a cell that produces insulin, comprising contacting the cell with a microRNA-204 (miR-204) antagonist, thereby increasing insulin production in the cell. In some embodiments, the cell of this method can be in a subject of this invention (i.e., in vivo) or the cell of this method can be in a cell culture (i.e., ex vivo or in vitro)

Nonlimiting examples of a cell of this invention include a pancreatic islet beta cell substitute, which can be, but is not limited to a fibroblast, a hepatocyte, a cord blood stem cell, an alpha cell, a ductal cell, an islet progenitor cell, a mesenchymal stem cell, a peripheral blood stem cell, a bone marrow derived stem cell and any other cell now known or later identified as suitable for use as a pancreatic islet beta cell substitute. The cells of this invention can be used singly and/or in any combination of cell types.

Nonlimiting examples of a disorder associated with abnormal of altered insulin production is Type I diabetes (insulin dependent diabetes, Type II diabetes (non-insulin dependent diabetes), and any less common form of diabetes mellitus.

A subject of this invention can be any animal that produces insulin and/or can be treated for diabetes. Nonlimiting examples of a subject of this invention include a mammal, a reptile, an avian or an amphibian (e.g., mouse, bird, dog, cat, cow, horse, fish). In certain embodiments of this invention, the subject is a mammalian subject and in particular embodiments, the subject is a human.

The cell of these methods can be in vitro (e.g., an isolated cell) and/or in vivo (e.g., in a cell in a subject) and/or ex vivo.

In some embodiments, the miR-204 antagonist of this invention is a repressor of miR-204 transcription and/or an inhibitor of transcriptional activity of miR-204. In various embodiments, the miR-204 antagonist is a modulator of expression of miR-204, including but not limited to Homeobox transcription factor Nanog; Brn-5, POU-VI protein class (also known as emb and CNS-1); Cone-rod homeobox-containing transcription factor; Hepatic leukemia factor; Tax/CREB complex; PAR-type chicken vitellogenin promoter-binding protein; Signal transducers and activators of transcription; *Drosophila* initiator motifs; Nuclear factor of activated T-cells 5; Interferon regulatory factor (IRF)-related protein (NF-EM5, PIP, LSIRF, ICSAT); Octamer-binding factor 1; Interferon regulatory factor 7 (IRF-7); TCF/LEF-1, involved in the Wnt signal transduction pathway; Transcription factor yin yang 2; Growth factor independence 1; Meis1a and Hoxa9 form heterodimeric binding complexes on target DNA; Member of the vertebrate HOX-cluster of homeobox factors; Abd-B-like homeodomain protein Hoxb-9; Gut-enriched Krueppel-like factor; Ecotropic viral integration site 1 encoded factor, amino-terminal zinc finger domain; Spi-B transcription factor (Spi-1/PU.1 related); Nuclear factor 1; NK2 homeobox 3, CSX 3; Bagpipe homeobox homolog 1 (homeodomain protein Nkx-3.2); SWI/SNF related, matrix associated, actin dependent regulator of chromatin, subfamily a, member 3; CCAAT/enhancer binding protein; Ikaros 2, potential regulator of lymphocyte differentiation; Heat shock factor 2; SWI/SNF related, matrix associated, actin dependent regulator of chromatin, subfamily a, member 3; NK2 homeobox 3, CSX 3; NK2 homeobox 9, NKX2H; Avian C-type LTR TATA box; Muscle TATA box; SWI/SNF related, matrix associated, actin dependent regulator of chromatin, subfamily a, member 3; Prostate-specific homeodomain protein NKX3.1; Fork head homologous X binds DNA with a dual sequence specificity (FHXA and FHXB); POZ/zinc finger protein, transcriptional repressor, translocations observed in diffuse large cell lymphoma; Heat shock factor 1; Heat shock factor 1; Photoreceptor-specific nuclear receptor subfamily 2, group E, member 3 (Nr2e3), DR1 sites; Avian C-type LTR TATA box; T-cell specific HMG-box transcription factor 7; Caudal type homeobox transcription factor 2; GATA-binding factor 3; *Xenopus* fork head domain factor 3 (FoxA2a); Homeodomain protein NKX3.2 (BAPX1, NKX3B, Bagpipe homolog); Brn-2, POU-III protein class; GATA-binding protein 6; Ecotropic viral integration site 1 encoded factor, amino-terminal zinc finger domain; Homeo domain factor Pbx-1; Cellular and viral CCAAT box; Cytoplasmic polyadenylated homeobox; Transcriptional repressor CDP; CUT-homeodomain transcription factor Onecut-2; PAX 2/5/8 binding site; FAST-1 SMAD interacting protein; Cart-1 (cartilage homeoprotein 1); GATA-binding factor 1; Thyrotrophic embryonic factor; E4BP4, bZIP domain, transcriptional repressor; Thyrotrophic embryonic factor; Heat shock factor 1; AT rich interactive domain 5A (MRF1-like); AT rich interactive domain 5A (MRF1-like); Pax-6 paired domain binding site; Brn-5, POU-VI protein class (also known as emb and CNS-1); PBX-HOXA9 binding site; Activator protein 4; Myogenic bHLH protein myogenin (myf4); Atonal homolog 1, HATH1, MATH-1; Atonal homolog 1, HATH1, MATH-1; PTF1 binding sites are bipartite with an E-box and a TC-box (RBP-J/L) spaced one helical turn apart; Transcription factor yin yang 2; GLI-Kruppel family member GLI3; Ras-responsive element binding protein 1; FAST-1 SMAD interacting protein; HNF-3/Fkh Homolog-8 (FOXF1); Octamer-binding factor 1; Meis1b and Hoxa9 form heterodimeric binding complexes on target DNA; GATA binding factor; Serum response factor; PAX6 paired domain binding site; Serum response factor; MyT1 zinc finger transcription factor involved in primary neurogenesis; Hepatic nuclear factor 4, DR2 sites; HMG box transcription factor Tcf711 (TCF3); GATA-binding factor 3; Octamer-binding factor 1; POU domain, class 5, transcription factor 1; Canonical palindromic estrogen response element (ERE), IR3 sites; Peroxisome proliferator-activated receptor gamma; Retinoid X receptor homodimer, DR1 sites; Hepatic nuclear factor 4, DR1 sites; Hematopoietically expressed homeobox, proline-rich homeodomain protein; Intestine specific homeodomain factor CDX-1; POU class 4 homeobox 3 (POU4F3), BRN3C; Barx2, homeobox transcription factor that preferentially binds to paired TAAT motifs; NK6 homeobox 1; POU class 6 homeobox 1 (POU6F1); Hox-1.3, vertebrate homeobox protein; Octamer-binding transcription factor-1, POU class 2 homeobox 1 (POU2F1); Spi-B transcription factor (Spi-1/PU.1 related); Promyelocytic leukemia zinc finger (TF with nine Krueppel-like zinc fingers); Androgene receptor binding site, IR3 sites; Cone-rod homeobox-containing transcription factor/otx-like homeobox gene; Brn-2, POU-III protein class; Homeobox B6/Hox2-beta; BARX homeobox 1; POZ/zinc finger protein, transcriptional repressor, translocations observed in diffuse large cell lymphoma; T-cell acute lymphocytic leukemia 1, SCL; GATA binding factor; SWI/SNF related, matrix associated, actin dependent regulator of chromatin, subfamily a, member 3; MyT1 zinc finger transcription factor involved in primary neurogenesis; Special AT-rich sequence-binding protein 1, predominantly expressed in thymocytes, binds to matrix attachment regions (MARs); Intestine specific homeodomain factor CDX-1; Fork head homologous X binds DNA with a dual sequence specificity (FHXA and FHXB); Homeobox D10; Hepatic nuclear factor 1; *Xenopus* fork head domain factor 3 (FoxA2a); Binding site for a Pbx1/Meis1 heterodimer; Octamer-binding factor 1; Liver enriched Cut-Homeodomain transcription factor HNF6 (ONECUT); TG-interacting factor belonging to TALE class of homeodomain factors; form heterodimeric binding complexes on target DNA; Meis1b and Hoxa9; Homeobox C13/Hox-3 gamma; NK2 homeobox 9, NKX2H; Heat shock factor 2; Heat shock factor 1; Bipartite binding site of VDR/RXR heterodimers, DR4 sites; NUDR (nuclear DEAF-1 related transcriptional regulator protein); Heat shock factor 1; HMG box-containing protein 1; Proximal sequence element (PSE) of RNA polymerase III-transcribed genes; Prolactin regulatory element-binding protein; MEF3 binding site, present in skeletal muscle-specific transcriptional enhancers; AT rich interactive domain 5A (MRF1-like); Fork head homologous X binds DNA with a dual sequence specificity (FHXA and FHXB); AT rich interactive domain 5A (MRF1-like); STAT6: signal transducer and activator of transcription 6; Heat shock factor 1; Doublesex and mab-3 related transcription factor 4; AREB6 (Atp1a1 regulatory element binding factor 6); Homeobox transcription factor Nanog; Growth factor independence 1; GATA-binding factor 3; Doublesex and mab-3 related transcription factor 2; Heat shock factor 1; Transcriptional repressor B lymphocyte-induced maturation protein-1 (Blimp-1, prdm1); Interferon-stimulated response element; Muscle TATA box; Zebrafish PAX2 paired domain protein; Muscle TATA box; Zinc finger protein 217; Homeobox transcription factor Nanog; TEA domain-containing factors, transcriptional enhancer factors 1,3,4,5; Zinc finger protein 410, APA-1; HMG box-containing protein 1; Gut-enriched Krueppel-like factor; Sox-5; Runt-related transcription factor 2/CBFA1 (core-binding factor, runt domain, alpha subunit 1); HMG box-containing protein 1; Homeobox transcription factor Nanog; HMG box-containing protein 1; Doublesex and mab-3 related transcription factor 1; Doublesex and mab-3 related transcription factor 1; AREB6 (Atp1a1 regulatory element binding factor 6); HNF-3/Fkh Homolog 2 (FOXD3); STAT6: signal transducer and activator of transcription 6; STAT6: signal transducer and activator of transcription 6; SRY (sex determining region Y)-box 9 homodimer; Octamer-binding factor 1; MyT1 zinc finger transcription factor involved in primary neurogenesis; Heat shock factor 2; SRY (sex determining region Y)-box 9 homodimer; Myelin transcription factor 1-like, neuronal C2HC zinc finger factor 1; CCAAT/enhancer binding protein beta; Photoreceptor-specific nuclear receptor subfamily 2, group E, member 3 (Nr2e3), DR1 sites; Neuron-restrictive silencer factor (11 bp spacer between half sites); Progesterone receptor binding site, IR3 sites; Complex of Lmo2 bound to Tal-1, E2A proteins, and GATA-1, half-site 2; Transcriptional repressor B lymphocyte-induced maturation protein-1 (Blimp-1, prdm1); Meis1b and Hoxa9 form heterodimeric binding complexes on target DNA; CCAAT/enhancer binding protein alpha; Myelin transcription factor 1-like, neuronal C2HC zinc finger factor 1; Barbiturate-inducible element; Transcription factor yin yang 2; NMP4 (nuclear matrix protein 4)/CIZ (Cas-interacting zinc finger protein); Nuclear factor of activated T-cells 5; Interferon regulatory factor 3 (IRF-3); Gut-enriched Krueppel-like factor; Gut-enriched Krueppel-like factor; Collagen krox protein (zinc finger protein 67-zfp67); GAGA-Box; Collagen krox protein (zinc finger protein 67-zfp67); EGR1, early growth response 1; GAGA-Box; GAGA-Box; Kruppel-like factor 7 (ubiquitous, UKLF); Purine-rich element binding protein A; Stimulating protein 1, ubiquitous zinc finger transcription factor; Wilms Tumor Suppressor; E2F-1/DP-2 heterodimeric complex; EGR1, early growth response 1; X gene core promoter element 1; Kruppel-like zinc finger protein 219; Zinc finger transcription factor OVO homolog-like 1; Tumor suppressor p53; Tumor suppressor p53; PAX5 paired domain protein; Non-palindromic nuclear factor I binding sites; Neuron-restrictive silencer factor (11 bp spacer between half sites); c-Myb, important in hematopoesis, cellular equivalent to avian myoblastosis virus oncogene v-myb; Hepatocyte nuclear factor 1 alpha (Tcf-1); Zinc finger transcription factor OVO homolog-like 1; Homeobox protein engrailed (en-1); Meis homeobox 1; Neural-restrictive-silencer-element; Early B-cell factor 1; Muscle-specific Mt binding site; RB/E2F-1/DP-1 heterotrimeric complex; Activating transcription factor 2; Winged helix protein, involved in hair keratinization and thymus epithelium differentiation; RB/E2F-1/DP-1 heterotrimeric complex; GATA-binding protein 3; LIM-homeodomain transcription factor LHX3; Cell cycle gene homology region (CDE/CHR tandem elements regulate cell cycle dependent repression); Cytoplasmic polyadenylated homeobox; TCF/LEF-1 (secondary DNA binding preference); Spermatogenic Zip 1 transcription factor; Ikaros 3, potential regulator of lymphocyte differentiation; TEA domain-containing factors, transcriptional enhancer factors 1,3,4,5; Basonuclin, cooperates with UBF1 in rDNA PolI transcription; c-Rel; NF-kappaB; Zinc finger protein 410, APA-1; Tax/CREB complex; NF-kappaB; NUDR (nuclear DEAF-1 related transcriptional regulator protein); Pancreatic and intestinal lim-homeodomain factor; Cone-rod homeobox-containing transcription factor; TEF-1 related muscle factor; Alpha (1)-fetoprotein transcription factor (FTF), liver receptor homologue-1 (LRH-1); Y box binding protein 1, has a preference for binding ssDNA; GATA-binding factor 1; Cone-rod homeobox-containing transcription factor/otx-like homeobox gene; Pal3 motif, bound by a PPAR-gamma homodimer, IR3 sites; H6 family homeobox 1/NKXS-3; Fkh-domain factor FKHRL1 (FOXO); B-cell CLL/lymphoma 6, member B (BCL6B); Hmx2/Nkx5-2 homeodomain transcription factor; Hmx2/Nkx5-2 homeodomain transcription factor; Signal transducers and activators of transcription; Myeloid zinc finger protein MZF1; GABP: GA binding protein; Initiator (INR) and downstream promoter element (DPE) with strictly maintained spacing; NUDR (nuclear DEAF-1 related transcriptional regulator protein); Interferon regulatory factor 7 (IRF-7); Nuclear factor of activated T-cells 5; NMP4 (nuclear matrix protein 4)/CIZ (Cas-interacting zinc finger protein); Zinc finger transcription factor GLI1; Sp4 transcription factor; T-cell leukemia homeobox 1; Pdx1 (IDX1/IPF1) pancreatic and intestinal homeodomain TF; Brn-5, POU-VI protein class (also known as emb and CNS-1); Cart-1 (cartilage homeoprotein 1); *Xenopus* homeodomain factor Xvent-2; early BMP signaling response; Hepatic nuclear factor 1; pancreatic and intestinal lim-homeodomain factor; Pdx1 (IDX1/IPF1) pancreatic and intestinal homeodomain TF; Barx2, homeobox transcription factor that preferentially binds to paired TAAT motifs; NK6 homeobox 1; Zinc finger transcription factor OVO homolog-like 1; Hepatocyte nuclear factor 1 alpha (Tcf-1); v-Myb, variant of AMV v-myb; signal transducers and activators of transcription; TEA domain-containing factors, transcriptional enhancer factors 1,3,4,5; c-Rel, and any combination thereof.

In some embodiments, the miR-204 antagonist can comprise consist essentially of or consist of an oligonucleotide that binds to and inhibits or reduces the expression and/or activity of miR-204 or pre-miR-204.

An oligonucleotide of this invention can comprise one or more modified bases, modified sugar groups, modified phosphate groups, modified nucleoside linkages, terminal modifications, or any combination thereof. In some embodiments, the oligonucleotide can comprise at least one internucleoside phosphodiester linkage, at least one modified sugar moiety and a terminal lipid moiety.

In some embodiments, the oligonucleotide of this invention consists or consists essentially of about 15 to about 30 nucleotides and the oligonucleotide comprises, at any location within the about 15 to about 30 nucleotides of the oligonucleotide, a region of (e.g., of 4, 5, 6 or 7) contiguous nucleotides that are complementary to the seed sequence of miR-204 (CCUUUCC) or complementary to a sequence having at least 70% (e.g., 70%, 85%, 100%) identity with the seed sequence of miR-204, wherein each nucleotide of said region of contiguous nucleotides is, in any combination, unmodified or comprises a modified nucleoside linkage (e.g., phosphorothioate, methyl phosphonate, phosphoramidate, and any combination thereof), and/or a modified sugar moiety (e.g., 2'-O-methyl sugar moiety, 2'-F sugar moiety, 2'-O-methoxyethyl sugar moiety, bicyclic sugar moiety, $2'N_3$ sugar moiety, 4'thio sugar moiety, $NH_2$ sugar moiety, and any combination thereof), and wherein each of the remaining nucleotides of the about 15 to about 30 nucleotide long oligonucleotide is nucleotide X, wherein X can be A, U, C or G in any combination in the nucleotide sequence of the oligonucleotide and wherein, in any combination among the Xs of the oligonucleotide, X is not modified or X comprises a modified nucleoside linkage (e.g., phosphorothioate, methyl phosphonate, phosphoramidate, and any combination thereof), and/or a modified sugar moiety (e.g., 2'-O-methyl sugar moiety, 2'-F sugar moiety, 2'-O-methoxyethyl sugar moiety, bicyclic sugar moiety, 2'$N_3$ sugar moiety, 4'thio sugar moiety, $NH_2$ sugar moiety, and any combination thereof).

In various embodiments of the oligonucleotides of this invention, at least one (e.g., 1, 2, 3, 4, 5, 6, 7, etc.) nucleotide in the region of complementary nucleotides is modified as described herein and/or at least one of the nucleotides X is modified as described herein. Furthermore, in various embodiments of the oligonucleotides of this invention, at least one (e.g., 1, 2, 3, 4, 5, 6, 7, 8, 9, 10, 11, 12, 13, 14, 15, 16, 17, 18, 19, 20, 21, 22, etc.) of the nucleotides X is modified as described herein.

In one embodiment, the present invention provides an oligonucleotide that consists of or consists essentially of about 15 to about 30 nucleotides, wherein the oligonucleotide comprises at least about 15 of the nucleotides of the nucleotide sequence of SEQ ID No:1: 5' AGGCAUAGGAUGA-CAAAGGGAA 3' or a nucleotide sequence having at least 90% identity (e.g., at least 50%, 60%, 70%, 80%, 90%, 95%. 97%, 98%, 99% identity) with the nucleotide sequence of SEQ ID NO:1, wherein each nucleotide of the nucleotide sequence of SEQ ID NO:1 independently is not modified, or independently comprises a modified nucleoside linkage (e.g., phosphorothioate, methyl phosphonate, phosphoramidate, and any combination thereof), and/or a modified sugar moiety (e.g., 2'-O-methyl sugar moiety, 2'-F sugar moiety, 2'-O-methoxyethyl sugar moiety, bicyclic sugar moiety, 2'$N_3$ sugar moiety, 4'thio sugar moiety, $NH_2$ sugar moiety and any combination thereof). In some embodiments, the following oligonucleotide: 5'mA(*)mG(*)mGmCmAmUmAmGmGmA-mUmGmAmCmAmAmAmGmG(*)mG(*)mA(*)mA (*)mA(*)-3' [SEQ ID NO:36, wherein m means 2'-O-methyl modified and (*) means a phosphorothioate backbone modification] is included among the oligonucleotides of this invention and in some embodiments, this oligonucleotide is excluded (i.e., provisoed out) of the oligonucleotides of this invention.

In various embodiments of this invention, the oligonucleotide can comprise a terminal lipid moiety (e.g., a neutral lipid such as DSPC, DDPC, DMPC, POPC, DOPE, SM; a sterol, such as cholesterol; a polyalkylene glycol such as polyethylene glycol (PEG), a PEG-modified lipid, a targeting lipid such as N-acetyl-galactosamide and a folate containing lipid, and any combination thereof) at the 5' terminus, the 3' terminus or both the 5' terminus and the 3' terminus of the oligonucleotide.

In yet further embodiments, the oligonucleotide of this invention can be associated with a lipid based carrier system (e.g., pH sensitive liposome, immunoliposome, fusogenic liposome, cationic liposome, cationic lipid/antisense aggregate, and any combination thereof).

In some embodiments, the oligonucleotide can comprise a replacement group for phosphate and/or hydroxyl of the nucleotide at the 5' terminus of the oligonucleotide, the 3' terminus of the oligonucleotide or both the 5' and 3' termini of the oligonucleotide. Nonlimiting examples of such a replacement group include but are not limited to, biotin, an amino group, a lower alkylamine group, an acetyl group, 2'oxygenmethyl (2'-O-Me), 4,4'-dimethoxytrityl with oxygen (DMTO), fluoroscein, a thiol, acridine, and any combination thereof.

In addition, in some embodiments, the present invention provides a method of decreasing insulin production in a cell that produces insulin, comprising contacting the cell with a microRNA-204 (miR-204) mimic, thereby decreasing insulin production in the cell. Such a cell can be in a subject or in a cell culture, as described above for cells of this invention. A nonlimiting example of a cell of this method is an insulinoma cell.

A miR-204 mimic of this invention can be, for example an oligonucleotide having the nucleotide sequence: UUCCCU-UUGUCAUCCUAUGCCU (SEQ ID NO:2) and its complement, such that the mimic functions as a double stranded molecule. Additional examples of an miR-204 mimic of this invention include any double stranded oligonucleotide comprising the seed sequence of miR-204 anywhere throughout the oligonucleotide sequence and consisting of about 7 to about 50 nucleotides, X, wherein X can be A, C, U or G in any combination and including within the about 7 to about 50 nucleotides, the contiguous nucleotide sequence UUC-CCUUU (i.e., the seed sequence of miR-204).

Additionally provided herein is an isolated nucleic acid molecule comprising, consisting essentially of or consisting of about 15 to about 30 nucleotides, wherein the oligonucleotide comprises at least about 15 contiguous nucleotides of the nucleotide sequence of SEQ ID NO:2: 5' UUCCCUUU-GUCAUCCUAUGCCU 3', or a nucleotide sequence having at least 90% identity with the nucleotide sequence of SEQ ID NO:2, wherein each nucleotide of the nucleotide sequence of SEQ ID NO:2 independently is not modified, or independently comprises a modified nucleoside linkage (e.g., phosphorothioate, methyl phosphonate, phosphoramidate, and any combination thereof), and/or a modified sugar moiety (e.g., 2'-O-methyl sugar moiety, 2'-F sugar moiety, 2'-O-methoxyethyl sugar moiety, bicyclic sugar moiety, 2'$N_3$ sugar moiety, 4'thio sugar moiety, $NH_2$ sugar moiety and any combination thereof).

A further embodiment of the present invention provides a composition comprising a nucleic acid molecule (e.g., an oligonucleotide) of this invention and a pharmaceutically acceptable carrier. By "pharmaceutically acceptable carrier" is meant a carrier that is compatible with other ingredients in the pharmaceutical composition and that is not harmful or deleterious to the subject. The carrier can be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients.

The compositions of this invention can be used, for example, in the production of a medicament for the use in treatment of a disease and/or disorder as described herein.

The compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, intraocular or intravenous), topical (i.e., both skin and mucosal surfaces, including airway surfaces) and transdermal administration, although the most suitable route and dosage intervals in any given case will depend, as is well known in the art, on such factors as the species, age, gender and overall condition of the subject, the nature and severity of the condition being treated and/or on the nature of the particular composition (i.e., dosage, formulation, mode of administration) that is being administered. In some embodiments, the composition of this invention can be administered to a subject as an eye drop solution and/or via injection into the eye.

An "effective amount" of a compound of this invention refers to a nontoxic but sufficient amount to provide a desired therapeutic effect. An appropriate "effective" amount in any individual case can be determined by one of ordinary skill in the art by reference to the pertinent texts and literature (e.g., Remington's Pharmaceutical Sciences (latest edition) and/or by using routine pharmacological procedures.

The formulation of therapeutic compounds and compositions of the invention and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the subject. Persons of ordinary skill can easily determine optimum dosages, dosing methodologies and repetition rates. Optimum dosages may vary depending on the relative potency of individual oligonucleotides or other antagonists, and can generally be estimated based on $EC_{50}$s found to be effective in in vitro and in vivo animal models.

Nonlimiting examples of dosage ranges of the compositions and oligonucleotides of this invention can be from about 0.01 µg to about 100 g per kg of body weight, from about 0.1 µg to about 10 g per kg of body weight, from about 1.0 µg to about 1 g per kg of body weight, from about 10.0 µg to about 100 mg per kg of body weight, from about 100 µs to about 10 mg per kg of body weight, or from about 1 mg to about 5 mg per kg of body weight, and may be given once or more daily, weekly, monthly or yearly, including over the lifetime of the subject. Persons of ordinary skill in the art can easily determine repetition rates for dosing based on measured residence times and concentrations of the drug in bodily fluids or tissues.

The effects of treatments with therapeutic compositions of this invention can be assessed following collection of tissues or fluids from a subject receiving such treatments. It is known in the art that a biopsy sample can be obtained from certain tissues without resulting in detrimental effects to a subject. In certain embodiments, a tissue and its constituent cells can comprise, but are not limited to, blood (e.g., hematopoietic cells, such as human hematopoietic progenitor cells, human hematopoietic stem cells, $CD34^+$ cells, $CD4^+$ cells), lymphocytes and other blood lineage cells, bone marrow, breast, cervix, colon, esophagus, lymph node, muscle, peripheral blood, oral mucosa and skin. In other embodiments, a fluid and its constituent cells can comprise, but are not limited to, blood, urine, semen, synovial fluid, lymphatic fluid and cerebrospinal fluid. Tissues or fluids obtained from a subject can be evaluated for expression levels of a target small non-coding RNA, mRNA and/or protein. Additionally, the mRNA or protein expression levels of other genes known or suspected to be associated with the specific disease state, condition or phenotype can be assessed. mRNA levels can be measured or evaluated by real-time PCR, Northern blot, in situ hybridization and/or DNA array analysis.

"Treat" or "treating" as used herein refers to any type of action or implementation that imparts a benefit to a subject that is diagnosed with, at risk of having, suspected to have and/or likely to have a disease or disorder that can be responsive in a positive way to a compound of this invention. A benefit can include an improvement in the condition of the subject (e.g., in one or more symptoms), and/or delay and/or reversal in the progression of the condition, etc.

The examples below are set forth to illustrate the present invention, and are not to be construed as limiting thereof.

EXAMPLES

Example 1

Thioredoxin-Interacting Protein Regulates Insulin Transcription Through microRNA-204

Insulin production in pancreatic beta cells is a prerequisite for maintaining normal glucose homeostasis. In fact, beta cell dysfunction and impaired insulin production are hallmarks of diabetes[1-3], but despite the growing diabetes epidemic worldwide the molecular mechanisms involved have only begun to be elucidated. thioredoxin-interacting protein (TXNIP), a cellular redox regulator, has been identified as a factor involved in beta cell biology and it has been shown that beta cell TXNIP was upregulated in diabetes, whereas TXNIP deficiency protected against diabetes by preventing beta cell apoptosis[4,5].

Here it is shown that TXNIP and diabetes induce beta cell expression of a specific microRNA, miR-204, which in turn blocks insulin production by directly targeting and downregulating MafA, a known insulin transcription factor. After the discovery was made that miR-204 is induced by TXNIP in a microRNA microarray analysis, the regulation of this microRNA by TXNIP and diabetes was confirmed using INS-1 beta cells, islets of TXNIP-deficient mice, diabetic mouse models and primary human islets. Moreover, using 3'UTR luciferase assays, MafA was identified as a novel target of miR-204, its downregulation was confirmed and it was shown that miR-204 and TXNIP decrease MafA binding to the insulin promoter and inhibit insulin production. This indicates that this novel TX'123NIP/miR-204/MafA/insulin pathway may contribute to the pathogenesis of diabetes and the associated impairment in insulin production.

Taken together, these studies demonstrate that TXNIP controls microRNA expression and insulin production, that a microRNA inhibits human insulin transcription and that miR-204 is involved in pancreatic beta cell function. As such these results provide major advances in understanding TXNIP function, microRNA biology and insulin production as well as the molecular mechanisms governing these key biological processes in health and disease.

MicroRNAs (small, 20-24 nucleotide, non-coding RNAs) recognize and bind to target mRNAs through imperfect base pairing leading to destabilization or translational inhibition of the target mRNA and downregulation of target gene expression[12,13].

Figure 1:
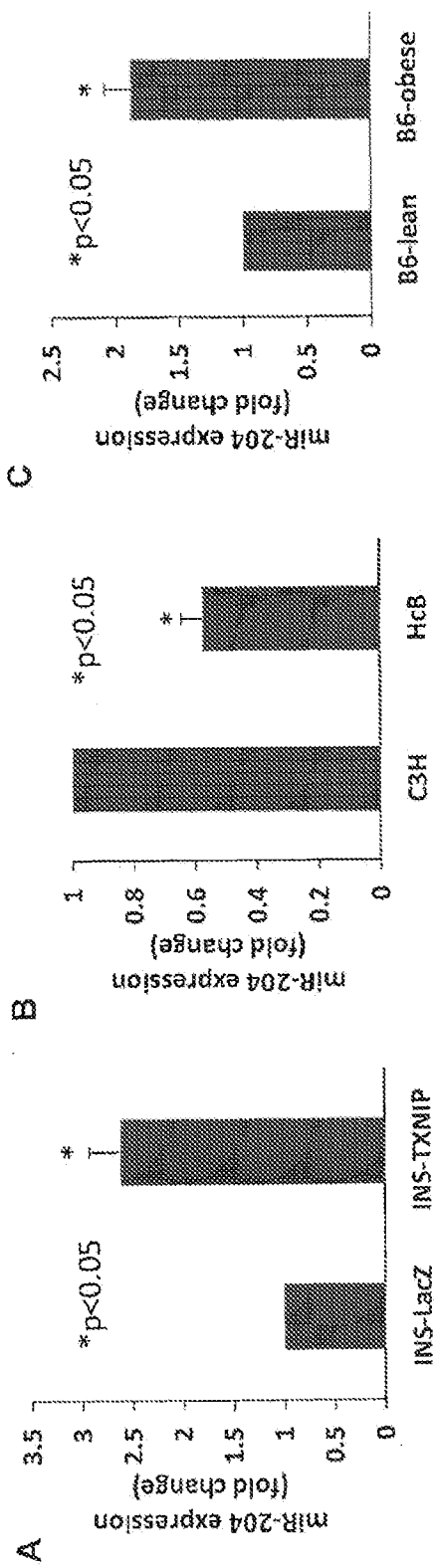
FIG. 1. Effects of TXNIP and diabetes on beta cell miR-204 expression. Expression of miR-204 was assessed by qRT-PCR in (A) INS-1 cells overexpressing TXNIP (INS-TXNIP) and control (INS-LacZ) cells, (B) primary islets of TXNIP-deficient HcB-19 and C3H control mice and (C) primary islets of 10-week old, male, diabetic ob/ob or lean control mice. Bars represent means±SEM; n=3-5.
Figure 6:
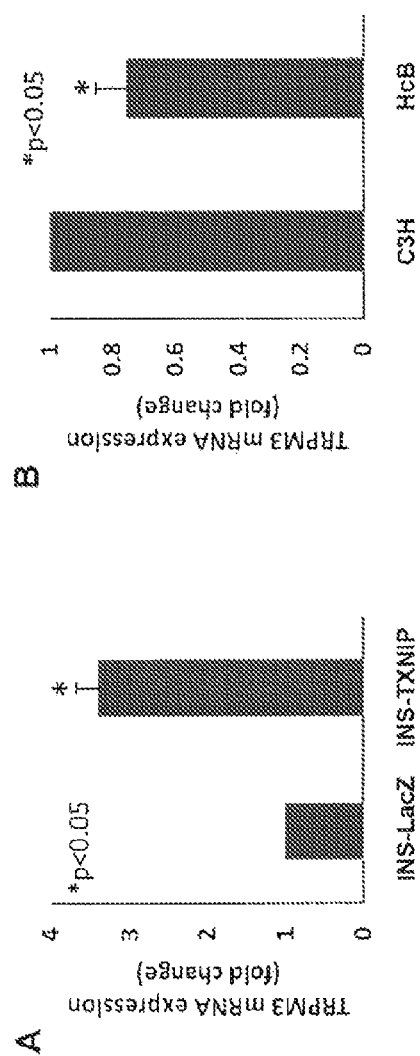
FIG. 6. TXNIP effects on TRPM3 expression. The expression of TRPM3 was assessed by qRT-PCR in (A) TXNIP overexpressing INS-TXNIP and control INS-LacZ cells and (B) primary islets of TXNIP deficient HcB-19 and control C3H mice. Bars represent means±SEM, n=3.

Comparison of TXNIP overexpressing INS-1 beta cell line (INS-TXNIP) and an INS-LacZ control cell line using miR-CURY LNA microRNA Arrays (Exiqon) indicated that TXNIP induces beta cell expression of microRNA-204 (miR-204). To further determine the effects of TXNIP on miR-204 expression, the microarray findings were confirmed by quantitative real-time RT-PCR (qRT-PCR) and it was found that miR-204 expression was >2-fold higher in INS-TXNIP cells as opposed to control INS-LacZ cells (FIG. 1A). In contrast, primary islets from TXNIP-deficient HcB-19 mice (harbouring a natural nonsense mutation in the TXNIP gene) showed a significant reduction in miR-204 expression (FIG. 1B) further indicating that TXNIP regulates beta cell miR-204 expression.

miR-204 is encoded on chromosome 9q21.11 within intron 6 of the TRPM3 gene (transient receptor potential melastatin 3, a cation-selective channel) and is transcribed in the same direction as TRPM3[25]. It was found that TRPM3 expression was >3-fold higher in TXNIP overexpressing INS-TXNIP cells as opposed to control INS-LacZ cells (FIG. 6A), whereas primary islets from TXNIP-deficient HcB-19 mice showed a significant reduction in miR-204 expression (FIG. 6B). These findings are very similar to the results obtained for miR-204 and suggest that in fact, TXNIP upregulates miR-204 by inducing its transcription through the shared TRPM3/miR-204 promoter region.

Figure 7:
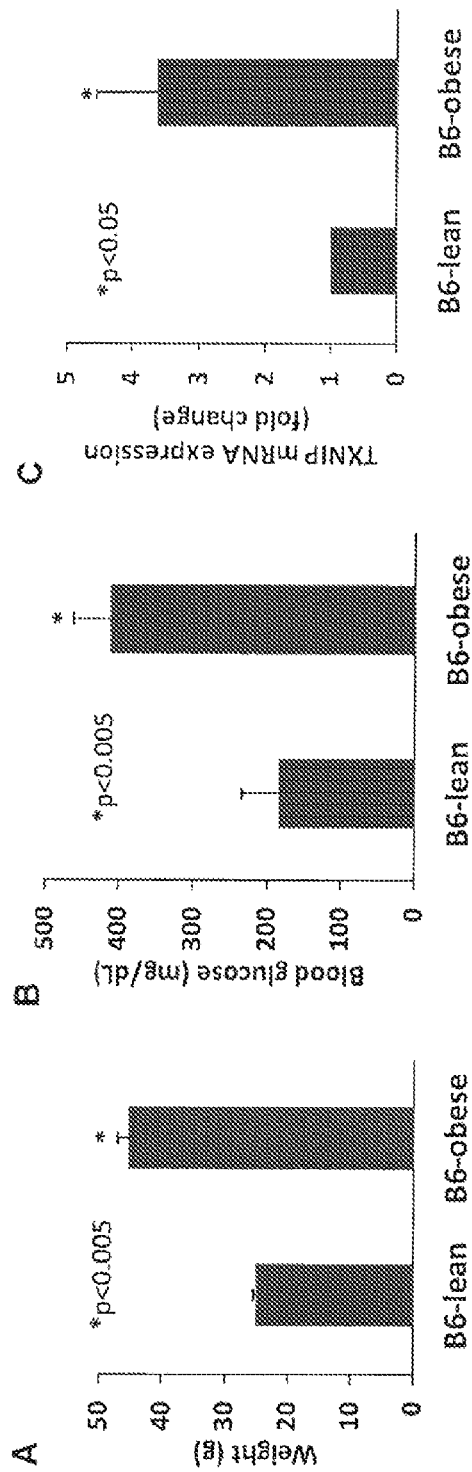
FIG. 7. (A) Weight, (B) blood glucose and (C) TXNIP mRNA expression in islets of diabetic B6 ob/ob and B6 lean control mice. Bars represent means±SEM, n=3.

Studies were done to determine whether beta cell miR-204 expression might also be altered in diabetes. To this end the leptin-deficient, obese and diabetic B6ob/ob mice were used as a model of type 2 diabetes (FIGS. 7A-B). Islets of obese and diabetic mice showed dramatically elevated TXNIP levels (FIG. 7C), consistent with previous findings in BTBRob/ob mice[5]. miR-204 expression was also significantly increased in diabetic ob/ob mice as opposed to lean control mice (FIG. 1C) suggesting that this microRNA might play a role in the beta cell dysfunction of diabetes.

Figure 2:
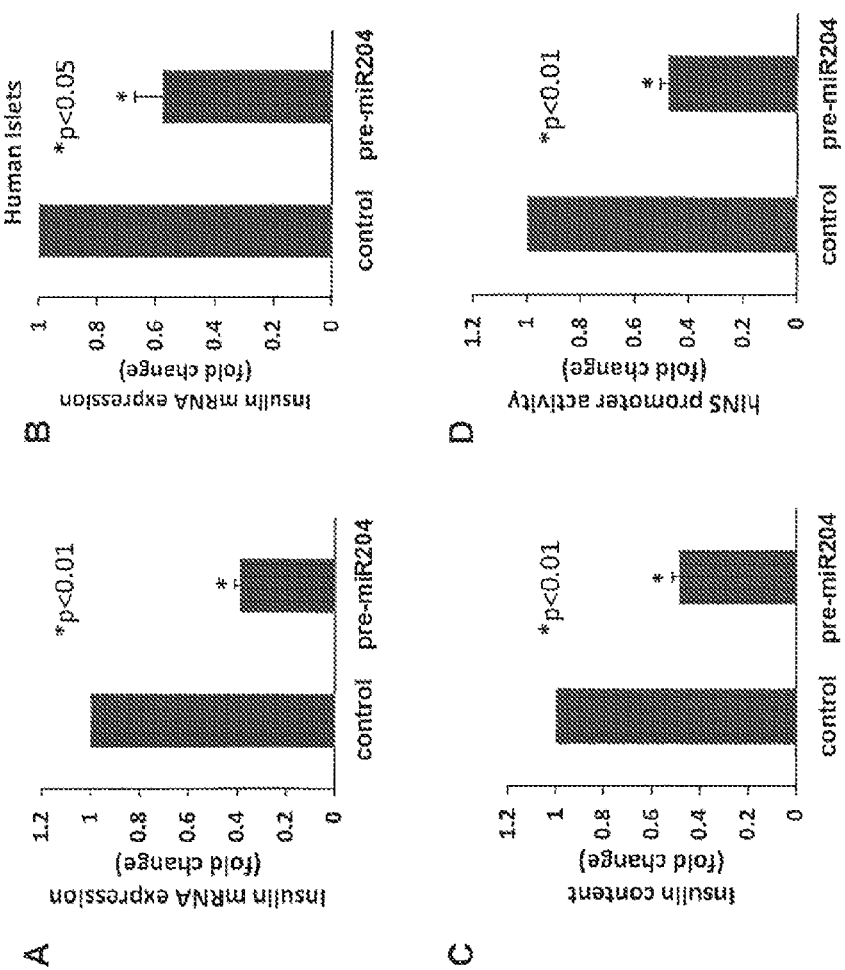
FIG. 2. miR-204 effects on insulin production. (A) INS-1 cells and (B) human islets were transfected with miR-204 precursor (pre-miR204) or scrambled control. 72 h after transfection, RNA was extracted and analysed for insulin mRNA by qRT-PCR. (C) Cellular insulin protein content in INS-1 cells overexpressing miR-204 or scrambled control was assessed by ELISA and normalized for cellular DNA content. (D) INS-1 cells were cotransfected with the human insulin promoter reporter construct Ins-Luc, and pre-miR204 or control plasmid. Cells were harvested 72 h after transfection, and insulin promoter activity was assessed by firefly luciferase (and corrected for transfection efficiency with pRL-TK renilla luciferase). Bars represent means±SEM of 3 independent experiments.

To start elucidating the unknown function of miR-204, studies were done to investigate the possibility that miR-204 might affect beta cell function, i.e., insulin production. miR-204 overexpression in INS-1 cells led to a >2-fold reduction in insulin mRNA expression (FIG. 2A). (Unlike humans, rodents have two insulin genes and while data shown was obtained with primers detecting expression from both rat insulin genes, primers specific for Ins1 or Ins2 showed the same effect.) In contrast, transfection of miR-204 inhibitor oligonucleotides not only resulted in effective inhibition of miR-204 (FIG. 8A), but also in a significant increase in insulin mRNA levels (FIG. 8B), suggesting that miR-204 regulates insulin gene expression. In human islets, miR-204 overexpression also decreased insulin mRNA similar to INS-1 cells (FIG. 2B), demonstrating that this effect was also relevant to human islet biology. In addition, this decrease in insulin mRNA expression translated at the protein level into significantly reduced insulin content in miR-204 overexpressing cells (FIG. 2C). It was surprisingly observed that miR-204 inhibited insulin promoter activity (FIG. 2D), rather than having classical post-transcriptional microRNA effects on mRNA stability or translation. This suggested that the effect was indirect and likely mediated by miR-204-induced downregulation of factor(s) involved in insulin transcription.

Figure 3:
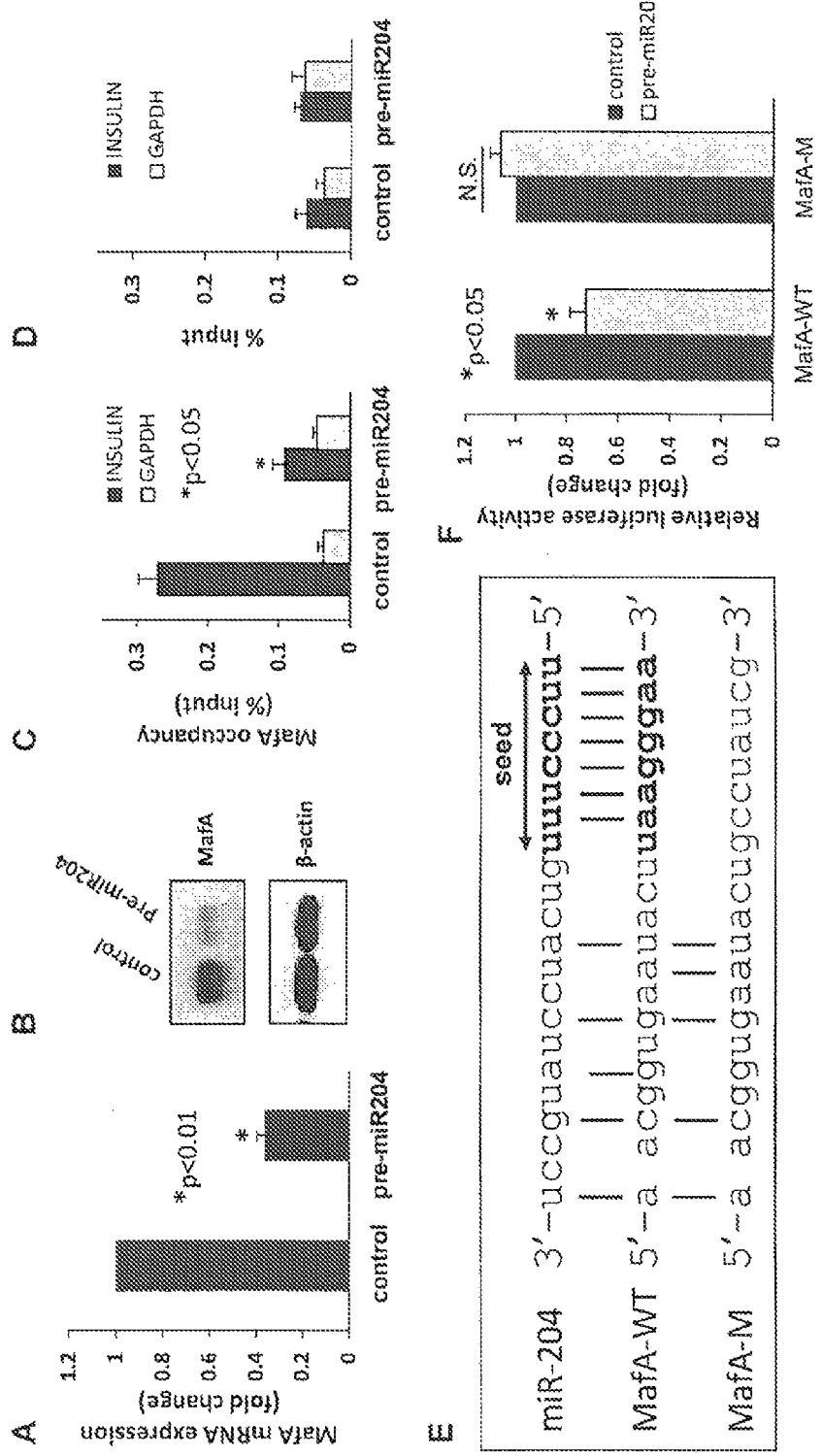
FIG. 3. MafA as a target of miR-204. miR-204 effects on MafA mRNA (A) or protein expression (B) as assessed by qRT-PCR and immunoblotting. (C) Changes in MafA occupancy of the insulin promoter in response to miR-204 as measured by ChIP; (D) IgG control. (E) Alignment of miR-204 (SEQ ID NO:33) seed sequence (arrow) and rat MafA 3'UTR (SEQ ID NO:34) target sequence (bold) as well as mutated (SEQ ID NO:35) target sequence (grey). (F) INS-1 cells were cotransfected with the wild-type MafA-WT-3'Luc or mutant MafA-M-3'Luc 3'UTR reporter plasmids and with miR-204 or scrambled control. 24 h after transfection, miR-204-directed repression of the luciferase reporter gene bearing the wild-type or mutant MafA 3'UTR segments was assessed. Bars represent means±SEM of three independent experiments and one representative immunoblot is shown.
Figure 8:
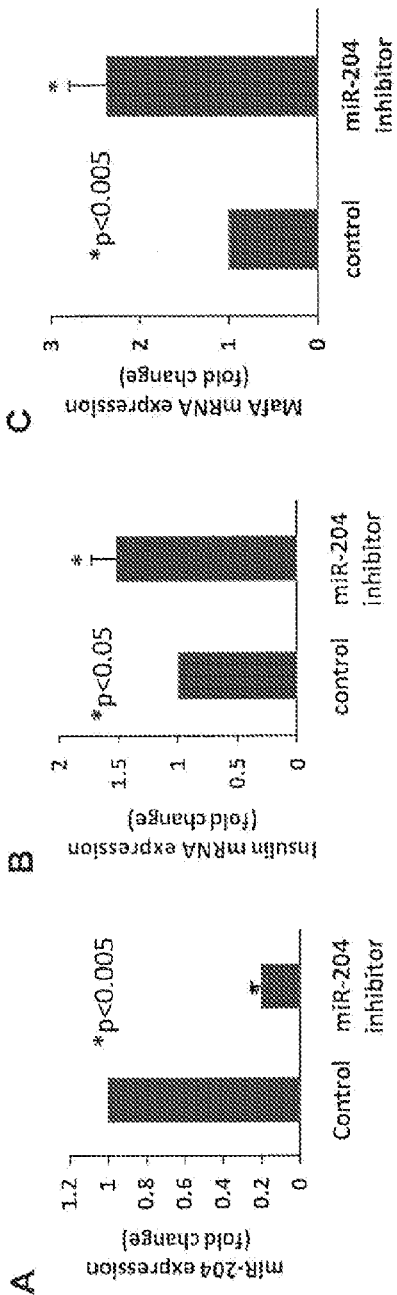
FIG. 8. Effects of miR-204 inhibition. INS-1 cells were grown in 6-well plates and transfected with miRIDIAN hairpin inhibitor rno-miR-204 or miRIDIAN microRNA hairpin inhibitor negative control at a final concentration of 25 nM (Dharmacon/Thermo Scientific) using DharmaFECT 1 transfection reagent. 48 h after transfection, cells were harvested and assessed by qRT-PCR for (A) miR-204 knock down efficiency, (B) insulin mRNA expression and (C) MafA mRNA expression. Bars represent means±SEM, n=3.
Figure 9:
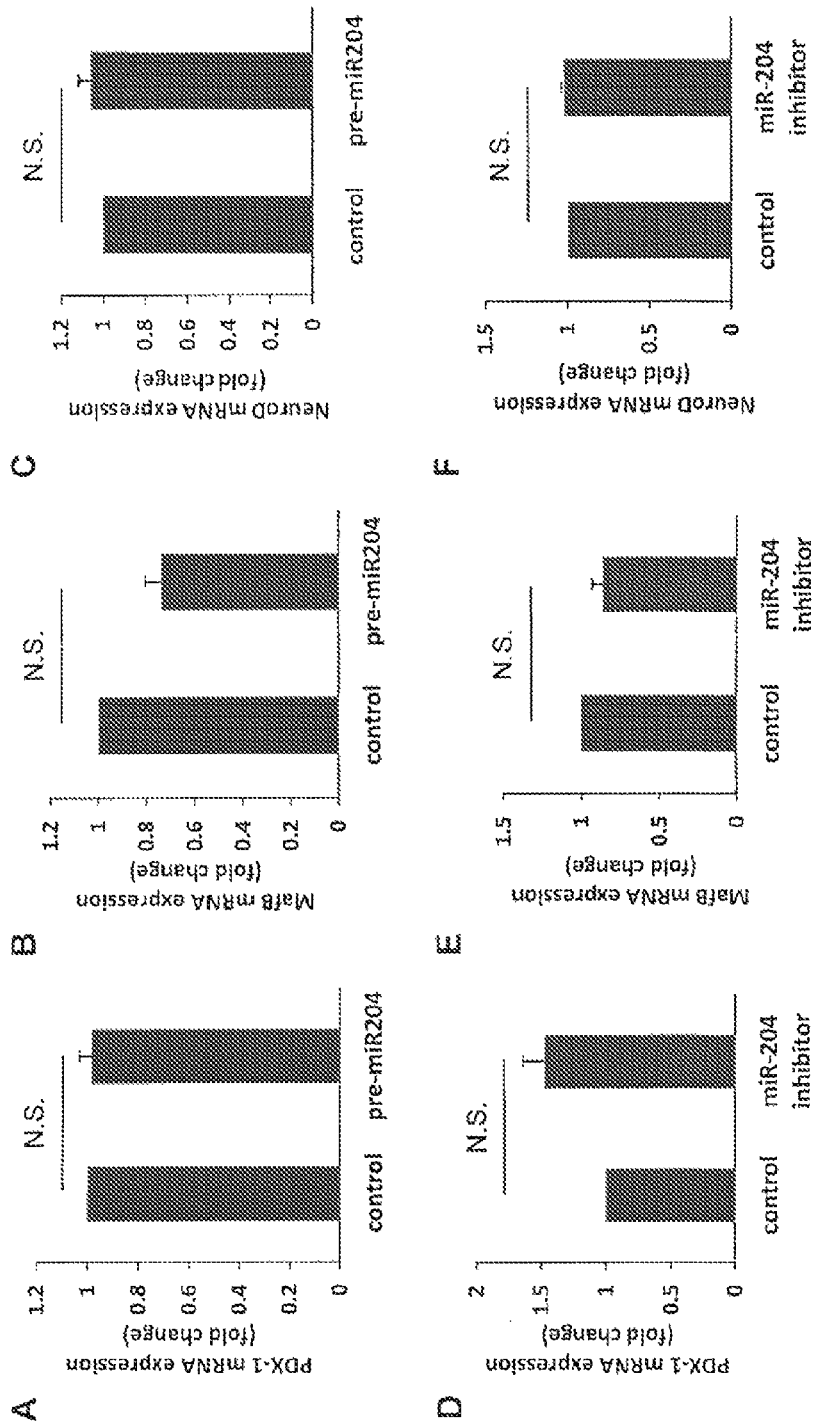
FIG. 9. Effects of miR-204 overexpression or inhibition on insulin transcription factors. INS-1 cells were transfected with pre-miR204 (A-C) or miR-204 inhibitor (D-F), harvested after 72 h or 48 h, respectively and analyzed by qRT-PCR for the expression of PDX-1 (A,D), MafB (B,E) and NeuroD (C,F). Bars represent means±SEM, n=3.

To identify these factors, studies were carried out to find the putative gene targets of miR-204 and especially those that might play a role in insulin transcription. Studies were undertaken to determine whether miR-204 could inhibit the expression of any of the key insulin transcription factors, i.e., MafA/B, NeuroD or PDX1[26-29]. MafA mRNA and protein levels were dramatically reduced in response to miR-204 (FIGS. 3A-B), whereas miR-204 inhibition led to a >2-fold increase in MafA expression (FIG. 8C). In contrast, the other transcription factors were not significantly altered by overexpression or inhibition of miR-204 (FIG. 9). In addition, this miR-204-induced reduction in MafA expression also resulted in dramatically reduced MafA binding to the insulin promoter as assessed by chromatin immunoprecipitation (ChIP) studies (FIGS. 3C-D). Together, these findings raised the possibility that MafA was acting as the miR-204 target mediating the effects of this microRNA on insulin gene expression. Comparison of the miR-204 seed sequence and the MafA 3'UTR revealed an almost perfect match (FIG. 3E), suggesting that MafA might be a target of miR-204. To address this question, reporter constructs were generated with the wild-type MafA 3'UTR or a mutated MafA 3'UTR (FIG. 3E) cloned downstream of the luciferase gene and miR-204-directed repression of the reporter gene was assessed. miR-204 significantly decreased luciferase levels through the wild-type MafA 3'UTR, while no reduction was found with the mutant 3'UTR (FIG. 3F), confirming that MafA is indeed a direct target of miR-204.

Figure 4:
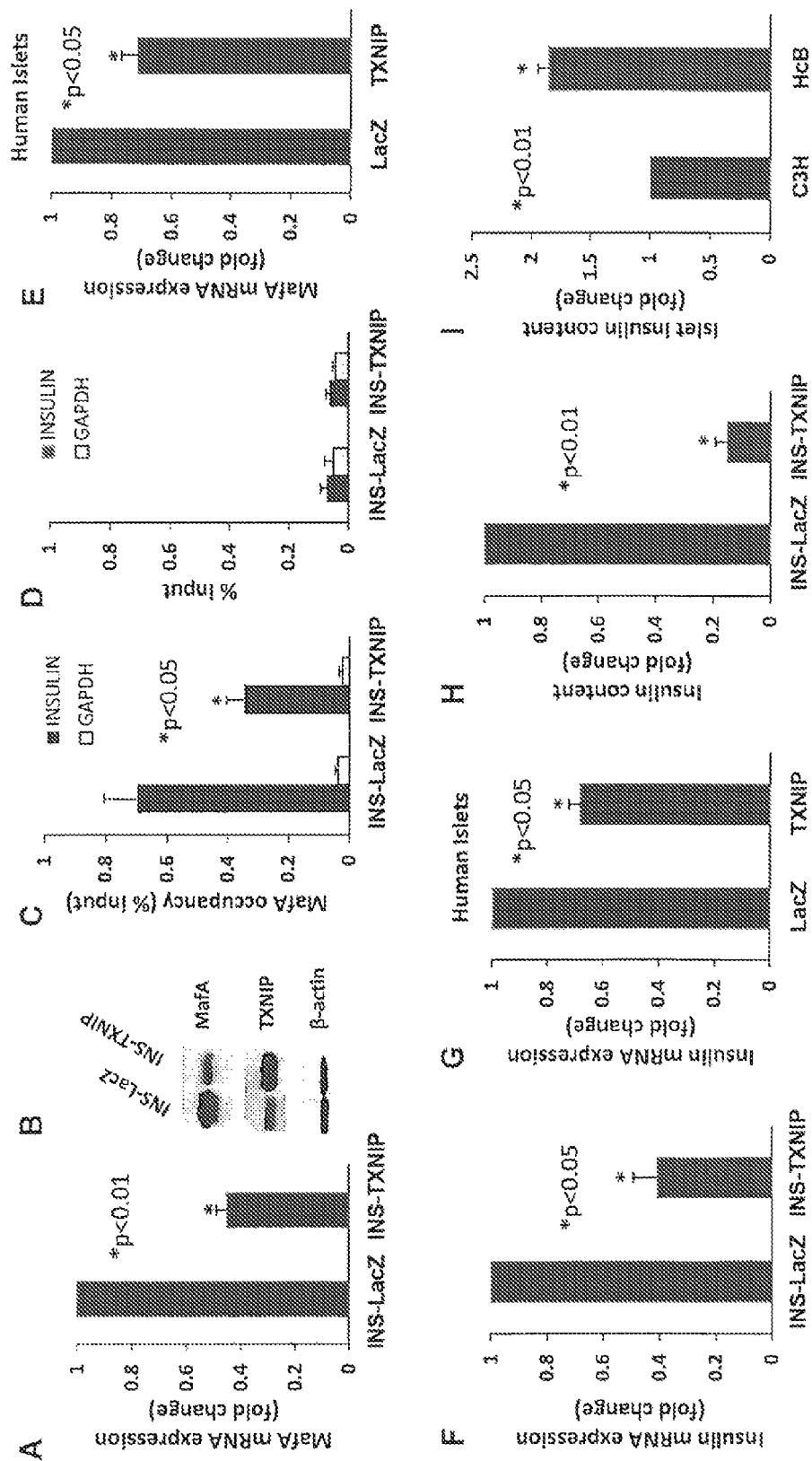
FIG. 4. TXNIP effects on MafA and insulin production. TXNIP overexpressing INS-TXNIP cells were analyzed for (A) MafA mRNA by qRT-PCR, (B) MafA protein by immunoblotting and (C) MafA occupancy of the insulin promoter by ChIP; (D) IgG control and compared to INS-LacZ control cells. (E) Human islets were transfected with CMV-hTXNIP or LacZ and the effects on MafA mRNA expression were assessed by qRT-PCR. Insulin mRNA as assessed by qRT-PCR in INS-TXNIP cells (F) and human islets transfected with TXNIP (G). Insulin content as assessed by ELISA in INS-TXNIP cells (H) and primary islets of TXNIP-deficient HcB-19 mice (I); n=3.
Figure 10:
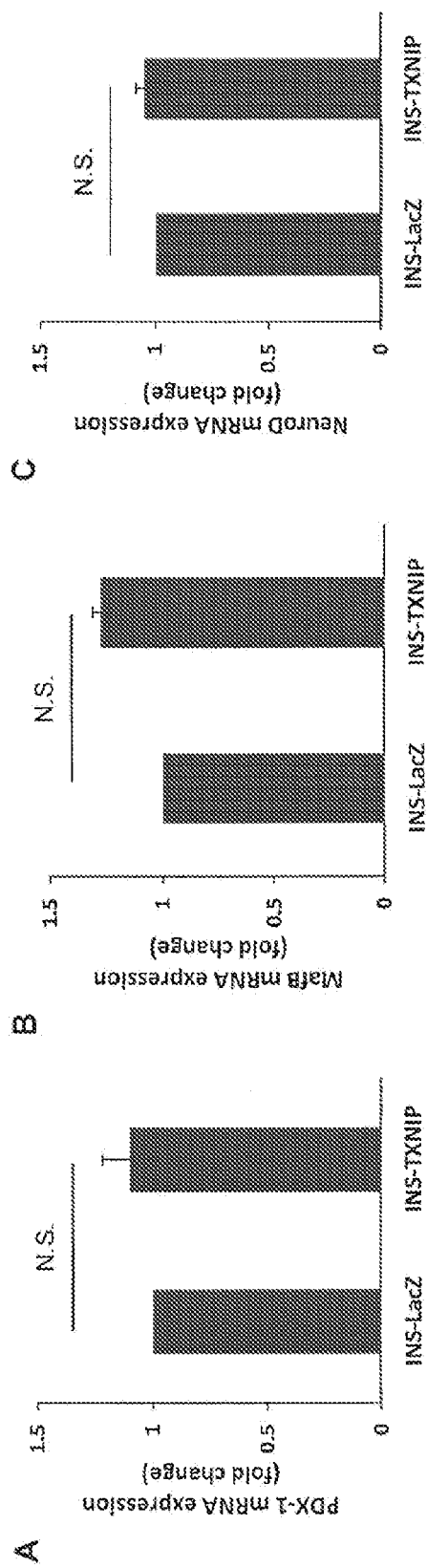
FIG. 10. TXNIP effects on insulin transcription factors. The expression of PDX-1 (A), MafB (B) and NeuroD (C) was assessed by qRT-PCR in TXNIP overexpressing INS-TXNIP and control INS-LacZ cells. Bars represent means±SEM, n=3.

To investigate whether TXNIP (as an upstream regulator of miR-204) could mimic the miR-204 effects on MafA, the TXNIP overexpressing INS-1 cell line was analyzed and a >2-fold reduction in MafA mRNA expression and MafA protein levels was found (FIG. 4A-B), similar to the results in response to direct miR-204 overexpression. In contrast, TXNIP had no effect on PDX-1, MafB or NeuroD expression levels (FIG. 10). In addition, ChIP analysis revealed that MafA occupancy of the insulin promoter was reduced to almost half in TXNIP overexpressing cells as compared to INS-LacZ control cells (FIGS. 4C-D). Moreover, TXNIP also reduced MafA expression in human islets (FIG. 4E), confirming the physiological relevance of these findings.

To further test whether TXNIP would also block insulin production similarly to miR-204, parallel experiments were conducted using TXNIP overexpressing INS-1 cells as well as human islets and TXNIP deficient HcB-19 mouse islets. TXNIP led to a significant decrease in insulin mRNA levels in INS-1 cells (FIG. 4F) and human islets (FIG. 4G) and at the protein levels caused a dramatic reduction in insulin content (FIG. 4H). In contrast, TXNIP deficient islets demonstrated a highly significant, 2-fold increase in insulin content (FIG. 4I), strongly supporting the notion that TXNIP inhibits beta cell insulin production through induction of miR-204 expression.

Figure 11:
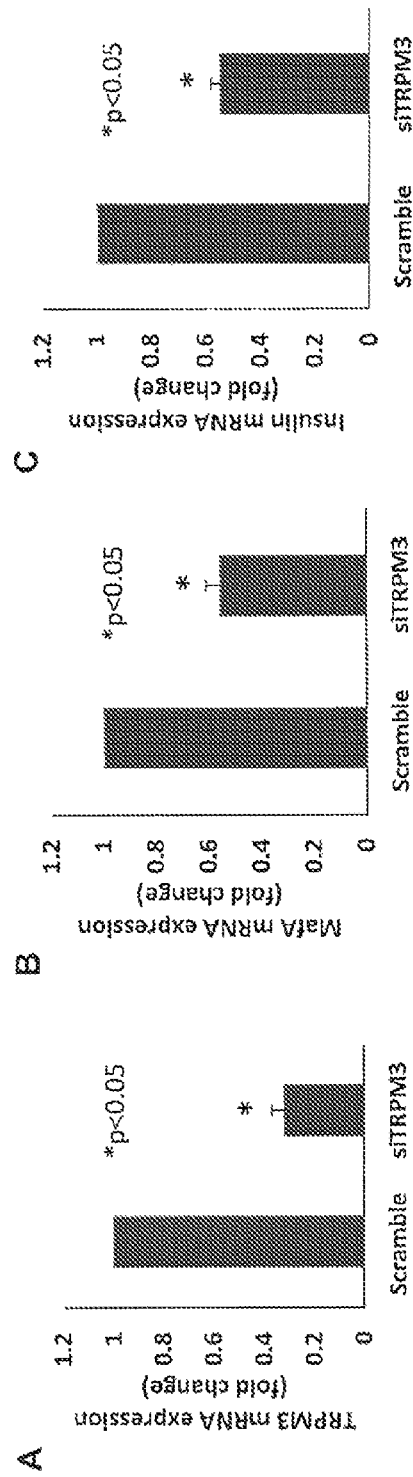
FIG. 11. Effects of TRPM3 knock down on MafA and insulin expression. INS-1 cells were transfected with siTRPM3 or scrambled oligonucleotides, harvested after 48 h, and analyzed by qRT-PCR for the expression of (A) TRPM3, (B) MafA and (C) insulin. Bars represent means±SEM, n=3.

TRPM3 was knocked down using siRNA and studies were conducted to assess whether this could mimic the effects of miR-204 inhibition. However, while a robust downregulation of TRPM3 was obtained (FIG. 11A), neither MafA (FIG. 11B) nor insulin expression (FIG. 11C) were increased, and in contrast to miR-204 inhibition, were rather decreased. This indicates that TRPM3 is not conferring the observed TXNIP-mediated regulation of insulin transcription. Moreover, it suggests that miR-204 is not only able to regulate insulin transcription as demonstrated by miR-204 overexpression and inhibition, but in the case of TXNIP overexpression, also to outweigh the opposing effects of TRPM3.

Figure 5:
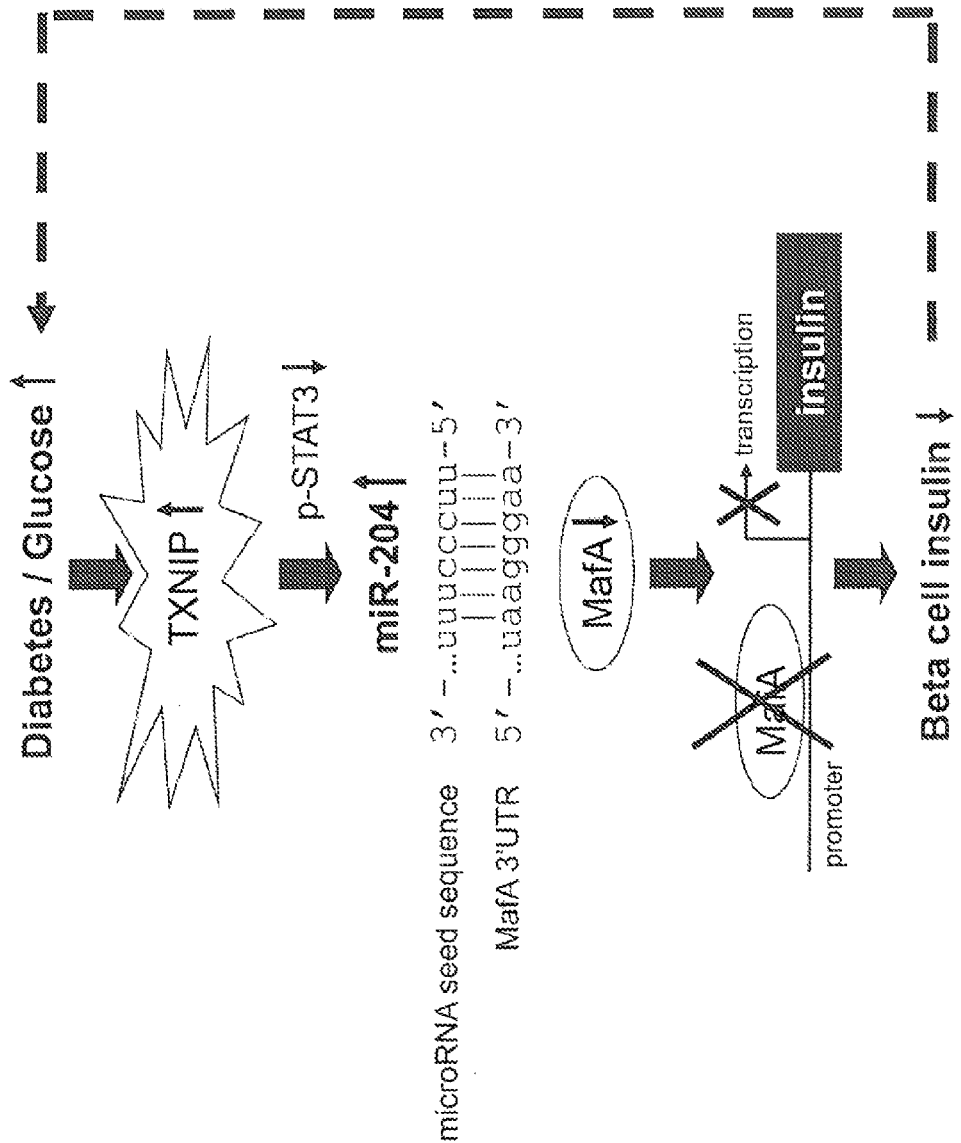
FIG. 5. Schematic summary of the TXNIP/miR-204/MafA/insulin pathway.

Taken together, these findings in INS-1 beta cells, islets of TXNIP-deficient mice, diabetic mouse models and primary human islets demonstrate that TXNIP and diabetes induce beta cell transcription of a specific microRNA, miR-204, which in turn blocks insulin production by directly targeting and downregulating the critical transcription factor, MafA. This indicates that this novel TXNIP/miR-204/MafA/insulin pathway may contribute to impaired insulin production, beta cell dysfunction and the pathogenesis of diabetes (FIG. 5).

The discovery that miR-204 is upregulated in diabetes and controls insulin transcription reveals a potential novel target for the development of RNA therapeutics that would address an unmet need for increasing insulin production.

Tissue culture. INS-1 beta-cells and stably transfected INS-TXNIP overexpressing human TXNIP or control INS-LacZ cells were grown as previously described[8]. Mouse pancreatic islets were isolated by collagenase digestion as detailed previously[4]. Human islets were obtained from the UAB Islet Resource Facility.

Animal studies. All mouse studies were approved by the University of Alabama at Birmingham Animal Care and Use Committee and conform to the NIH Guide for the Care and Use of Laboratory Animals. The C3H congenic TXNIP-deficient HcB-19 (HcB) mice harboring a naturally occurring nonsense mutation in the TXNIP gene and the control C3H/DiSnA (C3H) strain have been described previously[5]. Male, 1-year old animals were used for the studies shown, but results were also confirmed in younger, 4-month old male mice.

Plasmid construction and transfection assays. The TXNIP expression plasmid has been described previously[8], construction of Ins-Luc, MafA-WT-3'Luc or MafA-M-3'Luc and transfection assays are described herein.

Quantitative real-time RT-PCR. qRT-PCR was performed as described previously[5] using a Lightcycler 480 system (Roche, Indianapolis, Ind.) and the primers listed in Table 1. miR-204 expression was quantified using a TaqMan microRNA Assay (Applied Biosystems). Gene and microRNA expression results were corrected for 18S and U6 run as internal standards, respectively.

Immunoblotting. Protein extracts were prepared and analysed as described previously[4]. MafA was detected by Rabbit anti-MafA (sc-66958X, Santa Cruz Biotechnology, Santa Cruz, Calif.).

Insulin content. Insulin content of isolated islets and INS-1 cells was assessed by ELISA and normalized for DNA content as described previously[4] and detailed as described herein, respectively.

Chromatin immunoprecipitation (ChIP). ChIP assays were performed as described previously[32]. 5 μg of rabbit anti-MafA (A300-611A, Bethyl Laboratories, Montgomery, Tex.) or normal rabbit IgG (sc-2027, Santa Cruz) were used for immunoprecipitation and purified DNA fragments were quantified by qPCR with primers described in Table 1.

Statistical analysis. Student's t-tests or ONE-WAY-ANOVA were used to calculate the significance of a difference between two or more groups, respectively Plasmid construction, transfection and luciferase assays. The human insulin promoter region was amplified from genomic DNA with primers from Table 1 and subcloned into the MluI and HindIII restriction sites of the pGL3 enhancer vector (Promega, Madison, Wis.) providing the Ins-Luc reporter plasmid. The wild-type MafA 3'UTR region was amplified from rat genomic DNA. To generate the rat MafA mutant reporter plasmid, 8-bp mutations were introduced by two rounds of PCR and the primers listed in Table 1. PCR products were subcloned into the SpeI and PmeI sites of the pMIR-REPORT Luciferase vector (Applied Biosystems, Foster City, Calif.) yielding the MafA-WT-3'Luc and MafA-M-3'Luc 3'UTR reporter plasmids. All plasmids were confirmed by sequencing. For transfection experiments, INS-1 cells were plated in 6-well plates and grown overnight to ~60% confluence. Human islets (500 per tube) were gently dispersed by incubation for 5 minutes in 200 ml of 0.05% Trypsin-EDTA (Invitrogen, Grand Island, N.Y.) at 37° C. washed and resuspended in culture medium. Cells were transfected with hsa-miR-204 precursor or pre-miR negative control 2 (Applied Biosystem) at a final concentration of 25 nM using DharmaFECT1 transfection reagent (Dharmacon/Thermo Scientific, Chicago, Ill.). For luciferase assays, INS-1 cells were grown overnight in 12-well plates and cotransfected with Ins-Luc, MafA-WT-3'Luc or MafA-M-3'Luc and hsa-miR-204 or negative control using Dharma-FECTDuo transfection reagent (Dharmacon/Thermo Scientific), To control for transfection efficiency, cells were cotransfected with pRL-TK (Promega) control plasmid expressing renilla luciferase and firefly as well as renilla luciferase activity were determined using the Dual Luciferase Assay Kit (Promega).

Insulin content. INS-1 cells were plated in 24-well plates and after overnight incubation at 5 mM glucose the medium was removed and cells were incubated in KRB buffer with 2.5 mM glucose (135 mM NaCl, 3.6 mM KCl, 10 mM Hepes [pH 7.4], 5 mM NaHCO$_3$, 0.5 mM NaH$_2$PO$_4$, 0.5 mM MgCl$_2$, 1.5 mM CaCl$_2$) for 1 hr. After stimulation with KRB buffer containing 16.7 mM of glucose for 1 hr, cells were lysed with 300 μl lysis buffer (100 mM Tris-HCl [pH 8.0], 300 mM NaCl, 10 mM NaCl, 2 mM NaOrthovanadate, 2% NP-40, 2 Protease cocktail tablets [Roche]) and lysates stored overnight at −20° C. After centrifugation at 5000 rpm for 5 min, the supernatants were harvested for insulin assay with the Ultra Sensitive Rat Insulin ELISA Kit (Crystal Chem Inc., Downers Groves, Ill.). Results were normalized for DNA content as determined by Quant-iTPicoGreendsDNA Assay kit (Invitrogen).

References for Example 1

1. Lawrence, M. C., McGlynn, K., Park, B. H. & Cobb, M. H. ERK1/2-dependent activation of transcription factors required for acute and chronic effects of glucose on the insulin gene promoter. *J Biol Chem* 280, 26751-9 (2005).
2. Khoo, S. et al. MAP Kinases and Their Roles in Pancreatic beta-Cells. *Cell Biochem Biophys* 40, 191-200 (2004).
3. Poitout, V. & Robertson, R. P. Minireview: Secondary beta-cell failure in type 2 diabetes—a convergence of glucotoxicity and lipotoxicity. *Endocrinology* 143, 339-42 (2002).
4. Chen, J., Saxena, G., Mungrue, I, N., Lusis, A. J. & Shalev, A. Thioredoxin-Interacting Protein: A Critical Link between Glucose Toxicity and Beta Cell *Apoptosis. Diabetes* 57, 938-944 (2008).
5. Chen, J. et al. Thioredoxin-Interacting Protein Deficiency Induces Akt/Bcl-xL Signaling and Pancreatic Beta Cell Mass and Protects Against Diabetes. *FASEB J* 22, 3581-3594 (2008).
6. Nishiyama, A., Masutani, H., Nakamura, H., Nishinaka, Y. & Yodoi, J. Redox regulation by thioredoxin and thioredoxin-binding proteins. *IUBMB Life* 52, 29-33 (2001),
7. Shalev, A. et al. Oligonucleotide microarray analysis of intact human pancreatic islets: identification of glucose-responsive genes and a highly regulated TGFbeta signaling pathway. *Endocrinology* 143, 3695-8 (2002).
8. Minn, A, H., Hafele, C. & Shalev, A. Thioredoxin-interacting protein is stimulated by glucose through a carbohydrate response element and induces beta-cell apoptosis. *Endocrinology* 146, 2397-405 (2005).
9. Minn, A. H, et al. Gene expression profiling in INS-1 cells overexpressing thioredoxin-interacting protein. *Biochem Biophys Res Commun* 336, 770-778 (2005),
10. Saxena, G., Chen, J. & Shalev, A. Intracellular Shuttling and Mitochondrial Function of Thioredoxin-interacting Protein. *J Biol Chem* 285, 3997-4005 (2010).
11. Chen, J., Fontes, G., Saxena, G., Poitout, V. & Shalev, A. Lack of TXNIP protects against mitochondria-mediated apoptosis but not against fatty acid-induced ER stress-mediated beta-cell death. *Diabetes* 59, 440-7 (2010).
12. Sun, Y. et al. Development of a micro-array to detect human and mouse microRNAs and characterization of expression in human organs. *Nucleic Acids Res* 32, e188 (2004).
13. Landgraf, P. et al. A mammalian microRNA expression atlas based on small RNA library sequencing. *Cell* 129, 1401-14 (2007).
14. Fernandez-Valverde, S. L., Taft, R. J. & Mattick, J. S. MicroRNAs in beta-cell biology, insulin resistance, diabetes and its complications. *Diabetes* 60, 1825-31 (2011).

15. Kantharidis, P., Wang, B., Carew, R. M. & Lan, H. Y. Diabetes complications: the microRNA perspective. *Diabetes* 60, 1832-7 (2011).
16. Tattikota, S. G. & Poy, M. N. Re-dicing the pancreatic beta-cell: do microRNAs define cellular identity? *Embo J* 30, 797-9 (2011).
17. Guay, C., Roggli, E., Nesca, V., Jacovetti, C. & Regazzi, R. Diabetes mellitus, a microRNA-related disease? *Transl Res* 157, 253-64 (2011).
18. Lynn, F. C. et al. MicroRNA expression is required for pancreatic islet cell genesis in the mouse. *Diabetes* 56, 2938-45 (2007).
19. Kalis, M. et al. Beta-cell specific deletion of dicer1 leads to defective insulin secretion and diabetes mellitus. *PLoS One* 6, e29166 (2011).
20. Melkman-Zehavi, T. et al, miRNAs control insulin content in pancreatic beta-cells via downregulation of transcriptional repressors. *Embo J* 30, 835-45 (2011),
21. Poy, M. N. et al. A pancreatic islet-specific microRNA regulates insulin secretion. *Nature* 432, 226-30 (2004).
22. Zhao, H. et al. Up-regulated pancreatic tissue microRNA-375 associates with human type 2 diabetes through beta-cell deficit and islet amyloid deposition. *Pancreas* 39, 843-6 (2010).
23. Poy, M. N. et al. miR-375 maintains normal pancreatic alpha- and beta-cell mass. *Proc Natl Acad Sci USA* 106, 5813-8 (2009).
24. Roldo, C. et al. MicroRNA expression abnormalities in pancreatic endocrine and acinar tumors are associated with distinctive pathologic features and clinical behavior. *J Clin Oncol* 24, 4677-84 (2006).
25. Krol, J. et al. Characterizing light-regulated retinal microRNAs reveals rapid turnover as a common property of neuronal microRNAs. *Cell* 141, 618-31 (2010).
26. Artner, I. et al. MafA and MafB regulate genes critical to beta-cells in a unique temporal manner. *Diabetes* 59, 2530-9 (2010).
27. Sharma, A. et al. The NeuroD1/BETA2 sequences essential for insulin gene transcription colocalize with those necessary for neurogenesis and p300/CREB binding protein binding. *Mol Cell Biol* 19, 704-13 (1999).
28. Le Lay, J. & Stein, R. Involvement of PDX-1 in activation of human insulin gene transcription. *J Endocrinol* 188, 287-94 (2006).
29. Aramata, S., Han, S. I., Yasuda, K. & Kataoka, K. Synergistic activation of the insulin gene promoter by the beta-cell enriched transcription factors MafA, Beta2, and Pdx1. *Biochim Biophys Acta* 1730, 41-6 (2005).
30. Zhang, C. et al. MafA is a key regulator of glucose-stimulated insulin secretion. *Mol Cell Biol* 25, 4969-76 (2005).
31. Krutzfeldt, J. et al. Silencing of microRNAs in vivo with 'antagomirs'. *Nature* 438, 685-9 (2005).
32. Cha-Molstad, H., Saxena, G., Chen, J. & Shalev, A. Glucose-stimulated Expression of Txnip Is Mediated by Carbohydrate Response Element-binding Protein, p300, and Histone 1-14 Acetylation in Pancreatic Beta Cells. *J Biol Chem* 284, 16898-905 (2009).

Example 2

The present invention provides the first indication that a microRNA can inhibit human insulin transcription. The fact that the preliminary data described herein demonstrates that miR-204 is not only upregulated by TXNIP, but is also increased in diabetes, raises the possibility that this microRNA may contribute to the progression of type 2 diabetes and the well known beta cell dysfunction observed clinically. The inhibition of miR-204 signaling would be beneficial in type 2 diabetes, where it could help counteract or delay the progressive beta cell dysfunction and gradual loss of adequate insulin production. These results may also have important implications for type 1 diabetes as they may provide invaluable information on how to enhance efficiency of beta cell substitutes, which have and continue to be a challenge and are often plagued by the inability to provide adequate insulin production. Thus, the information gained should help in the development of minimally-invasive RNA therapeutics leading to better treatment options for type 1 and 2 diabetes.

Adequate insulin production in pancreatic beta cells is a prerequisite for normal glucose homeostasis. In fact, beta cell dysfunction (combined with insulin resistance) represents a hallmark in the pathogenesis of type 2 diabetes, but the molecular mechanisms involved have not yet been completely elucidated. Previously, we identified thioredoxin-interacting protein (TXNIP) as a critical factor involved in beta cell biology and showed that beta cell TXNIP levels are upregulated in diabetes. In contrast, TXNIP deficiency protected against type 1 and type 2 diabetes by promoting beta cell survival. Now we have discovered, that TXNIP induces beta cell expression of a specific microRNA, miR-204, which in turn seems to block insulin production.

Aim #1. Study the Role of miR-204 and TXNIP in Pancreatic Beta Cell Function/Insulin Production.

Our preliminary data indicate that TXNIP and diabetes induce miR-204 beta cell expression in INS-1 cells as well as in vivo in mice and suggest that miR-204 and TXNIP might be involved in the control of insulin production. To determine the role of beta cell miR-204, we will now overexpress and inhibit miR-204 in INS-1 cells and primary human islets as well as in vivo in normal and diabetic mice using our tested oligonucleotides and antagomir injections and will assess the miR-204 effects on beta cell insulin expression and insulin content and secretion. We will also use our TXNIP overexpressing INS-1 cell line and our whole body and beta cell-specific TXNIP-deficient mouse models to conduct parallel experiments assessing the effects of TXNIP on insulin production.

Aim #2: Identify the Target(s) and Molecular Mechanisms by which miR-204 & TXNIP Exert their Effects in Beta Cells.

Commonly, microRNAs inhibit gene expression by binding to seed sequences in the 3'UTR of target genes marking them for degradation. While our initial studies suggest that miR-204 inhibits beta cell insulin mRNA expression, it does not seem to do so through the insulin 3'UTR, but rather by inhibiting insulin transcription. This suggests that miR-204 acts via downregulation of another target and in fact our preliminary data indicate that this target is MafA, a transcription factor known to induce insulin expression. We will therefore assess the effect of miR-204 on MafA mRNA and protein expression as well as on MafA occupancy of the insulin promoter using chromatin immunoprecipitation studies. To determine whether miR-204 acts through the MafA 3'UTR, we will also use our MafA 3'UTR luciferase reporter constructs encoding the wild-type sequence or a mutated seed sequence. To further establish this novel TXNIP/miR-204/MafA/insulin pathway, we will also investigate the effects of TXNIP on MafA expression and function and will again use our INS-1 cell lines, primary human islets and our various mouse models.

Aim #3: Elucidate the Processes Involved in Regulation of miR-204 Expression.

While we have strong evidence for diabetes and TXNIP increasing beta cell miR-204 expression, the mechanisms involved have remained elusive. TXNIP is not only strongly induced by diabetes it is also a known inhibitor of thioredoxin and thereby leads to increased oxidative stress and mitochondria-mediated apoptosis. We will therefore investigate whether thioredoxin knock down and/or oxidative stress could mimic the TXNIP effects on miR-204 expression. Furthermore, we will also conduct a detailed miR-204 promoter analysis to define the region and putative transcription factors through which diabetes-induced TXNIP and its downstream factors are conferring their effects on miR-204.

Results of these studies will not only significantly expand our understanding of the role of TXNIP and microRNAs in beta cell function, but will also reveal potential novel therapeutic targets to help enhance endogenous insulin production and combat diabetes.

TXNIP Regulates Beta Cell miR-204 Expression.

Figure 12:
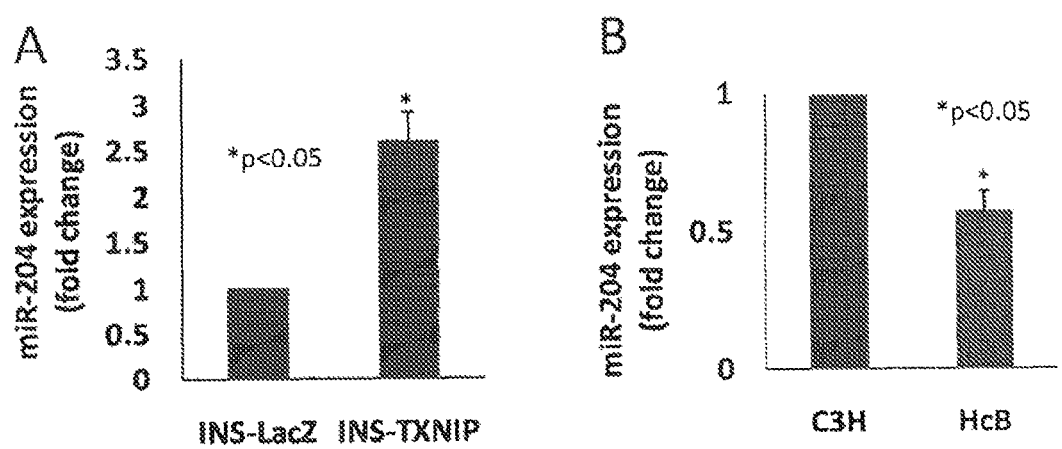
FIG. 12. TXNIP effects on beta cell miR-204 expression. (A) INS-1 cells overexpressing TXNIP (INS-TXNIP) and control cells (INS-LacZ) were grown in 6-well plates using regular culture media (11.1 mM glucose) and RNA was extracted using the miRNeasy mini kit (Qiagen). miR-204 expression was measured by qRT-PCR and corrected for U6 ran as internal standard. (B) Primary islets from 8 week-old male TXNIP-deficient HcB-19 and C3H mice were isolated and analyzed for miR-204 expression. Bars represent means±SEM; n=3.

Using a microRNA microarray (miCURY LNA, Exiqon) and our TXNIP overexpressing INS-1 beta cells we discovered a novel TXNIP function: TXNIP regulates microRNA expression and in particular induced the expression of miR-204>2-fold, findings that we confirmed by real-time RT-PCR (FIG. 12A). In contrast, primary islets from TXNIP-deficient HcB-19 mice showed a significant reduction in miR-204 expression (FIG. 12B) suggesting that TXNIP is a potent regulator of beta cell miR-204 expression.

miR-204 and TAWIP are Upregulated in Islets of Diabetic Mice.

We investigated whether beta cell miR-204 expression might also be altered in diabetes. To this end we used the leptin-deficient obese and diabetic B6ob/ob mice as a model of type 2 diabetes (FIGS. 13A-B). Islets of obese and diabetic mice showed dramatically elevated TXNIP levels (FIG. 13C). Most importantly though, miR-204 expression was also significantly increased in diabetic ob/ob mice as opposed to lean mice (FIG. 13D) indicating that this microRNA might play a role in the beta cell dysfunction and/or beta cell death characteristic of diabetes.

miR-204 and TXNIP Inhibit Insulin Production.

Figure 14:
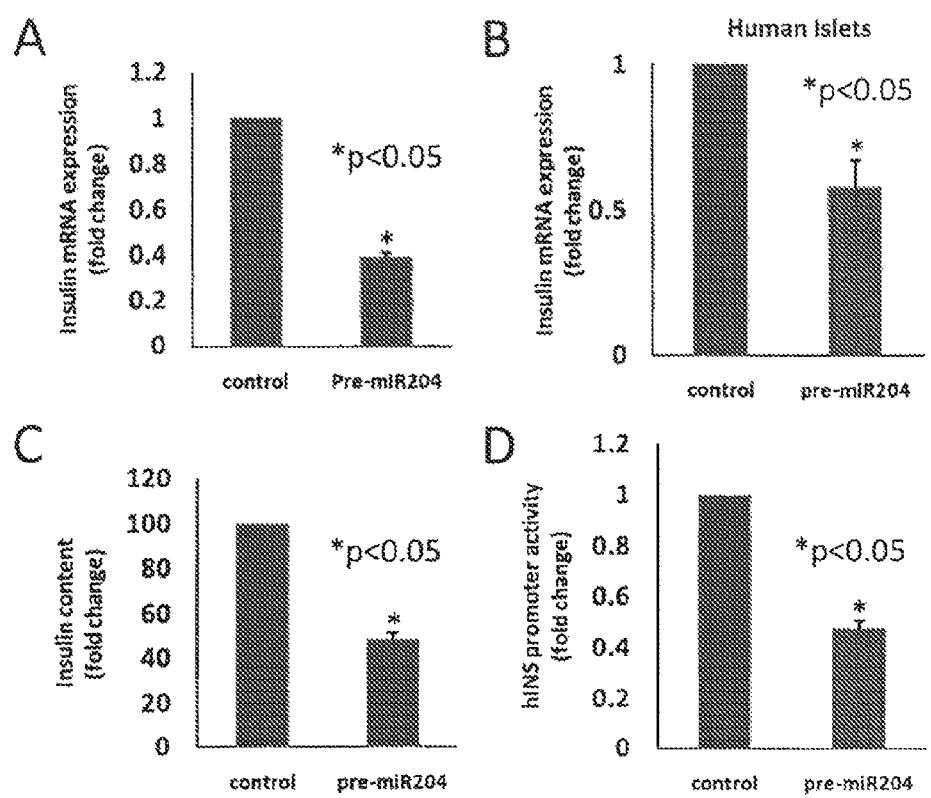
FIG. 14. miR-204 effects on insulin production
(A) INS-1 cells were transfected with miR-204 precursor (pre-miR204) or scrambled negative control 2 (control) (Applied Biosystems) using DharmaFECT1. 72 h after transfection RNA was extracted and analyzed for insulin mRNA (corrected for 18S) by qRT-PCR. (B) Human islets were obtained from the UAB Islet Resource Facility, dispersed and transfected as above. After 72 h insulin mRNA was assessed by qRT-PCR. (C) Cellular insulin protein content in INS-1 cells overexpressing control or pre-miR204 oligo was assessed by ELISA and normalized for cellular DNA content. (D) INS-1 cells were cotransfected with human insulin promoter firefly luciferase reporter construct, pRL-TK renilla and pre-miR204 or control plasmid using DharmaFECTDuo. Cells were harvested 72 h after transfection, and insulin promoter activity was assessed by firefly luciferase (corrected for transfection efficiency by renilla luciferase) using the Dual Luciferase Assay Kit (Promega). Bars represent means±SEM of 3 independent experiments.

To elucidate the unknown function of miR-204, we established a miR-204 overexpression and knock down system using transfection with miR-204 precursor and miR-204 inhibitor oligonucleotides resulting in significantly increased ($p<0.05$) or decreased ($p<0.001$) miR-204 expression as compared to scrambled negative control oligonucleotides, respectively. Since (unlike in the case of TXNIP) initial miR-204 overexpression studies did not reveal any striking effects on beta cell apoptosis, we investigated the possibility that miR-204 might affect beta cell function, i.e., insulin production. In fact, miR-204 overexpression in INS-1 cells led to a >2-fold reduction in insulin mRNA expression (FIG. 14A). (While data shown was obtained with primers detecting expression from both rat insulin genes, primers specific for Ins1 or Ins2 showed the same effect.) In contrast, knock down of miR-204 resulted in a significant increase in insulin mRNA levels ($p<0.05$) (data not shown). Of note, miR-204 is also highly expressed in human islets and overexpression decreased insulin mRNA similar to INS-1 cells (FIG. 14B), demonstrating that this effect was also relevant to human islet biology. In addition, this decrease in insulin mRNA expression translated at the protein level into significantly reduced insulin content in miR-204 overexpressing cells (FIG. 14C). Surprisingly though, we observed that miR-204 inhibited insulin promoter activity (FIG. 14D) (rather than having classical post-transcriptional microRNA effects on mRNA stability or translation). This suggested that the effect was indirect and would likely include a miR-204-induced down regulation of factor(s) involved in insulin transcription.

To further investigate whether TXNIP as an upstream regulator of miR-204 would have similar effects on insulin production, we conducted parallel experiments using our TXNIP overexpressing INS-1 cells as well as human islets and TXNIP deficient HcB-19 mouse islets.

Figure 15:
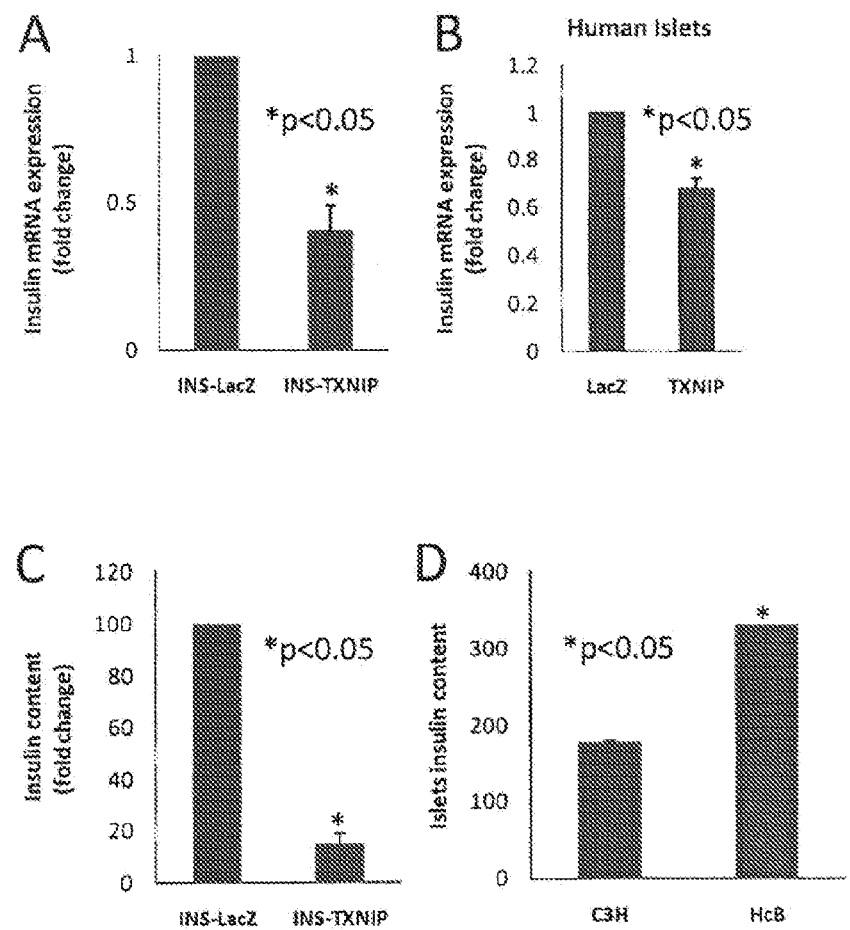
FIG. 15. Insulin production in response to TXNIP modulation. Insulin mRNA as assessed by qRT-PCR in INS-TXNIP cells (A) and human islets transfected with TXNIP (B). Insulin content as assessed by ELISA in INS-TXNIP cells (C) and primary islets of TXNIP-deficient HcB-19 mice (D); n=3

Indeed, TXNIP led to a significant decrease in insulin mRNA levels in INS-1 cells (FIG. 15A) and human islets (FIG. 15B) and caused a dramatic reduction in insulin content (FIG. 15C). In contrast, TXNIP deficient islets demonstrated a highly significant increase in insulin content (FIG. 15D), while insulin secretion was found to be unaltered (11). These findings indicate that TXNIP inhibits beta cell insulin production through induction of miR-204 expression.

miR-204 and TXNIP Regulate MafA Expression.

To start elucidating the mechanisms of miR-204 action, we next wanted to identify the putative gene targets of this microRNA and especially those that might play a role in insulin transcription. We therefore tested whether miR-204 could inhibit the expression of any of the key insulin transcription factors, i.e., MafA/B, NeuroD or PDX1 (38-41). However, only MafA mRNA and protein levels were dramatically reduced in response to miR-204 (FIGS. 16A-B), while the other factors were not significantly altered (data not shown). In addition, miR-204 knock down led to a >2-fold increase in MafA expression. This raised the possibility that MafA was acting as the miR-204 target mediating the effects of this microRNA on insulin gene expression. In fact, comparison of the miR-204 seed sequence and the MafA 3'UTR revealed an almost perfect match (FIG. 16C), suggesting that MafA might indeed be a direct target of miR-204. To now obtain experimental confirmation, we have generated luciferase reporter constructs encoding the MafA wild-type 3'UTR (MafA-WT) or a MafA 3'UTR with mutated seed sequence (MafA-M).

Figure 17:
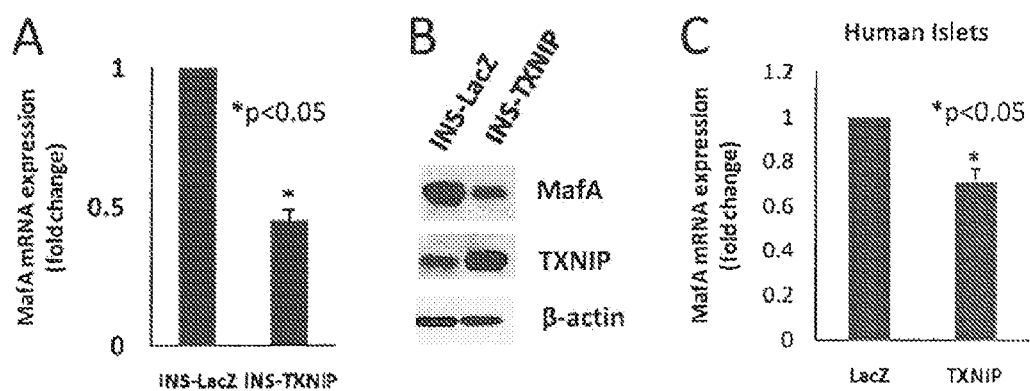
FIG. 17. TXNIP effects on MafA expression. MafA mRNA (A) or protein expression (B) in INS-TXNIP cells. Effects of TXNIP overexpression in human islets on MafA mRNA expression (C); n=3.

To investigate whether TXNIP could mimic the miR-204 effects on MafA, we analyzed our TXNIP overexpressing INS-1 cell line and found a >2-fold reduction in MafA mRNA expression and MafA protein levels (FIGS. 17A-B) similar to the results in response to direct miR-204 overexpression. Moreover, TXNIP also reduced MafA expression in human islets (FIG. 17C) confirming the physiological relevance of these findings.

Together, these preliminary data reveal a novel TXNIP/miR-204/MafA pathway that controls insulin production Study of the Role of miR-204 & TXNIP in Pancreatic Beta Cell Function/Insulin Production.

Our preliminary data indicate that TXNIP and diabetes induce miR-204 beta cell expression in INS-1 cells as well as in vivo in mice and suggest that miR-204 and TXNIP might be involved in the control of insulin production.

Figure 13:
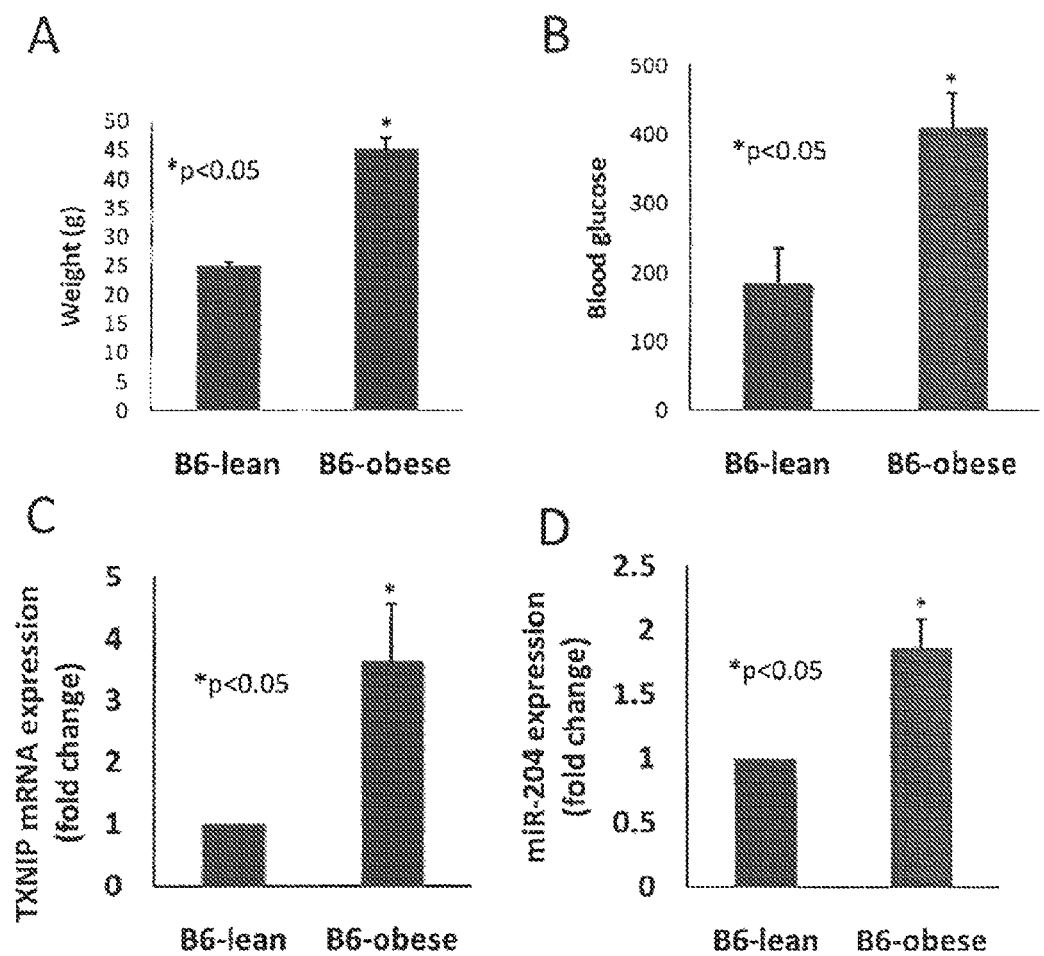
FIG. 13. Diabetes effects on miR-204 and TXNIP expression. Weight (A) and blood glucose (B) in 10 week-old male B6ob/ob and lean control mice. TXNIP mRNA (C) and miR-204 expression (D) in primary islets of diabetic ob/ob or lean control mice as assessed by qRT-PCR; n=5.

To determine the role of beta cell miR-204, we will modulate its expression in vitro and in vivo and assess the effects on beta cell insulin expression, insulin content, and insulin secretion.

miR-204 overexpression. We will use pre-miR204 (AM171000) or scrambled control oligonucleotides (AM17111) (Applied Biosystems) and DharmaFECT1 (Dharmacon) to transiently transfect INS-1 cells and primary human islets as detailed above. While initial studies will be performed under normal cell growth conditions as described above, i.e., in the presence of 11.1 mM glucose, all in vitro experiments will also be repeated in the context of low (5 mM) or high (25 mM) glucose. Human islets will again be obtained from our local UAB islet isolation facility as well as through the National Integrated Islet Distribution Program (IIDP) and always islets from the same donor will be used as controls. After 72 h, cells will be harvested for RNA extraction and measurements of insulin content and insulin secretion.

miR-204 knock down (in vitro and in vivo). We will utilize the miR204 inhibitor oligo (IN-320505-05; meridian Hairpin Inhibitor rno-miR-204) or scrambled control (IN-001005-01-05) (Dharmacon) to perform transfection experiments in INS-1 cells and primary human islets as mentioned above and described herein. This microRNA inhibitor oligonucleotide specifically binds to miR-204 and targets it for degradation. In fact, 72 h after transfection we saw a significant ~5-fold reduction in miR-204 expression, but no effect on other microRNAs (data not shown) confirming the effectiveness and specificity of this approach. In addition to these in vitro studies in INS-1 cells and primary human islets, we will also perform in vivo experiments using tail vein injections of miR-204 antagomir (5'-mA(*)mG(*)mGmCmAmUmAmG-mGmAmUmGmAmCmAmAmAmG mG(*)mG(*)mA(*) mA(*)-3Chl, SEQ ID NO:37) as described previously (42, 43). These antagomirs contain chemical modifications to assure in vivo stability (i.e., 2'-O-methyl modified, six phosphorothioate backbone modifications (two phosphorothioates located at the 5'-end and four at the 3'-end), a cholesterol moiety at the 3'-end) (Dharmacon) and allow for timely assessment of microRNA function in a whole animal model. In our case, this approach also provides a powerful tool to modulate miR-204 not only under normal conditions, but also in the context of diabetes. Two sets of experiments, each with three treatment groups (antagomir, mutant antagomir, saline) will be performed including wild-type mice and obese and diabetic ob/ob mice as a model of type 2 diabetes. Wild-type, male, 6-8 week old C57BL/6 mice will receive up to 3 tail vein injections of antagomir (80 mg/kg body weight), equal dose of mutant antagomir or saline on consecutive days as described previously (42,43). Of note, we already obtained a ~2-fold reduction in islet miR-204 expression after just one injection in our antagomir pilot studies (data not shown). For our B6ob/ob mice, we also confirmed that diabetes ensues ~9-10 weeks of age and that this is associated with a significant increase in islet miR-204 expression (FIG. 13). Therefore, after diabetes has been confirmed by blood glucose readings over 250 mg/dL on two consecutive days, these obese and diabetic male mice and their lean, non-diabetic littermates will again be divided into three treatment groups and will receive antagomir, mutant antagomir or saline injections as described for the wild-type mice. In all mice, blood glucose levels will be assessed daily (by glucometer) and serum will be collected before injection and prior to sacrifice for measurement of insulin levels (by ELISA)(17). We will also perform a glucose tolerance test (GTT) at the beginning and the end of the experiment as detailed previously (17) to obtain an additional measure of glucose homeostasis. Mice will be sacrificed 24 h after the last injection (42) and their pancreatic islets isolated as described (11; 16; 17). Islets will be used for RNA extraction to confirm miR-204 knock down and measure insulin mRNA levels and for insulin content and insulin secretion assays as described (17). Based on similar studies we anticipate that at least 8 mice will be required per group (42; 43).

To further investigate whether TXNIP as an upstream regulator of miR-204 would have similar effects on insulin production, we will conduct parallel experiments assessing the effects of TXNIP on beta cell insulin expression, insulin content, and insulin secretion.

TXNIP overexpression. We will use our stably transfected TXNIP-overexpressing INS-1 cell line (INS-TXNIP) (12, 14) as well as transiently transfected primary human islets to determine whether TXNIP can inhibit insulin production. To test whether miR-204 induction is also necessary for TXNIP-induced inhibition of insulin production, we will knock down miR-204 in TXNIP overexpressing INS-TXNIP cells and assess whether this can blunt the TXNIP effect and restore insulin production.

TXNIP deficiency. To investigate the effects of TXNIP deficiency on insulin production, we will take advantage our two in vivo mouse models of whole body TXNIP deficiency (HcB-19) and our beta cell-specific TXNIP knockout mouse (bTKO) (17). TXNIP deficient mice (HcB-19 or bTKO) and control mice (C3H or lox/lox, respectively) will be sacrificed at ~8 weeks of age and isolated pancreatic islets will again be assessed for insulin mRNA (as well as miR-204) expression, insulin content and insulin secretion. Of note, we have previously shown that both models have significantly increased serum insulin levels and are protected against diabetes (17). Based on our experience with these mouse models, we anticipate that at least 6 mice will be needed per group. To complement these in vivo studies, we also have an in vitro TXNIP siRNA knock down in place (15), which will allow us to downregulate TXNIP in INS-1 cells as well as primary human islets and assess its effects on miR-204 and insulin production.

The main aspects of pancreatic beta cell function are insulin production (including mRNA expression, processing and storage) as well as insulin secretion. Guided by our preliminary data, we will therefore assess the effects of miR-204 and TXNIP on these processes.

Insulin expression. We will measure changes in insulin mRNA expression by quantitative real time RT-PCR as described herein. Again INS-1 cells, primary mouse islets and isolated human islets will be used. In contrast to humans, rodents have two insulin genes and for analysis of mouse and rat insulin mRNA expression we will therefore use 3 sets of primers each designed to detect Ins1, Ins2 or insulin mRNA from both rodent genes and all results will be corrected for 18S run as an internal standard. We will also confirm that effects are mediated by altered insulin transcription, using our established insulin promoter luciferase reporter assay as detailed in the preliminary studies (FIG. 14D).

Insulin content and secretion. We will confirm changes in insulin mRNA expression at the protein level and measure insulin content as well as insulin secretion as mentioned in the preliminary studies and described in detail previously (11). INS-1 cells will be plated into 24-well plates at a density of ~0.5×10$^6$ cells/well and primary mouse and human islets will be hand picked (5 per tube). Basal as well as glucose-stimulated insulin secretion will be assessed using HEPES balanced salt solution (HBSS) and static incubation at 3 mM and 15 mM glucose. (Based on previous data (11), we do not anticipate any change in insulin secretion, but want to exclude the possibility of altered secretion affecting insulin content and therefore will be conducting these experiments in parallel.) For insulin content, cells and islets will be treated with cell lysis buffer; the lysates will be stored overnight at −20° C. and then analyzed using ELISA insulin kits (Chrystal Chem Inc.). Of note, results will be corrected for DNA content as measured by Quant-iTPicoGreendsDNA kit (Invitrogen) to avoid any potential confounding effects due to changes in beta cell size or number.

Identification of the Target(s) and Molecular Mechanisms by which miR-204 & TXNIP Exert their Effects in Beta Cells.

While our initial studies suggest that miR-204 inhibits beta cell insulin mRNA expression, it does not seem to do so through the insulin 3'UTR, but rather by inhibiting insulin transcription. This suggests that miR-204 (and TXNIP) act via downregulation of another target and in fact our preliminary data indicate that this target is MafA, a transcription factor known to induce insulin expression (38; 41).

To further study this, we will assess the effect of miR-204 and TXNIP on MafA mRNA and protein expression, MafA occupancy of the insulin promoter and MafA 3'UTR function.

MafA mRNA and protein expression. We will assess the effects of miR-204 on MafA mRNA and protein expression using again quantitative real-time PCR and Western blotting as shown herein. INS-1 cells and primary human and mouse islets (including those harvested from the antagomir experiments in wild-type and diabetic ob/ob mice) described above will be analyzed.

Similarly, we will determine MafA expression in INS-1 cells and human islets with TXNIP overexpression or TXNIP knock down and especially in TXNIP-deficient primary HcB-19 and bTKO mouse islets. However, any reduction in MafA expression would also have to impair MafA-mediated insulin transcription in order to explain any changes in insulin mRNA expression.

MafA occupancy of the insulin promoter: To assess whether miR-204 and/or TXNIP would inhibit in vivo binding of MafA to the insulin promoter, we will perform chromatin immunoprecipitation (ChIP) studies. We have already confirmed that we can get appropriate enrichment of MafA on the insulin promoter using immunoprecipitation with MafA antibody (sc-66958, Santa Cruz). In contrast, no binding was observed to GAPDH or with IgG immunoprecipitation serving as negative controls (data not shown). In brief, INS-1 cells will be transfected with pre-miR204 or scrambled oligo as described herein and after 72 h cells will be crosslinked as described previously and analyzed for MafA occupancy of the insulin promoter using our tested MafA antibody for immunoprecipitation and primers flanking the MafA binding site. To assess the effects on TXNIP, we will again take advantage of our INS-TXNIP and INS-LacZ cell lines. While these initial studies will be performed in INS-1 cells, we will confirm findings in human islets, which we have successfully used for ChIP studies previously (13).

Figure 16:
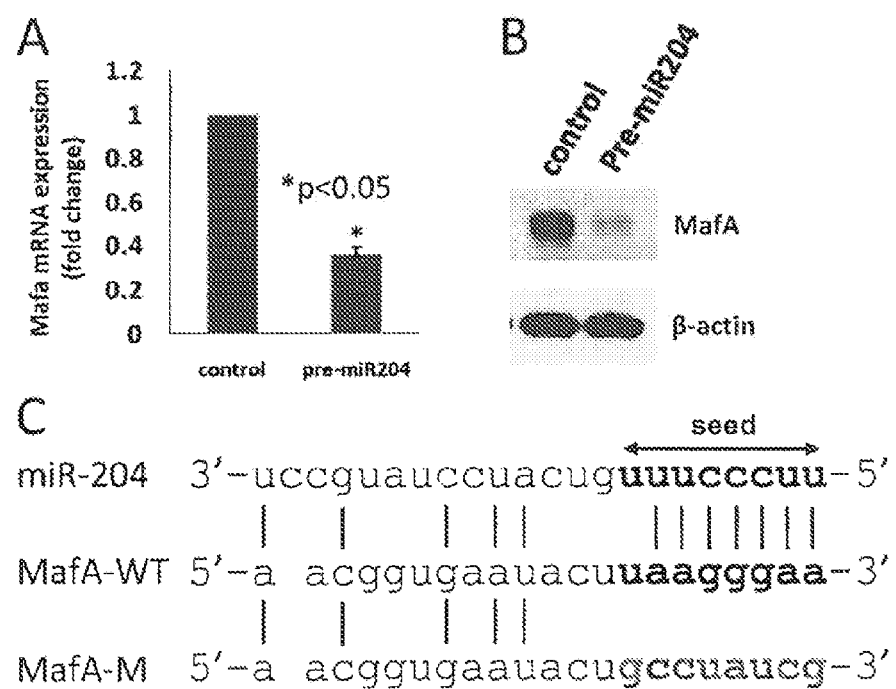
FIG. 16. MafA as a target of miR-204. miR-204 effects on MafA mRNA (A) or protein expression (B) as assessed by qRT-PCR and immunoblotting; n=3. miR-204 (SEQ ID NO:33) seed sequence and MafA 3'UTR (SEQ ID NO:34) target or mutated (SEQ ID NO:35) target sequence (C).

MafA 3'UTR function: Our preliminary data suggest that miR-204 inhibits MafA expression and the MafA 3'UTR sequence seems to suggest that MafA is a target of miR-204. We have generated MafA 3'UTR luciferase reporter constructs (pMIR-REPORT, Applied Biosystems) encoding the MafA 3'UTR wild-type sequence or a mutated seed sequence (FIG. 16C). We will now use these constructs to determine whether miR-204 indeed targets the MafA 3'UTR, To this end INS-1 cells will be grown in 12-well plates and cotransfected with wild-type (MafA-WT) or mutant MafA (MafA-M) 3'UTR reporter plasmid and pre-miR204 or scrambled control (Applied Biosystems) using DharmaFECT Duo transfection reagent. To control for transfection efficiency, cells will also be cotransfected with pRL-TK (Promega) control plasmid expressing the renilla luciferase reporter gene. Cells will be harvested 24 h after transfection, and firefly as well as renilla luciferase activity determined using the Dual Luciferase Assay Kit (Promega).

Elucidation of the Processes Involved in Regulation of miR-204 Expression.

We will investigate whether thioredoxin knock down and/or oxidative stress or apoptosis (e.g., hydrogen peroxide, staurosporine) could mimic the TXNIP effects on miR-204 expression.

Thioredoxin knock down. We will knock down thioredoxin 1 (Trx1), mitochondrial thioredoxin 2 (Trx2) or both using our tested siRNAs and scrambled oligos (Dharmacon) as described previously (15) and will determine whether any of these interventions can induce miR-204 expression. First, studies will be performed under normal cell growth conditions, i.e., in the presence of 11.1 mM glucose, but will also be repeated in the context of low (5 mM) or high (25 mM) glucose. While these initial studies will be performed in INS-1 cells, any positive results will be confirmed in human islets.

Oxidative stress and apoptosis. To induce oxidative stress we will treat INS-1 cells and primary mouse and human islets with increasing doses of hydrogen peroxide (5-50 µM) and for increasing amounts of time (1-72 h) as described previously (15,16) and will assess the effect on miR-204 expression. We will also monitor for alterations in apoptosis and/or any changes in TXNIP expression. To specifically induce mitochondrial apoptosis (the pathway stimulated by TXNIP) similar experiments will be performed using staurosporine (0.5 µM) (15; 16).

miR-204 is encoded in an intron of the TRPM3 gene (a cation-selective channel). (While many microRNAs are transcribed from their own genes, about 40% are encoded in introns of protein-coding host genes that tend to be well conserved across species (45). This means that miR-204 and TRPM3 share the same promoter and are expected (at least at the transcriptional level) to be regulated in parallel. Our preliminary data show that like miR-204, TRPM3 expression is also significantly increased in response to TXNIP (data not shown) suggesting that TXNIP indeed induces miR-204 transcription through this shared promoter region. However, unlike miR-204, TRPM3 does not inhibit insulin expression and therefore could not mediate the TXNIP effects on insulin observed (data not shown). We will conduct a detailed miR-204(/TRPM3) promoter analysis to define the region through which TXNIP and its downstream factors are conferring their effects.

miR-204 promoter analysis. Having cloned the miR-204 promoter region and generated a luciferase reporter system, we will test the effects of TXNIP by performing transfection studies using our TXNIP-overexpressing INS-TXNIP and control INS-LacZ cell lines. We will also perform a deletion analysis as we did previously for the TXNIP promoter (12; 13). The region identified to be responsible for the TXNIP effect will then be first analyzed in silico using the MatInspector software to identify putative binding sites. Promising candidates will then be tested experimentally using ChIP to confirm in vivo binding to the miR-204 promoter and then by manipulating expression of the putative transcription factor and analysis of miR-204 promoter activity and miR-204 mRNA expression. In addition, we will also test for any potential effects of Trx knock down or oxidative stress on miR-204 promoter activity and will study the mechanisms by which TXNIP might alter downstream transcription factor expression and/or function.

In summary, we have discovered a novel microRNA that is upregulated in response to diabetes and TXNIP and inhibits insulin production and the proposed studies to elucidate this pathway are therefore highly innovative. They also employ molecular biology as well as in vitro cell biology, in vivo mouse models and human islets and this comprehensive approach should help provide physiologically relevant data and shed new light on a thus far underappreciated control mechanism governing pancreatic beta cell function. In addition, the results of the proposed studies will not only impact the fields of microRNA biology and TXNIP signaling, but should also reveal potential novel therapeutic targets to help enhance endogenous insulin production and combat diabetes. STATISTICAL ANALYSIS. To calculate the significance of a difference between two means, we will use Student's t-tests. For data sets of more than two groups and to analyze changes over time we will utilize one-way and two-way ANOVA calculations. All analyses will be performed using the SigmaStat software.

References for Example 2 and Background

1. Lawrence M C, McGlynn K, Park B H, Cobb M H: ERK1/2-dependent activation of transcription factors required for acute and chronic effects of glucose on the insulin gene promoter. *J Biol Chem* 280:26751-26759, 2005

2. Khoo S, Gibson T B, Arnette D, Lawrence M, January B, McGlynn K, Vanderbilt C A, Griffen S C, German M S, Cobb M H: MAP Kinases and Their Roles in Pancreatic beta-Cells. *Cell Biochem Biophys* 40:191-200, 2004

3. Kaiser N, Leibowitz G, Nesher R: Glucotoxicity and beta-cell failure in type 2 diabetes mellitus. *J Pediatr Endocrinol Metab* 16:5-22, 2003

4, Poitout V, Robertson R P: Minireview: Secondary beta-cell failure in type 2 diabetes—a convergence of glucotoxicity and lipotoxicity. *Endocrinology* 143:339-342, 2002

5. Nishiyama A, Matsui M, Iwata S, Hirota K, Masutani H, Nakamura H, Takagi Y, Sono H, Gon Y, Yodoi J: Identification of thioredoxin-binding protein-2/vitamin D(3) up-regulated protein 1 as a negative regulator of thioredoxin function and expression. *J Biol Chem* 274:21645-21650, 1999

6. Junn E, Han S H, Im J Y, Yang Y, Cho E W, Urn H D, Kim D K, Lee K W, Han P L, Rhee S G, Choi I: Vitamin D3 up-regulated protein 1 mediates oxidative stress via suppressing the thioredoxin function. *J Immunol* 164:6287-6295, 2000

7. Yamanaka H, Maehira F, Oshiro M, Asato T, Yanagawa Y, Takei H, Nakashima Y: A possible interaction of thioredoxin with VDUP1 in HeLa cells detected in a yeast two-hybrid system. *Biochem Biophys Res Commun* 271:796-800, 2000

8. Nishiyama A, Masutani H, Nakamura H, Nishinaka Y, Yodoi J: Redox regulation by thioredoxin and thioredoxin-binding proteins. *IUBMB Life* 52:29-33, 2001

9. Patwari P, Higgins L J, Chutkow W A, Yoshioka J, Lee R T: The interaction of thioredoxin with Txnip: Evidence for formation of a mixed disulfide by disulfide exchange. *J Biol Chem*, 2006

10. Shalev A, Pise-Masison C A, Radonovich M, Hoffmann S C, Hirshberg B, Brady J N, Harlan D M: Oligonucleotide microarray analysis of intact human pancreatic islets: identification of glucose-responsive genes and a highly regulated TGFbeta signaling pathway. *Endocrinology* 143:3695-3698, 2002

11, Chen J, Saxena G, Mungrue I N, Lusis A J, Shalev A: Thioredoxin-Interacting Protein: A Critical Link between Glucose Toxicity and Beta Cell Apoptosis. *Diabetes* 57:938-944, 2008

12. Minn A H, Hafele C, Shalev A: Thioredoxin-interacting protein is stimulated by glucose through a carbohydrate response element and induces beta-cell apoptosis. *Endocrinology* 146:2397-2405, 2005

13. Cha-Molstad H, Saxena G, Chen J, Shalev A: Glucose-stimulated Expression of Txnip Is Mediated by Carbohydrate Response Element-binding Protein, p300, and Histone H4 Acetylation in Pancreatic Beta Cells. *J Biol Chem* 284:16898-16905, 2009

14. Minn A H, Pise-Masison C A, Radonovich M, Brady J N, Wang P, Kendziorski C, Shalev A: Gene expression profiling in INS-1 cells overexpressing thioredoxin-interacting protein. *Biochem Biophys Res Commun* 336:770-778, 2005

15. Saxena G, Chen J, Shalev A: Intracellular Shuttling and Mitochondrial Function of Thioredoxin-interacting Protein. *J Biol Chem* 285:3997-4005, 2010

16. Chen J, Fontes G, Saxena G, Poitout V, Shalev A: Lack of TXNIP protects against mitochondria-mediated apoptosis but not against fatty acid-induced ER stress-mediated beta-cell death. *Diabetes* 59:440-447, 2010

17. Chen J, Hui S T, Couto F M, Mungrue I N, Davis D B, Attie A D, Lusis A J, Davis R A, Shalev A: Thioredoxin-Interacting Protein Deficiency Induces Akt/Bcl-xL Signaling and Pancreatic Beta Cell Mass and Protects Against Diabetes. *FASEB J* 22:3581-3594, 2008

18. Parikh H, Carlsson E, Chutkow W A, Johansson L E, Storgaard H, Poulsen P, Saxena R, Ladd C, Schulze P C, Mazzini M J, Jensen C B, Krook A, Bjornholm M, Tornqvist H, Zierath J R, Ridderstrale M, Altshuler D, Lee R T, Vaag A, Groop L C, Mootha V K: TXNIP Regulates Peripheral Glucose Metabolism in Humans. *PLoS Med* 4:e158, 2007

19. Chutkow W A, Patwari P, Yoshioka J, Lee R T: Txnip is a critical regulator of hepatic glucose production. *J Biol Chem*, 2007

20. Sun Y, Koo S, White N, Peralta E, Esau C, Dean N M, Perera R J: Development of a micro-array to detect human and mouse microRNAs and characterization of expression in human organs. *Nucleic Acids Res* 32:e188, 2004

21. Landgraf P, Rusu M, Sheridan R, Sewer A, Iovino N, Aravin A, Pfeffer S, Rice A, Kamphorst A O, Landthaler M, Lin C, Socci N D, Hermida L, Fulci V, Chiaretti S, Foa R, Schliwka J, Fuchs U, Novosel A, Muller R U, Schermer B, Bissels U, Inman J, Phan Q, Chien M, Weir D B, Choksi R, De Vita G, Frezzetti D, Trompeter H I, Hornung V, Teng G, Hartmann G, Palkovits M, Di Lauro R, Wernet P, Macino G, Rogler C E, Nagle J W, Ju J, Papavasiliou F N, Benzing T, Lichter P, Tam W, Brownstein M J, Bosio A, Borkhardt A, Russo J J, Sander C, Zavolan M, Tuschl T: A mammalian microRNA expression atlas based on small RNA library sequencing. *Cell* 129:1401-1414, 2007

22. Fernandez-Valverde S L, Taft R J, Mattick J S: MicroRNAs in beta-cell biology, insulin resistance, diabetes and its complications. *Diabetes* 60:1825-1831, 2011

23. Kantharidis P, Wang B, Carew R M, Lan H Y: Diabetes complications: the microRNA perspective. *Diabetes* 60:1832-1837, 2011

24. Tattikota S G, Poy M N: Re-dicing the pancreatic beta-cell: do microRNAs define cellular identity? *Embo J* 30:797-799, 2011

25. Guay C, Roggli E, Nesca V, Jacovetti C, Regazzi R: Diabetes mellitus, a microRNA-related disease? *Transl Res* 157:253-264, 2011

26. Lynn F C, Skewes-Cox P, Kosaka Y, McManus M T, Harfe B D, German M S: MicroRNA expression is required for pancreatic islet cell genesis in the mouse. *Diabetes* 56:2938-2945, 2007

27. Kalis M, Bolmeson C, Esguerra J L, Gupta S, Edlund A, Tormo-Badia N, Speidel D, Holmberg D, Mayans S, Khoo N K, Wendt A, Eliasson L, Cilio C M: Beta-cell specific deletion of dicer1 leads to defective insulin secretion and diabetes mellitus. *PLoS One* 6:e29166, 2011

28. Melkman-Zehavi T, Oren R, Kredo-Russo S, Shapira T, Mandelbaum A D, Rivkin N, Nir T, Lennox K A, Behlke M A, Dor Y, Hornstein E: miRNAs control insulin content in pancreatic beta-cells via downregulation of transcriptional repressors. *Embo J* 30:835-845, 2011

29. Poy M N, Eliasson L, Krutzfeldt J, Kuwajima S, Ma X, Macdonald P E, Pfeffer S, Tuschl T, Rajewsky N, Rorsman P, Stoffel M: A pancreatic islet-specific microRNA regulates insulin secretion. *Nature* 432:226-230, 2004

30, Zhao H, Guan J, Lee H M, Sui Y, He L, Siu J J, Tse P P, Tong P C, Lai F M, Chan J C: Up-regulated pancreatic tissue microRNA-375 associates with human type 2 diabetes through beta-cell deficit and islet amyloid deposition. *Pancreas* 39:843-846, 2010

31, Poy M N, Hausser J, Trajkovski M, Braun M, Collins S, Rorsman P, Zavolan M, Stoffel M: miR-375 maintains normal pancreatic alpha- and beta-cell mass. *Proc Natl Acad Sci USA* 106:5813-5818, 2009

32, Roggli E, Britan A, Gattesco S, Lin-Marq N, Abderrahmani A, Meda P, Regazzi R: Involvement of microRNAs in the cytotoxic effects exerted by proinflammatory cytokines on pancreatic beta-cells. *Diabetes* 59:978-986, 2010

33. Ruan Q, Wang T, Kameswaran V, Wei Q, Johnson D S, Matschinsky F, Shi W, Chen Y H: The microRNA-21-PDCD4 axis prevents type 1 diabetes by blocking pancreatic beta cell death. *Proc Natl Acad Sci USA* 108:12030-12035, 2011

34, Tang X, Muniappan L, Tang G, Ozcan S: Identification of glucose-regulated miRNAs from pancreatic {beta} cells reveals a role for miR-30d in insulin transcription. *Rna* 15:287-293, 2009

35. Fred R G, Bang-Berthelsen C H, Mandrup-Poulsen T, Grunnet L G, Welsh N: High glucose suppresses human islet insulin biosynthesis by inducing miR-133a leading to decreased polypyrimidine tract binding protein-expression. *PLoS One* 5:e10843, 2010

36. Krol J, Busskamp V, Markiewicz I, Stadler M B, Ribi S, Richter J, Duebel J, Bicker S, Fehling H J, Schubeler D, Oertner T G, Schratt G, Bibel M, Roska B, Filipowicz W: Characterizing light-regulated retinal microRNAs reveals rapid turnover as a common property of neuronal microRNAs. *Cell* 141:618-631, 2010

37. Roldo C, Missiaglia E, Hagan J P, Falconi M, Capelli P, Bersani S, Calin G A, Volinia S, Liu C G, Scarpa A, Croce C M: MicroRNA expression abnormalities in pancreatic endocrine and acinar tumors are associated with distinctive pathologic features and clinical behavior. *J Clin Oncol* 24:4677-4684, 2006

38. Artner I, Hang Y, Mazur M, Yamamoto T, Guo M, Lindner J, Magnuson M A, Stein R: MafA and MafB regulate genes critical to beta-cells in a unique temporal manner. *Diabetes* 59:2530-2539, 2010

39. Sharma A, Moore M, Marcora E, Lee J E, Qiu Y, Samaras S, Stein R: The NeuroD1/BETA2 sequences essential for insulin gene transcription colocalize with those necessary for neurogenesis and p300/CREB binding protein binding. *Mol Cell Biol* 19:704-713, 1999

40. Le Lay J, Stein R: Involvement of PDX-1 in activation of human insulin gene transcription. *J Endocrinol* 188:287-294, 2006

41. Aramata S, Han S I, Yasuda K, Kataoka K: Synergistic activation of the insulin gene promoter by the beta-cell enriched transcription factors MafA, Beta2, and Pdx1. *Biochim Biophys Acta* 1730:41-46, 2005

42. Krutzfeldt J, Rajewsky N, Braich R, Rajeev K G, Tuschl T, Manoharan M, Stoffel M: Silencing of microRNAs in vivo with 'antagomirs'. *Nature* 438:685-689, 2005

43. Care A, Catalucci D, Felicetti F, Bonci D, Addario A, Gallo P, Bang M L, Segnalini P, Gu Y, Dalton N D, Elia L, Latronico M V, Hoydal M, Autore C, Russo M A, Dorn G W, 2nd, Ellingsen 0, Ruiz-Lozano P, Peterson K L, Croce C M, Peschle C, Condorelli G: MicroRNA-133 controls cardiac hypertrophy. *Nat Med* 13:613-618, 2007

44. Huang J, Zhao L, Xing L, Chen D: MicroRNA-204 regulates Runx2 protein expression and mesenchymal progenitor cell differentiation. *Stem Cells* 28:357-364, 2010

45. Barik S: An intronic microRNA silences genes that are functionally antagonistic to its host gene. *Nucleic Acids Res* 36:5232-5241, 2008

46. Minn A H, Couto F M, Shalev A: Metabolism-independent sugar effects on gene transcription: the role of 3-o-methylglucose. *Biochemistry* 45:11047-11051, 2006

Example 3

Thioredoxin-Interacting Protein Regulates Insulin Transcription Through microRNA-204

Tissue culture: INS-1 beta-cells and stably transfected INS-TXNIP overexpressing human TXNIP or control INS-LacZ cells were grown as previously described[12]. Mouse pancreatic islets were isolated by collagenase digestion as detailed previously[4]. Human islets were obtained from the UAB Islet Resource Facility and always islets from the same donor were used as control and at least islets from 3 different donors were used per experiment.

Animal studies: All mouse studies were approved by the University of Alabama at Birmingham Animal Care and Use Committee and conform to the NIH Guide for the Care and Use of Laboratory Animals. The C3H congenic TXNIP-deficient HcB-19 (HcB) mice harbouring a naturally occurring nonsense mutation in the TXNIP gene and the control C3H/DiSnA (C3H) strain as well as beta cell-specific TXNIP knockout mice (bTKO) and their controls (lox/lox) have been described previously[5]. Male, 1-year old animals were used for the studies shown.

Plasmid construction and transfection assays: The TXNIP expression plasmid has been described previously[12], construction of Ins-Luc, MafA-WT-3'Luc or MafA-M-3'Luc and transfection assays are described in the Supplementary Methods.

Quantitative real-time RT-PCR: qRT-PCR was performed as described previously[5] using a lightcycler 480 system (Roche, Indianapolis, Ind.) and the primers listed in Table 1. miR-204 expression was quantified using a TaqMan microRNA Assay (Applied Biosystems). Gene and microRNA expression results were corrected for 18S and U6 run as internal standards, respectively. Internal standards were stable throughout all experiments and experiments were run in duplicates.

Immunoblotting: Protein extracts were prepared and analysed as described previously[4]. MafA was detected by Rabbit anti-MafA (sc-66958X, Santa Cruz Biotechnology, Santa Cruz, Calif.). Total and phospho-STAT3 were detected by rabbit anti-STAT3 (4904, Cell Signaling Technology, Danvers, Mass.) and rabbit anti-phospho-STAT3 (9145, Cell Signaling Technology).

Insulin content and secretion: Insulin content and secretion of isolated islets and INS-1 cells was assessed by ELISA and normalized for DNA content as described previously[4] and detailed in the Supplementary Methods, respectively.

Chromatin immunoprecipitation (ChIP): ChIP assays were performed as described previously[49]. 5 µg of rabbit anti-MafA (A300-611A, Bethyl Laboratories, Montgomery, Tex.) or normal rabbit IgG (sc-2027, Santa Cruz) were used for immunoprecipitation and purified DNA fragments were quantified by qPCR with primers described in Table 1.

Statistical analysis: Student's t-tests or ONE-WAY-ANOVA were used to calculate the significance of a difference between two or more groups, respectively.

Plasmid construction, transfection and luciferase assays: The human insulin promoter region was amplified from genomic DNA with primers from Table 1 and subcloned into the MluI and HindIII restriction sites of the pGL3 enhancer vector (Promega, Madison, Wis.) providing the Ins-Luc reporter plasmid. The wild-type MafA 3'UTR region containing a conserved miR-204 binding site was amplified from rat genomic DNA using primers designed based on the sequence found in the UCSC genome browser between the stop codon and poly A site of rat MafA (Table 1). To generate the rat MafA mutant reporter plasmid, 8-bp mutations were introduced by two rounds of PCR and the primers listed in Table 1. PCR products were subcloned into the SpeI and PmeI sites of the pMIR-REPORT Luciferase vector (Applied Biosystems, Foster City, Calif.) yielding the MafA-WT-3'Luc and MafA-M-3'Luc 3'UTR reporter plasmids. All plasmids were confirmed by sequencing. For transfection experiments, INS-1 cells were plated in 6-well plates and grown overnight to ~60% confluence. Human islets (500 per tube) or mouse islets (100 per tube) were gently dispersed by incubation for 5 minutes in 200 μl of 0.05% Trypsin-EDTA (Invitrogen, Grand Island, N.Y.) at 37° C. washed and resuspended in culture medium. Cells were transfected with hsa-miR-204 precursor or pre-miR negative control 2 (Applied Biosystems) at a final concentration of 25_nM using DharmaFECT1 transfection reagent (Dharmacon/Thermo Scientific, Chicago, Ill.). For luciferase assays, INS-1 cells were grown overnight in 12-well plates and cotransfected with Ins-Luc, MafA-WT-3'Luc or MafA-M-3'Luc and hsa-miR-204 or negative control using DharmaFECTDuo transfection reagent (Dharmacon/Thermo Scientific). To control for transfection efficiency, cells were cotransfected with pRL-TK (Promega) control plasmid expressing renilla luciferase and firefly as well as renilla luciferase activity were determined using the Dual Luciferase Assay Kit (Promega).

Insulin content and secretion: INS-1 cells were plated in 24-well plates and after overnight incubation at 5 mM glucose the media was removed and cells were incubated in KRB buffer with 2.5 mM glucose (135 mM NaCl, 3.6 mM KCl, 10 mM Hepes [pH7.4], 5 mM $NaHCO_3$, 0.5 mM $NaH_2PO_4$, 0.5 mM $MgCl_2$, 1.5 mM $CaCl_2$) for 1 hr. After stimulation with KRB buffer containing 16.7 mM of glucose for 1 hr, media was harvested for later insulin assay. Cells were lysed with 300 μl lysis buffer (100 mM Tris-HCl [pH8.0], 300 mM NaCl, 10 mM NaF, 2 mM NaOrthovanadate, 2% NP-40, 2 Protease cocktail tablets [Roche]) and lysates stored overnight at −20° C. After centrifugation at 5000 rpm for 5 min, the supernatants were harvested for insulin assay with the Ultra Sensitive Rat Insulin ELISA Kit (Crystal Chem Inc., Downers Groves, Ill.) and transfected mouse islets were analyzed with the Mouse Insulin Assay kit (ALPCO Diagnostics, Salem, N.H.). Results were normalized for DNA content as determined by Quant-iTPicoGreendsDNA Assay kit (Invitrogen).

Results: Comparison of our TXNIP overexpressing INS-1 beta cell line (INS-TXNIP) and INS-LacZ control cell line using miRCURY LNA microRNA Arrays (Exiqon) and a threshold of 0.7 absolute difference in LogMedianRatio (1.6-fold change) revealed five microRNAs that were upregulated in response to TXNIP: miR-139-5p; miR-193; miR-204; miR-200c; and miR-141 (Table 2). After confirming these findings by quantitative real-time PCR (qRT-PCR), we started to investigate the role of these micRNAs by systematically knocking them down using specific inhibitor oligonucleotides and assessing the effects on insulin production, a key aspect of beta cell function. However, only knockdown of microRNA-204 (miR-204), led to any significant effect and to an increase in insulin expression. Moreover, only overexpression of miR-204, but not of any of the other microRNAs resulted in a marked decrease in insulin mRNA (data not shown). Interestingly, miR-204 (5'-UUCCCUUUGUCAUC-CUAUGCCU-3', SEQ ID NO:2), which is fully conserved between human, rat and mouse, has not been implicated in beta cell biology, but was found to be highly expressed in insulinomas[29]. Consistent with this observation, miR-204 was readily detectable in INS-1 cells, but in alignment with other microRNAs its expression was even higher in primary human islets, whereas expression in mouse islets was lower than in the INS-1 cells (data not shown). Of note, human pancreatic islets were also one of the major sites of miR-204 expression according to the microRNA.org website, but its function and target genes remained unknown. Taken together, these findings indicated that miR-204 might play an important role in beta cell biology and we therefore decided to focus on this microRNA.

Figure 18:
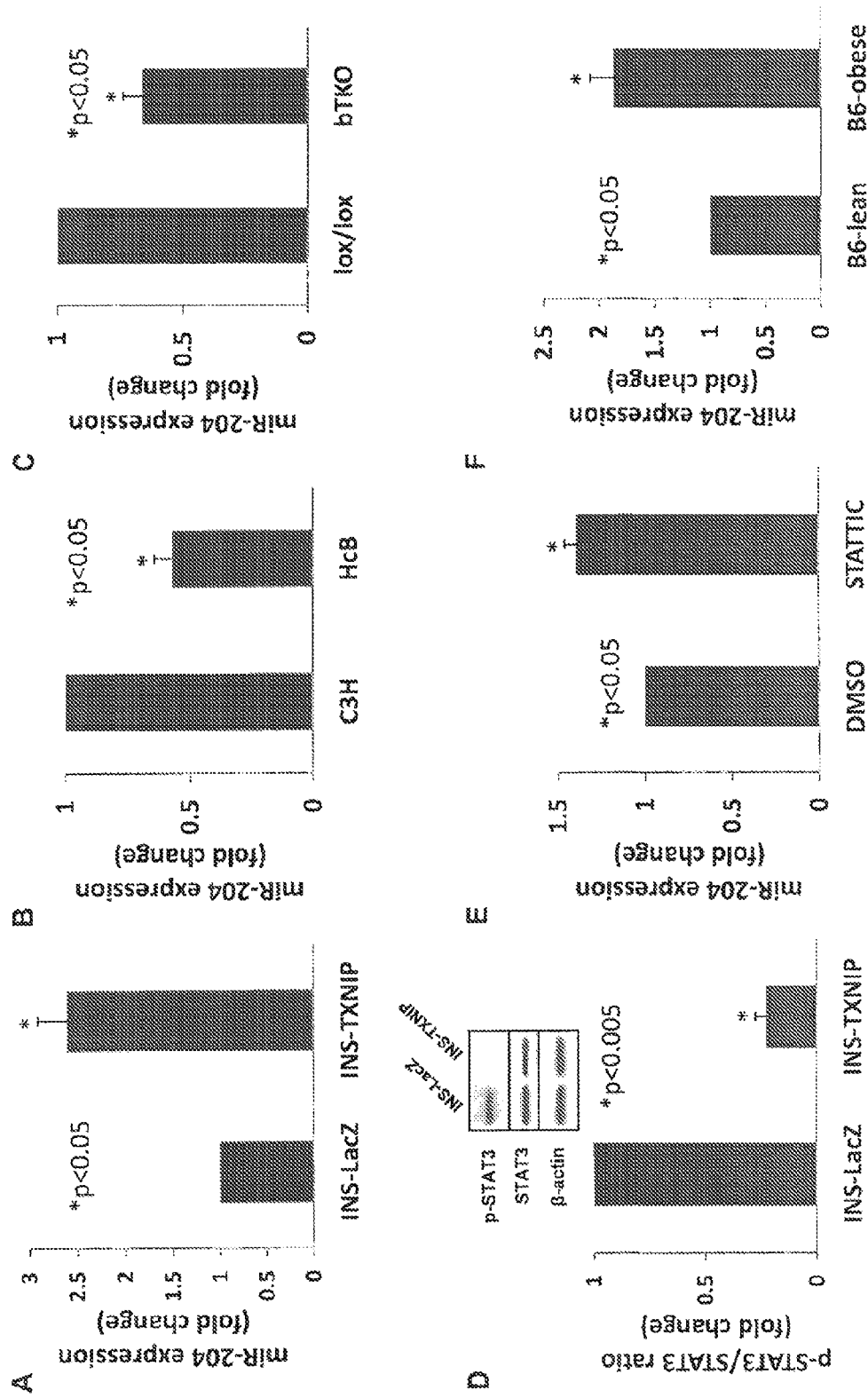
FIG. 18. Effects of TXNIP and diabetes on beta cell miR-204 expression. Expression of miR-204 was assessed by qRT-PCR in (A) INS-1 cells overexpressing TXNIP (INS-TXNIP) and control (INS-LacZ) cells, (B) primary islets of TXNIP-deficient HcB-19 and C3H control mice, and (C) primary islets of beta-cell-specific TXNIP knockout bTKO and lox/lox control mice. (D) TXNIP effects on STAT3 activation were determined by immunoblotting for phospho-STAT3

Using (qRT-PCR), we found that miR-204 expression was >2-fold higher in INS-TXNIP cells as opposed to control INS-LacZ cells (FIG. 18A) confirming our microarray findings. In contrast, primary islets from TXNIP-deficient HcB-19 mice (harbouring a natural nonsense mutation in the TXNIP gene) showed a significant reduction in miR-204 expression (FIG. 18B). Similarly, miR-204 was significantly reduced in islets from our bTKO beta cell-specific TXNIP knockout mice (FIG. 18C) further indicating that TXNIP regulates beta cell miR-204 expression in vivo.

miR-204 is encoded within intron 6 of the TRPM3 gene (transient receptor potential melastatin 3, a cation-selective channel) and is transcribed in the same direction as TRPM3[30]. Since miR-204 and TRPM3 are therefore sharing the same promoter, we deduced that, if TXNIP were to regulate miR-204 expression at the transcriptional level, TRPM3 would be co-regulated in parallel. Indeed, we found that TRPM3 expression was >3-fold higher in TXNIP overexpressing INS-TXNIP cells as opposed to control INS-LacZ cells, whereas primary islets from TXNIP-deficient HcB-19 mice showed a significant reduction in TRPM3 expression (data not shown). These findings are very similar to the results obtained for miR-204 and indicate that in fact, TXNIP upregulates miR-204 by inducing its transcription. Since TXNIP is not known to act as a transcription factor, we deduced that it acts through regulating another factor. Interestingly, the signal transducer and activator of transcription 3 (STAT3) has recently been implicated in the downregulation of miR-204 expression by multiple reports[6-9] and, given the observed upregulation of miR-204 in response to TXNIP, we investigated whether TXNIP might inhibit STAT3. Indeed, while TXNIP had no effect on STAT3 mRNA expression (data not shown) or total protein levels, STAT3 phosphorylation/activation (which is critical for STAT3-mediated transcription) was dramatically reduced in response to TXNIP (FIG. 18D). Using STATTIC, a small molecule that selectively inhibits the activation of the STAT3 transcription factor by blocking its phosphorylation and dimerization (sc-202818, Santa Cruz Biotechnology, Santa Cruz, Calif.), we investigated whether this could mimic the effects of TXNIP. In fact, similarly to TXNIP, STATTIC significantly induced miR-204 expression (FIG. 18E) as well as its host gene TRPM3 (data not shown), indicating that TXNIP confers its effects on miR-204 at least in part through inhibition of STAT3.

Given the involvement of TXNIP in diabetes[5,12,31], we investigated whether beta cell miR-204 expression might also be altered in diabetes. To this end we used the well-established leptin-deficient, obese and diabetic B6-obese mice as a model of type 2 diabetes. Islets of obese and diabetic mice showed dramatically elevated (>3-fold) Txnip levels (data not shown). Most importantly though, miR-204 expression was also significantly increased in diabetic B6-obese mice as opposed to lean control mice (FIG. 18F) indicating that this microRNA might play a role in the beta cell dysfunction of diabetes. Of note, we also found that miR-204 expression was significantly elevated in two additional models of diabetes, i.e. BTBRob/ob and A-ZIP/F-1 mice (generous gift of Dr. C. Vinson) (data not shown). Unlike B6-obese mice, which typically have rather mild diabetes, BTBRob/ob mice are not able to compensate for their leptin-deficiency-induced obesity and insulin resistance and develop severe type 2 diabetes consistent with a more pronounced islet phenotype that includes disrupted islet architecture and reduced whole pancreas insulin content[32]. In contrast, A-ZIP/F-1 mice are not obese and lack white adipose tissue (due to adipose-specific transgenic expression of a dominant-negative protein (A-ZIP/F) that blocks C/EBP and Jun-mediated transcription), but are severely diabetic[33]. Despite these differences, both models showed again increased Txnip expression, consistent with our previous findings[5,12] as well as the associated increase in miR-204 levels.

Given the pro-apoptotic effects of TXNIP, we also tested the possibility that miR-204 might induce beta cell apoptosis. However, compared to scrambled control, miR-204 overexpression did lead to no significant increase in the Bax/Bcl2 ratio (p=0.313), no increase in cleaved caspase-3 and no increase in TUNEL positive beta cells (data not shown), indicating that unlike TXNIP this microRNA does not induce beta cell apoptosis. We therefore followed up on our initial observation and tested how miR-204 might affect beta cell function, i.e. insulin production. In fact, miR-204 overexpression in INS-1 cells led to a >2-fold reduction in insulin mRNA expression (FIG. 19A), (Unlike humans, rodents have two insulin genes and while data shown was obtained with primers detecting expression from both rat insulin genes, primers specific for Ins1 or Ins2 showed the same effect.) Of note, in human islets miR-204 overexpression also decreased insulin mRNA similar to INS-1 cells (FIG. 19B) demonstrating that this effect was also relevant to human islet biology. In addition, the decrease in insulin mRNA expression translated at the protein level into significantly reduced insulin content in miR-204 overexpressing cells (FIG. 19C) as well as decreased insulin secretion (FIG. 19D) and fractional insulin secretion (FIG. 19E), The latter indicates that miR-204 might have additional direct effects on insulin secretion. Moreover, the increase in miR-204 levels observed in diabetic B6-obese mice was also associated with a significant decrease in insulin gene expression (data not shown). Similarly, elevated miR-204 levels were also associated with reduced insulin gene expression in BTBRob/ob and A-ZIP/F-1 mice, the two additional diabetes models tested (data not shown). In contrast, transfection of miR-204 inhibitor oligonucleotides not only resulted in effective inhibition of miR-204, but also in a significant increase in insulin mRNA levels indicating that miR-204 regulates insulin gene expression (data not shown). Surprisingly though, we observed that miR-204 inhibited insulin promoter activity (FIG. 19F), rather than having classical post-transcriptional microRNA effects on mRNA stability or translation. This indicated that the effect was, indirect and likely mediated by miR-204-induced downregulation of factor(s) involved in insulin transcription.

To identify these factors, we next set out to find the putative gene targets of miR-204 and especially those that might play a role in insulin transcription. We therefore tested whether miR-204 could inhibit the expression of any of the key insulin transcription factors, i.e. MafA/B, NeuroD or Pdx-1[34-37] (which also came up as potential targets using miRWalk algorithms). Indeed, MafA mRNA and protein levels were dramatically reduced in response to miR-204 overexpression (FIG. 20A-B) as well as in vivo in the context of diabetes-induced miR-204, whereas miR-204 inhibition led to a >2-fold increase in MafA expression. In contrast, the other transcription factors were not significantly altered by overexpression or inhibition of miR-204 (data not shown). While MafA has been show to be capable of activating Pdx-1 promoter driven reporter gene expression[38] the expression of MafA and Pdx-1 do not always go hand in hand. Consistent with our findings, MafA expression was found to be decreased in diabetic db/db islets and in response to c-Jun, whereas Pdx-1 expression remained unchanged[39]. In addition, glucose has been shown to induce the expression of MafA, but not that of Pdx-1 in beta cells[40]. Furthermore, we found that miR-204-induced reduction in MafA expression also resulted in dramatically reduced MafA binding to the insulin promoter as assessed by chromatin immunoprecipitation (ChIP) studies (FIG. 20C-D). Together, these findings raised the possibility that MafA was acting as the miR-204 target mediating the effects of this microRNA on insulin gene expression. In fact, comparison of the miR-204 seed sequence and the MafA 3'UTR revealed an almost perfect match (FIG. 20E) indicating that MafA might be a target of miR-204. To address this question, we generated reporter constructs with the wild-type MafA 3'UTR or a mutated MafA 3'UTR (FIG. 20E) cloned downstream of the luciferase gene and assessed miR-204-directed repression of the reporter gene. We found that miR-204 significantly decreased luciferase levels through the wild-type MafA 3'UTR, while no reduction was found with the mutant 3'UTR (FIG. 20F), confirming that MafA is indeed a direct target of miR-204. Of note, MafA is highly conserved across species at the protein as well as at the mRNA level and in rats as well as humans and its 3'UTR has been predicted to contain a unique miR-204 binding site. Similar to the rat INS-1 data, miR-204 overexpression also led to a significant reduction in MafA expression in human islets.

To investigate whether TXNIP (as an upstream regulator of miR-204) could mimic the miR-204 effects on MafA, we analysed our TXNIP overexpressing INS-1 cell line and found a >2-fold reduction in MafA mRNA expression and MafA protein levels (FIG. 21A-B) similar to the results in response to direct miR-204 overexpression. In contrast, TXNIP had no effect on Pdx-1, MafB or NeuroD expression levels (data not shown). In addition, ChIP analysis revealed that MafA occupancy of the insulin promoter was reduced to almost half in TXNIP overexpressing cells as compared to INS-LacZ control cells (FIG. 21C-D). Moreover, TXNIP also reduced MafA expression in human islets (FIG. 21E) confirming the physiological relevance of these findings.

To further test whether TXNIP would also block insulin production similarly to miR-204, we conducted parallel experiments using our TXNIP overexpressing INS-1 cells as well as human islets and TXNIP deficient HcB-19 mouse islets. Indeed, TXNIP led to a significant decrease in insulin mRNA levels in INS-1 cells (FIG. 21F) and human islets (FIG. 21G). This transient TXNIP overexpression in the human islets did not lead to any beta cell apoptosis as determined by an unchanged Bax/Bcl2 ratio in the same samples, making any confounding effects in this regard extremely unlikely. At the protein level, TXNIP also caused a dramatic reduction in insulin content (FIG. 21H) and an associated decrease in insulin secretion (FIG. 21I). This effect seemed to have been caused primarily by the reduced insulin content, as fractional insulin secretion was not significantly affected by TXNIP. In contrast, islet of TXNIP deficient mice demonstrated a highly significant, 2-fold increase in insulin content (FIG. 21J) strongly supporting the notion that TXNIP inhibits beta cell insulin production. To further obtain direct evidence for the role of miR-204 in this process, we overexpressed miR-204 in islets of TXNIP-deficient mice, which completely blunted the effect the lack of TXNIP had and reduced the islet insulin content to levels comparable with wild-type control mice (FIG. 21K). This rescue experiment further established the causal relationship between decreased TXNIP and miR-204 and increased insulin production and revealed an important functional link indicating that TXNIP indeed inhibits insulin production through induction of miR-204 expression.

Based on our discovery that TXNIP inhibits STAT3 activation and that STAT3 inhibition in turn increases miR-204 expression, we also investigated the possibility that STAT3 inhibition could regulate insulin production. Indeed, both insulin and MafA expression were significantly reduced in response to STAT3 inhibition (data not shown) providing additional evidence for the importance of this newly identified pathway in conferring the observed TXNIP effects.

Since miR-204 and TRPM3 are co-regulated by TXNIP, we also wanted to address the questions whether any of the observed effects might be mediated by TRPM3. We therefore knocked down TRPM3 using siRNA and assessed whether this could mimic the effects of miR-204 inhibition. However, while we obtained a robust downregulation of TRPM3, neither MafA nor insulin expression were increased (data not shown) and, in contrast to miR-204 inhibition, rather decreased. This indicates that TRPM3 is not conferring the observed TXNIP-mediated inhibition of insulin transcription. Moreover, it indicates that miR-204 is not only able to regulate insulin transcription as demonstrated by miR-204 overexpression and inhibition, but, in the case of TXNIP overexpression, also to outweigh the opposing effects of TRPM3.

Taken together, our findings in INS-1 beta cells, islets of TXNIP-deficient mice, diabetic mouse models and primary human islets demonstrate that TXNIP inhibits STAT3 and induces beta cell transcription of a specific microRNA, miR-204, which in turn blocks insulin production by directly targeting and downregulating the critical transcription factor, MafA. This indicates that this novel TXNIP/p-STAT3/miR-204/MafA/insulin pathway plays a role in impaired insulin production, beta cell dysfunction and the pathogenesis of diabetes (FIG. 5).

References for Example 3

1. Lawrence, M. C., McGlynn, K., Park, B. H. & Cobb, M. H. ERK1/2-dependent activation of transcription factors required for acute and chronic effects of glucose on the insulin gene promoter. *J Biol Chem* 280, 26751-26759 (2005).
2. Khoo, S., et al. MAP Kinases and Their Roles in Pancreatic beta-Cells. *Cell Biochem* Biophys 40, 191-200 (2004).
3. Poitout, V. & Robertson, R. P. Minireview: Secondary beta-cell failure in type 2 diabetes—a convergence of glucotoxicity and lipotoxicity. *Endocrinology* 143, 339-342 (2002).
4. Chen, J., Saxena, G., Mungrue, I. N., Lusis, A. J. & Shalev, A. Thioredoxin-Interacting Protein: A Critical Link between Glucose Toxicity and Beta Cell Apoptosis. *Diabetes* 57, 938-944 (2008),
5. Chen, J., et al. Thioredoxin-Interacting Protein Deficiency Induces Akt/Bcl-xL Signaling and Pancreatic Beta Cell Mass and Protects Against Diabetes. *FASEB J* 22, 3581-3594 (2008).
6. Lee, C., et al. Exosomes mediate the cytoprotective action of mesenchymal stromal cells on hypoxia-induced pulmonary hypertension. *Circulation* 126, 2601-2611 (2012).
7. Paulin, R., et al. Dehydroepiandrosterone inhibits the Src/STAT3 constitutive activation in pulmonary arterial hypertension. *Am J Physiol Heart Circ Physiol* 301, H1798-1809 (2011).
8. Paulin, R., Courboulin, A., Barrier, M. & Bonnet, S. From oncoproteins/tumor suppressors to microRNAs, the newest therapeutic targets for pulmonary arterial hypertension. *J Mol Med (Berl)* 89, 1089-1101 (2011).
9. Courboulin, A., et al. Role for miR-204 in human pulmonary arterial hypertension. *J Exp Med* 208, 535-548 (2011).
10. Nishiyama, A., Masutani, H., Nakamura, H., Nishinaka, Y. & Yodoi, J. Redox regulation by thioredoxin and thioredoxin-binding proteins. *IUBMB Life* 52, 29-33 (2001),
11. Shalev, A., et al. Oligonucleotide microarray analysis of intact human pancreatic islets: identification of glucose-responsive genes and a highly regulated TGFbeta signaling pathway. *Endocrinology* 143, 3695-3698 (2002).
12. Minn, A. H., Hafele, C. & Shalev, A. Thioredoxin-interacting protein is stimulated by glucose through a carbohydrate response element and induces beta-cell apoptosis. *Endocrinology* 146, 2397-2405 (2005),
13. Minn, A. H., et al. Gene expression profiling in INS-1 cells overexpressing thioredoxin-interacting protein. *Biochem Biophys Res Commun* 336, 770-778 (2005).
14. Saxena, G., Chen, J. & Shalev, A. Intracellular Shuttling and Mitochondrial Function of Thioredoxin-interacting Protein. *J Biol Chem* 285, 3997-4005 (2010).
15. Chen, J., Fontes, G., Saxena, G., Poitout, V. & Shalev, A. Lack of TXNIP protects against mitochondria-mediated apoptosis but not against fatty acid-induced ER stress-mediated beta-cell death. *Diabetes* 59, 440-447 (2010).
16. Sun, Y., et al. Development of a micro-array to detect human and mouse microRNAs and characterization of expression in human organs. *Nucleic Acids Res* 32, e188 (2004).
17. Landgraf, P., et al. A mammalian microRNA expression atlas based on small RNA library sequencing. *Cell* 129, 1401-1414 (2007).
18. Winter, J., Jung, S., Keller, S., Gregory, R. I. & Diederichs, S. Many roads to maturity: microRNA biogenesis pathways and their regulation. *Nat Cell Biol* 11, 228-234 (2009).
19. Fernandez-Valverde, S. L., Taft, R. J. & Mattick, J. S. MicroRNAs in beta-cell biology, insulin resistance, diabetes and its complications. *Diabetes* 60, 1825-1831 (2011).
20, Kantharidis, P., Wang, B., Carew, R. M. & Lan, H. Y. Diabetes complications: the microRNA perspective. *Diabetes* 60, 1832-1837 (2011).
21. Tattikota, S. G. & Poy, M. N. Re-dicing the pancreatic beta-cell: do microRNAs define cellular identity? *Embo J* 30, 797-799 (2011).
22. Guay, C., Roggli, E., Nesca, V., Jacovetti, C. & Regazzi, R. Diabetes mellitus, a microRNA-related disease? *Transl Res* 157, 253-264 (2011).
23. Lynn, P. C., et al, MicroRNA expression is required for pancreatic islet cell genesis in the mouse. *Diabetes* 56, 2938-2945 (2007).
24. Kalis, M., et al. Beta-cell specific deletion of dicer1 leads to defective insulin secretion and diabetes mellitus. *PLoS One* 6, e29166 (2011).

25. Melkman-Zehavi, T., et al, miRNAs control insulin content in pancreatic beta-cells via downregulation of transcriptional repressors. *Embo J* 30, 835-845 (2011),
26. Poy, M. N., et al. A pancreatic islet-specific microRNA regulates insulin secretion. *Nature* 432, 226-230 (2004).
27. Zhao, H., et al. Up-regulated pancreatic tissue microRNA-375 associates with human type 2 diabetes through beta-cell deficit and islet amyloid deposition. *Pancreas* 39, 843-846 (2010).
28. Poy, M. N., et al. miR-375 maintains normal pancreatic alpha- and beta-cell mass. *Proc Natl Acad Sci USA* 106, 5813-5818 (2009).
29. Roldo, C., et al. MicroRNA expression abnormalities in pancreatic endocrine and acinar tumors are associated with distinctive pathologic features and clinical behavior. *J Clin Oncol* 24, 4677-4684 (2006).
30. Krol, J., et al. Characterizing light-regulated retinal microRNAs reveals rapid turnover as a common property of neuronal microRNAs. *Cell* 141, 618-631 (2010).
31. Xu, G., Chen, J., Jing, G. & Shalev, A. Preventing beta-Cell Loss and Diabetes With Calcium Channel Blockers. *Diabetes* 61, 848-856 (2012).
32. Clee, S. M., Nadler, S. T. & Attie, A. D. Genetic and genomic studies of the BTBR ob/ob mouse model of type 2 diabetes. *Am J Ther* 12, 491-498 (2005).
33. Moitra, J., et al. Life without white fat: a transgenic mouse. *Genes Dev* 12, 3168-3181 (1998).
34. Artner, I., et al. MafA and MafB regulate genes critical to beta-cells in a unique temporal manner. *Diabetes* 59, 2530-2539 (2010).
35. Sharma, A., et al. The NeuroD1/BETA2 sequences essential for insulin gene transcription colocalize with those necessary for neurogenesis and p300/CREB binding protein binding. *Mol Cell Biol* 19, 704-713 (1999).
36. Le Lay, J. & Stein, R. Involvement of PDX-1 in activation of human insulin gene transcription. *J Endocrinol* 188, 287-294 (2006).
37. Aramata, S., Han, S. I., Yasuda, K. & Kataoka, K. Synergistic activation of the insulin gene promoter by the beta-cell enriched transcription factors MafA, Beta2, and Pdx1. *Biochim Biophys Acta* 1730, 41-46 (2005).
38. Vanhoose, A. M., et al. MafA and MafB regulate Pdx1 transcription through the Area II control region in pancreatic beta cells. *J Biol Chem* 283, 22612-22619 (2008),
39. Matsuoka, T A., et al. Regulation of MafA expression in pancreatic beta-cells in db/db mice with diabetes. *Diabetes* 59, 1709-1720 (2010).
40. Vanderford, N. L., Andrali, S. S. & Ozcan, S. Glucose induces MafA expression in pancreatic beta cell lines via the hexosamine biosynthetic pathway. *J Biol Chem* 282, 1577-1584 (2007).
41. Rani, S., et al, Decreasing Txnip mRNA and protein levels in pancreatic MIN6 cells reduces reactive oxygen species and restores glucose regulated insulin secretion. *Cell Physiol Biochem* 25, 667-674 (2010).
42. Zhang, C., et al, MafA is a key regulator of glucose-stimulated insulin secretion. *Mol Cell Biol* 25, 4969-4976 (2005),
43. Kostromina, E., et al. Glucose intolerance and impaired insulin secretion in pancreas-specific signal transducer and activator of transcription-3 knockout mice are associated with microvascular alterations in the pancreas. *Endocrinology* 151, 2050-2059 (2010).
44. Tang, X., Muniappan, L., Tang, G. & Ozcan, S. Identification of glucose-regulated miRNAs from pancreatic {beta} cells reveals a role for miR-30d in insulin transcription. *Rna* 15, 287-293 (2009).
45. Zhao, X., Mohan, R., Ozcan, S. & Tang, X. MicroRNA-30d induces insulin transcription factor MafA and insulin production by targeting mitogen-activated protein 4 kinase 4 (MAP4K4) in pancreatic beta-cells. *J Biol Chem* 287, 31155-31164 (2012).
46. El Ouaamari, A., et al. miR-375 targets 3'-phosphoinositide-dependent protein kinase-1 and regulates glucose-induced biological responses in pancreatic beta-cells. *Diabetes* 57, 2708-2717 (2008).
47. Bolmeson, C., et al. Differences in islet-enriched miRNAs in healthy and glucose intolerant human subjects. *Biochem Biophys Res Commun* 404, 16-22 (2011).
48. Krutzfeldt, J., et al. Silencing of microRNAs in vivo with 'antagomirs'. *Nature* 438, 685-689 (2005).
49. Cha-Molstad, H., Saxena, G., Chen, J. & Shalev, A. Glucose-stimulated Expression of Txnip Is Mediated by Carbohydrate Response Element-binding Protein, p300, and Histone H4 Acetylation in Pancreatic Beta Cells, *J Biol Chem* 284, 16898-16905 (2009).

All publications, patent applications, patents, patent publications and other references cited herein are incorporated by reference in their entireties for the teachings relevant to the sentence and/or paragraph in which the reference is presented.

The foregoing examples are illustrative of the present invention, and are not to be construed as limiting thereof. The invention is described by the following claims, with equivalents of the claims to be included therein.

TABLE 1

| Primers Description | Sequences (5'-3') |
|---|---|
| 1. Human insulin promoter 5' cloning primer | agaacgcgtccccgccctgcagcctccagctc (SEQ ID NO: 3) |
| 2. Human insulin promoter 3' cloning primer | agaaagctttctgatgcagcctgtcctgga (SEQ ID NO: 4) |
| 3. Rat MafA 3'UTR 5' cloning primer | ataactagtgcgcgggaccctgggcct (SEQ ID NO: 5) |
| 4. Rat MafA 3'UTR 3' cloning primer | agtgtttaaacttcttcctttcctcagtttgta (SEQ ID NO: 6) |
| 5. Rat MafA 3'UTR mutant 5' cloning primer | tactgcctatcggcccgagccagatctg (SEQ ID NO: 7) |
| 6. Rat MafA 3'UTR mutant 3' cloning primer | gggccgataggcagtattcaccgttctc (SEQ ID NO: 8) |

TABLE 1-continued

| Primers Description | Sequences (5'-3') |
|---|---|
| 7. Mouse TXNIP qPCR 5' primer | cgagtcaaagccgtcaggat (SEQ ID NO: 9) |
| 8. Mouse TXNIP qPCR 3' primer | ttcatagcgcaagtagtccaaagt (SEQ ID NO: 10) |
| 9. Rat insulin qPCR 5' primer | aggttgcccggcagaag (SEQ ID NO: 11) |
| 10. Rat insulin qPCR 3' primer | gttggtagaagggagcagatgct (SEQ ID NO: 12) |
| 11. Human insulin qPCR 5' primer | acacctgtgcggctcaca (SEQ ID NO: 13) |
| 12. Human insulin qPCR 3' primer | cgttccccgcacactaggta (SEQ ID NO: 14) |
| 13. Rat MafAqPCR 5' primer | aggaggtcatccgactgaaaca (SEQ ID NO: 15) |
| 14. Rat MafAqPCR 3' primer | gcgtagccgcggttctt (SEQ ID NO: 16) |
| 15. Rat MafBqPCR 5' primer | cctacaaggtcaagtgcgagaa (SEQ ID NO: 17) |
| 16. Rat MafBqPCR 3' primer | agcccgcctccctgaa (SEQ ID NO: 18) |
| 17. Rat PDX1 qPCR 5' primer | caaagctcacgcgtggaa (SEQ ID NO: 19) |
| 18. RatPDX1 qPCR 3' primer | tccggttctgctgcgtatg (SEQ ID NO: 20) |
| 19. Rat NeuroD1 qPCR 5' primer | tttggtggctggctgctt (SEQ ID NO: 21) |
| 20. Rat NeuroD1 qPCR 3' primer | gattctgctcaggcaagaaagtc (SEQ ID NO: 22) |
| 21. 18s qPCR 5' primer | agtcctgcccttgtacaca (SEQ ID NO: 23) |
| 22. 18s qPCR 3' primer | gatccgagggcctcactaaac (SEQ ID NO: 24) |
| 23. Rat MafA-Insulin 5' ChIP primer | acgtccaatgagcgctttct (SEQ ID NO: 25) |
| 24. Rat MafA-Insulin 3' ChIP primer | gctgaagctgtaatttccaaacac (SEQ ID NO: 26) |
| 25. Rat GAPDH 5' ChIP control primer | accatgcttcactgacattctga (SEQ ID NO: 27) |
| 26. Rat GAPDH 3' ChIP control primer | ggtctgcctccctgctaacc (SEQ ID NO: 28) |
| 27. Rat TRPM3qPCR 5' primer | cttcgagacacccctcctgtac (SEQ ID NO: 29) |
| 28. Rat TRPM3qPCR 3' primer | tgcccaaatgccagaatgt (SEQ ID NO: 30) |
| 29. MouseTRPM3qPCR 5' primer | gagcaagctcaccgttctcaa (SEQ ID NO: 31) |
| 30. MouseTRPM3qPCR 3' primer | ccattgtcagccaggatgaa (SEQ ID NO: 32) |

TABLE 2

TXNIP effects on beta cell microRNA expression.
Comparison of INS-TXNIP and control INS-LacZ cells by microRNA microarray. Only miRNAs with 4 values across samples have been included in the analysis. Numbers are all log2(Hy3/Hy5); dLMR = difference of LogMedianRatio. Expression sorted by highest differential expression (absolute dLMR).

| Annotation | INS-LacZ | INS-TXNIP | dLMR | fold change |
|---|---|---|---|---|
| rno-miR-139-5p | −1.31 | 0.45 | 1.76 | 3.38 |
| rno-miR-193 | −0.62 | 0.23 | 0.84 | 1.80 |
| rno-miR-204 | −0.34 | 0.39 | 0.73 | 1.66 |
| rno-miR-200c | −0.42 | 0.31 | 0.73 | 1.66 |
| rno-miR-141 | −0.38 | 0.31 | 0.70 | 1.62 |
| rno-miR-187 | 0.24 | −0.44 | −0.68 | 0.62 |
| rno-miR-200b | −0.50 | 0.17 | 0.66 | 1.59 |
| rno-miR-194 | −0.51 | 0.15 | 0.66 | 1.58 |
| rno-miR-130a | 0.34 | −0.31 | −0.66 | 0.63 |
| rno-miR-33 | −0.36 | 0.29 | 0.65 | 1.57 |
| rno-miR-192 | −0.46 | 0.16 | 0.62 | 1.53 |
| rno-miR-32 | −0.49 | 0.06 | 0.54 | 1.46 |
| rno-miR-200a | −0.23 | 0.30 | 0.53 | 1.45 |
| rno-miR-195 | 0.09 | −0.44 | −0.53 | 0.69 |
| rno-miR-212 | 0.07 | −0.44 | −0.51 | 0.70 |
| rno-miR-7b | 0.62 | 1.11 | 0.49 | 1.41 |
| rno-miR-140 | −2.13 | −1.64 | 0.49 | 1.40 |
| rno-miR-335 | −0.06 | 0.41 | 0.47 | 1.39 |
| rno-miR-31 | −0.57 | −0.13 | 0.44 | 1.36 |
| rno-miR-34b | 0.17 | 0.60 | 0.43 | 1.34 |
| rno-miR-34c | −0.52 | −0.11 | 0.41 | 1.33 |
| rno-miR-298 | −0.28 | 0.13 | 0.41 | 1.33 |
| rno-miR-7a | −0.18 | 0.22 | 0.40 | 1.32 |
| rno-miR-29a* | −0.23 | 0.17 | 0.40 | 1.32 |
| rno-miR-455 | 0.20 | −0.20 | −0.40 | 0.76 |
| rno-miR-204* | 0.25 | −0.13 | −0.38 | 0.77 |
| rno-miR-132 | 0.09 | −0.29 | −0.38 | 0.77 |
| rno-miR-365 | −0.22 | 0.13 | 0.35 | 1.28 |
| rno-miR-26b | −0.33 | 0.01 | 0.34 | 1.26 |
| rno-miR-497 | −0.30 | −0.64 | −0.34 | 0.79 |
| rno-miR-375 | −0.11 | 0.23 | 0.33 | 1.26 |
| rno-miR-331 | −0.18 | 0.15 | 0.33 | 1.26 |
| rno-miR-342-3p | −0.16 | 0.15 | 0.31 | 1.24 |
| rno-miR-30b-5p | −0.09 | 0.22 | 0.31 | 1.24 |
| rno-let-7d* | −0.30 | 0.01 | 0.31 | 1.24 |
| rno-miR-30d | −0.09 | 0.22 | 0.30 | 1.23 |
| rno-miR-126 | −0.10 | 0.20 | 0.30 | 1.23 |
| rno-miR-582 | −0.47 | −0.77 | −0.30 | 0.81 |
| rno-miR-101a | −0.19 | 0.10 | 0.29 | 1.23 |
| rno-miR-320 | 0.21 | −0.08 | −0.29 | 0.82 |
| rno-let-7i | 0.20 | −0.09 | −0.29 | 0.82 |
| rno-miR-344-3p | −0.47 | −0.18 | 0.28 | 1.22 |
| rno-miR-140* | −0.36 | −0.08 | 0.28 | 1.22 |
| rno-miR-135a | −0.16 | −0.43 | −0.26 | 0.83 |
| rno-miR-9* | −0.19 | 0.05 | 0.25 | 1.19 |
| rno-miR-374 | −0.27 | −0.03 | 0.24 | 1.18 |
| rno-miR-25* | −0.12 | 0.11 | 0.24 | 1.18 |
| rno-miR-26a | −0.09 | 0.15 | 0.24 | 1.18 |
| rno-miR-128 | −0.07 | 0.16 | 0.23 | 1.17 |
| rno-let-7b | −0.04 | 0.19 | 0.23 | 1.17 |
| rno-miR-23b | 0.02 | 0.25 | 0.23 | 1.17 |
| rno-miR-340-3p | −0.27 | −0.05 | 0.23 | 1.17 |
| rno-miR-24 | −0.08 | 0.14 | 0.22 | 1.17 |
| rno-let-7c | −0.09 | 0.13 | 0.22 | 1.17 |
| rno-miR-24-1* | −0.17 | 0.05 | 0.22 | 1.17 |
| rno-miR-24-2* | −1.07 | −0.85 | 0.22 | 1.16 |
| rno-miR-196a | 0.45 | 0.23 | −0.22 | 0.86 |
| rno-miR-129 | −0.20 | 0.01 | 0.21 | 1.16 |
| rno-miR-29a | −0.10 | 0.11 | 0.21 | 1.16 |
| rno-miR-184 | −0.45 | −0.24 | 0.21 | 1.16 |
| rno-miR-207 | −0.04 | −0.24 | −0.20 | 0.87 |
| rno-miR-30a | −0.20 | −0.01 | 0.20 | 1.15 |
| rno-miR-106b* | −0.38 | −0.18 | 0.19 | 1.14 |
| rno-miR-598-3p | −0.11 | 0.08 | 0.19 | 1.14 |
| rno-miR-350 | 0.09 | 0.28 | 0.19 | 1.14 |
| rno-miR-107 | −0.06 | 0.13 | 0.19 | 1.14 |
| rno-miR-151 | −0.36 | −0.17 | 0.19 | 1.14 |
| rno-miR-153 | −0.07 | 0.11 | 0.18 | 1.13 |
| rno-miR-103 | −0.17 | 0.01 | 0.17 | 1.13 |
| rno-miR-138 | −0.12 | 0.05 | 0.17 | 1.13 |
| rno-miR-129* | −0.10 | 0.07 | 0.17 | 1.12 |
| rno-miR-124 | 0.16 | 0.00 | −0.17 | 0.89 |

TABLE 2-continued

TXNIP effects on beta cell microRNA expression.
Comparison of INS-TXNIP and control INS-LacZ cells by microRNA microarray. Only miRNAs with 4 values across samples have been included in the analysis. Numbers are all log2(Hy3/Hy5); dLMR = difference of LogMedianRatio. Expression sorted by highest differential expression (absolute dLMR).

| Annotation | INS-LacZ | INS-TXNIP | dLMR | fold change |
|---|---|---|---|---|
| rno-miR-532-5p | −0.42 | −0.26 | 0.16 | 1.12 |
| rno-miR-9 | −0.40 | −0.23 | 0.16 | 1.12 |
| rno-miR-191 | −0.10 | 0.06 | 0.16 | 1.12 |
| rno-miR-328 | −0.10 | 0.06 | 0.16 | 1.12 |
| rno-miR-29c | −0.17 | −0.01 | 0.16 | 1.11 |
| rno-miR-25 | −0.13 | 0.03 | 0.16 | 1.11 |
| rno-miR-27b | −0.30 | −0.15 | 0.16 | 1.11 |
| rno-miR-324-5p | −0.28 | −0.13 | 0.15 | 1.11 |
| rno-miR-146b | −0.12 | 0.03 | 0.15 | 1.11 |
| rno-miR-93 | −0.07 | 0.08 | 0.15 | 1.11 |
| 5S_rRNA | 0.14 | −0.01 | −0.15 | 0.90 |
| rno-miR-30e* | −0.28 | −0.13 | 0.15 | 1.11 |
| rno-miR-214 | −0.61 | −0.46 | 0.15 | 1.11 |
| rno-miR-667 | −0.51 | −0.65 | −0.14 | 0.90 |
| rno-miR-210 | −0.30 | −0.17 | 0.13 | 1.10 |
| rno-miR-465 | 0.09 | 0.22 | 0.13 | 1.10 |
| rno-miR-296 | 0.36 | 0.49 | 0.13 | 1.09 |
| rno-miR-384-3p | −0.33 | −0.20 | 0.13 | 1.09 |
| rno-miR-22 | 0.12 | −0.01 | −0.13 | 0.92 |
| rno-miR-106b | 0.09 | 0.22 | 0.13 | 1.09 |
| rno-miR-16 | −0.02 | 0.10 | 0.13 | 1.09 |
| rno-miR-351 | −0.06 | −0.18 | −0.12 | 0.92 |
| rno-miR-652 | −0.11 | 0.01 | 0.12 | 1.09 |
| rno-miR-339-5p | 0.03 | 0.14 | 0.12 | 1.08 |
| rno-miR-185 | −0.08 | 0.03 | 0.12 | 1.08 |
| rno-miR-872* | −0.44 | −0.55 | −0.11 | 0.92 |
| rno-miR-125b-5p | −0.08 | 0.04 | 0.11 | 1.08 |
| rno-miR-96 | −0.15 | −0.26 | −0.11 | 0.93 |
| rno-miR-290 | −0.06 | −0.16 | −0.10 | 0.93 |
| rno-miR-1224 | 0.18 | 0.28 | 0.10 | 1.07 |
| rno-miR-487b | −0.32 | −0.42 | −0.10 | 0.93 |
| rno-miR-743b | −0.43 | −0.34 | 0.10 | 1.07 |
| rno-let-7e | −0.04 | 0.06 | 0.09 | 1.07 |
| rno-miR-22* | −0.01 | −0.11 | −0.09 | 0.94 |
| rno-miR-361 | −0.04 | 0.05 | 0.09 | 1.06 |
| rno-miR-183 | 0.08 | 0.00 | −0.09 | 0.94 |
| rno-miR-29b | −0.08 | 0.00 | 0.08 | 1.06 |
| rno-miR-466b | 0.20 | 0.12 | −0.08 | 0.94 |
| rno-miR-340-5p | −0.02 | 0.06 | 0.08 | 1.06 |
| rno-miR-500 | 0.03 | 0.11 | 0.08 | 1.06 |
| rno-miR-363* | 0.27 | 0.20 | −0.08 | 0.95 |
| rno-miR-15b | 0.02 | −0.05 | −0.07 | 0.95 |
| rno-miR-292-3p | 1.42 | 1.49 | 0.07 | 1.05 |
| rno-miR-877 | −0.31 | −0.25 | 0.06 | 1.05 |
| rno-miR-101b | 0.03 | −0.03 | −0.06 | 0.96 |
| rno-miR-503 | −0.17 | −0.23 | −0.06 | 0.96 |
| rno-miR-125a-3p | 0.31 | 0.24 | −0.06 | 0.96 |
| rno-miR-742 | −0.19 | −0.26 | −0.06 | 0.96 |
| rno-miR-301a | 0.13 | 0.19 | 0.06 | 1.04 |
| rno-miR-378 | 0.08 | 0.14 | 0.06 | 1.04 |
| rno-miR-125a-5p | −0.07 | −0.02 | 0.06 | 1.04 |
| rno-miR-98 | −0.02 | 0.03 | 0.06 | 1.04 |
| rno-miR-494 | −0.14 | −0.20 | −0.06 | 0.96 |
| rno-miR-425 | 0.28 | 0.23 | −0.05 | 0.97 |
| rno-miR-30c | 0.00 | 0.05 | 0.05 | 1.03 |
| rno-miR-99b | 0.06 | 0.01 | −0.05 | 0.97 |
| rno-let-7a | 0.13 | 0.17 | 0.05 | 1.03 |
| rno-miR-203 | 0.36 | 0.40 | 0.05 | 1.03 |
| rno-miR-674-5p | 0.30 | 0.25 | −0.04 | 0.97 |
| rno-miR-675 | 0.06 | 0.10 | 0.04 | 1.03 |
| rno-miR-23a | −0.21 | −0.16 | 0.04 | 1.03 |
| rno-miR-27a | −0.13 | −0.09 | 0.04 | 1.03 |
| rno-miR-325-3p | −0.20 | −0.16 | 0.04 | 1.03 |
| rno-miR-150 | 0.06 | 0.10 | 0.04 | 1.03 |
| rno-miR-466c | 0.12 | 0.16 | 0.04 | 1.03 |
| rno-miR-138* | −0.28 | −0.24 | 0.04 | 1.03 |
| rno-miR-182 | 0.06 | 0.03 | −0.04 | 0.98 |
| rno-miR-672 | 0.39 | 0.42 | 0.04 | 1.02 |
| rno-miR-148b-3p | −0.05 | −0.01 | 0.04 | 1.02 |
| rno-miR-30e | 0.02 | 0.05 | 0.03 | 1.02 |
| rno-miR-423 | −0.16 | −0.13 | 0.03 | 1.02 |
| rno-let-7d | 0.10 | 0.07 | −0.03 | 0.98 |

TABLE 2-continued

TXNIP effects on beta cell microRNA expression.
Comparison of INS-TXNIP and control INS-LacZ cells by microRNA microarray. Only miRNAs with 4 values across samples have been included in the analysis. Numbers are all log2(Hy3/Hy5); dLMR = difference of LogMedianRatio. Expression sorted by highest differential expression (absolute dLMR).

| Annotation | INS-LacZ | INS-TXNIP | dLMR | fold change |
|---|---|---|---|---|
| rno-miR-330 | −0.18 | −0.14 | 0.03 | 1.02 |
| rno-miR-551b | −0.11 | −0.08 | 0.03 | 1.02 |
| rno-miR-30c-1* | 1.46 | 1.49 | 0.03 | 1.02 |
| rno-miR-664 | 0.13 | 0.16 | 0.03 | 1.02 |
| rno-miR-325-5p | 0.17 | 0.14 | −0.03 | 0.98 |
| rno-miR-21 | −0.45 | −0.48 | −0.02 | 0.98 |
| rno-miR-505 | −0.27 | −0.30 | −0.02 | 0.98 |
| rno-miR-668 | −0.25 | −0.27 | −0.02 | 0.99 |
| rno-miR-300-5p | 0.04 | 0.02 | −0.02 | 0.99 |
| rno-miR-186 | 0.06 | 0.04 | −0.02 | 0.99 |
| rno-miR-352 | 0.06 | 0.08 | 0.02 | 1.01 |
| rno-miR-30b-3p | 0.40 | 0.41 | 0.01 | 1.01 |
| rno-miR-196b | −0.31 | −0.32 | −0.01 | 0.99 |
| rno-miR-99b* | 0.32 | 0.31 | −0.01 | 0.99 |
| rno-miR-294 | −0.22 | −0.21 | 0.01 | 1.00 |
| rno-let-7f | −0.06 | −0.06 | 0.00 | 1.00 |
| rno-miR-347 | 0.04 | 0.04 | 0.00 | 1.00 |
| rno-miR-338 | 0.50 | 0.50 | 0.00 | 1.00 |
| rno-miR-384-5p | −0.43 | −0.43 | 0.00 | 1.00 |

What is claimed is:

1. A method of increasing insulin production in a cell that produces insulin, comprising contacting the cell with a microRNA-204 (miR-204)antagonist, thereby increasing insulin production in the cell, wherein the miR-204 antagonist comprises an oligonucleotide that binds to and inhibits or reduces the expression and/or activity of miR-204 or pre-miR-204.

2. The method of claim 1, wherein the cell is in a subject.

3. The method of claim 1, wherein the cell is in a cell culture.

4. The method of claim 3, wherein the cell is a pancreatic islet beta cell substitute, a fibroblast, a hepatocyte, a cord blood stem cell, an alpha cell, a ductal cell, an islet progenitor cell, a mesenchymal stem cell, a peripheral blood stem cell and/or a bone marrow derived stem cell.

5. A method for treating diabetes in a subject in need thereof, comprising administering to the subject a microRNA-204 (miR-204) antagonist in an amount effective to reduce one or more symptoms of diabetes in the subject, thereby treating diabetes in the subject, wherein the miR-204 antagonist comprises an oligonucleotide that binds to and inhibits or reduces the expression and/or activity of miR-204 or pre-miR-204.

6. The method of claim 5, wherein the oligonucleotide comprises one or more modified bases, modified sugar groups, modified phosphate groups, modified nucleoside linkages, terminal modifications, or any combination thereof.

7. The method of claim 5, wherein the oligonucleotide comprises at least one internucleoside phosphodiester linkage, at least one modified sugar moiety and a terminal lipid moiety.

8. The method of claim 5, wherein the oligonucleotide consists of about 15 to about 30 nucleotides and the oligonucleotide comprises, at any location within the about 15 to about 30 nucleotides of the oligonucleotide, a region of contiguous nucleotides that are complementary to the seed sequence of miR-204 (CCUUUCC) or complementary to a sequence having at least 70% identity with the seed sequence of miR-204, wherein each nucleotide of said region of contiguous nucleotides is, in any combination, unmodified or comprises a modified nucleoside linkage, and/or a modified sugar moiety, and wherein each of the remaining nucleotides of the 15 to 30 nucleotide long oligonucleotide is nucleotide X, wherein X can be A, U, C or G in any combination in the nucleotide sequence of the oligonucleotide and wherein, in any combination among the Xs of the oligonucleotide, X is not modified or X comprises a modified nucleoside linkage, and/or a modified sugar moiety.

9. The method of claim 5, wherein the oligonucleotide consists of about 15 to about 30 nucleotides, wherein the oligonucleotide comprises at least about 15 of the nucleotides of the nucleotide sequence of SEQ ID NO:1: 5' AGGCAUAGGAUGACAAAGGGAA 3' or a nucleotide sequence having at least 90% identity with the nucleotide sequence of SEQ ID NO:1, wherein each nucleotide of the nucleotide sequence of SEQ ID NO:1 independently is not modified, or independently comprises a modified nucleoside linkage, and/or a modified sugar moiety.

10. The method of claim 5, wherein the oligonucleotide further comprises a terminal lipid moiety at the 5' terminus, the 3' terminus or both the 5' terminus and the 3' terminus of the oligonucleotide.

11. The method of claim 5, wherein the oligonucleotide is associated with a lipid based carrier system.

12. The method of claim 5, wherein the oligonucleotide comprises a replacement group for phosphate and/or hydroxyl of the nucleotide at the 5' terminus of the oligonucleotide, the 3' terminus of the oligonucleotide or both the 5' and 3' termini of the oligonucleotide.

13. The method of claim 12, wherein the replacement group is biotin, an amino group, a lower alkylamine group, an acetyl group, 2'oxygen-methyl (2'-O-Me), 4,4'-dimethoxytrityl with oxygen (DMTO), fluoroscein, a thiol, acridine, and any combination thereof.

14. A method of decreasing insulin production in a cell that produces insulin, comprising contacting the cell with a microRNA-204 (miR-204) mimic, thereby decreasing insulin production in the cell.

15. The method of claim 14, wherein the cell is in a subject.

16. The method of claim 14, wherein the cell is in a cell culture.

17. The method of claim 15, wherein the cell is an insulinoma cell.

18. The method of claim 14, wherein the miR-204 mimic is UUCCCUUUGUCAUCCUAUGCCU (SEQ ID NO:2) and its complement as a double stranded molecule.

19. The method of claim 8, wherein at least one nucleotide in the region of complementary nucleotides is modified and/or at least one of the nucleotides X is modified.

20. The method of claim 8, wherein at least one of the nucleotides X is modified.

* * * * *